(12) United States Patent
Rival et al.

(10) Patent No.: US 7,511,126 B2
(45) Date of Patent: Mar. 31, 2009

(54) POSITION-INDEPENDENT AND TISSUE SPECIFIC EXPRESSION OF A TRANSGENE IN MILK OF TRANSGENIC ANIMALS

(75) Inventors: Sylvie Rival, Morsang-sur-Orge (FR); Celine Viglietta, Versailles (FR); Joe Attal, Sarcelles (FR); Louis-Marie Houdebine, Buc (FR)

(73) Assignee: Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 10/451,503

(22) PCT Filed: Dec. 21, 2001

(86) PCT No.: PCT/IB01/02812

§ 371 (c)(1),
(2), (4) Date: Jun. 23, 2003

(87) PCT Pub. No.: WO02/052023

PCT Pub. Date: Jul. 4, 2002

(65) Prior Publication Data

US 2004/0265806 A1  Dec. 30, 2004

(30) Foreign Application Priority Data

Dec. 22, 2000 (EP) .................. 00403658

(51) Int. Cl.
C07H 21/02 (2006.01)
C07H 21/04 (2006.01)
(52) U.S. Cl. .................................................. 536/23.1
(58) Field of Classification Search ............. 800/21; 536/23.1
See application file for complete search history.

(56) References Cited

FOREIGN PATENT DOCUMENTS

| WO | WO 92/22644 | 12/1992 |
| WO | WO 93/04172 | 3/1993 |
| WO | WO 94/05796 | 3/1994 |
| WO | WO 98/35689 | 8/1998 |

OTHER PUBLICATIONS

NCBI nucleotide printout of S. scrofa whey acid protein sequence; printout of S. scrofa and M. musculus wap promoter, 6 page total.*
West et al. 2002, Genes and Development, 16:271-288.*
Shamay, et al., 1991, J. Anim. Sci. 69: 4552-4562.*
Rogel-Gaillard et al 1999, Cyogenet. Cell. Genet. 85: 205-211.*
Pinton et al 2004, Genet. Sel. Evol., 36: 123-137.*
Simpson et al., 1998, Journal of Molecular Endocrinology, 20: 27-35.*
Simpson K. et al., "Moleular Characterization and Hormone-Dependent Expression of the Porcine Whey Acidic Protein Gene," Journal of Molecular Endocrinology, vol. 20, No. 1, pp. 27-35 (1998).
Stinnakre M. et al., "Position-independent and Copy-number-related Expression of a Goat Bacterial Artificial Chromosome Alpha-Lactalbumin Gene in Transgenic Mice," Biochem J., vol. 3339, No. 1, pp. 33-36 (1999).
Lewin B., "Genes VII: Chapter 21: Regulation of Transcription: Long Range Regulation and Insulation of Domains", Oxford University Press, Oxford U.K., col. 2, paragraph 6, p. 674 (2000).
Krnacik M et al., "Position-independent Expression of Whey Acidic Protein Transgenes," Journal of Biological Chemistry, vol. 270, No. 19, pp. 11119-11129 (1995).
Li S. et al., "Distal Regulatory Elements Required For Rat Whey Acidic Protein Gene Expression in Transgenic Mice," Journal of Biological Chemistry, vol. 269, No. 9, pp. 14235-14243 (1994).
McKnight, R. et al., "Matrix-attachment Regions Can Impart Position-independent Regulation of a Tissue-Specific Gene in Transgenic Mice," Proceedings of the National Academy of Sciences of USA, vol. 89, No. 15, pp. 6943-6947 (1992).
Rival, S. et al., "Cloning, Transcription and Chromosomal Localization of the Porcine Whey Acidic Protein Gene and Its Expression in HC11 Cell Line," Gene, Elsevier Biomedical Press. Amsterdam, NL, vol. 267, No. 1, pp. 37-47 (2001).

* cited by examiner

*Primary Examiner*—Joanne Hama
(74) *Attorney, Agent, or Firm*—Foley & Lardner LLP

(57) ABSTRACT

The present invention relates to an isolated insulator DNA molecule consisting of the 5' and 3' regions of the porcine wrap gene locus and a method for insulating the expression of an introduced heterologous gene from silencing and variegation effect in chromatin into which the gene has integrated. The invention is also directed to mammalian cells comprising said insulator DNA molecule and non human animals obtained therefrom, which are preferably able to express a polypeptide of interest in milk.

1 Claim, 8 Drawing Sheets

1kb

10kb

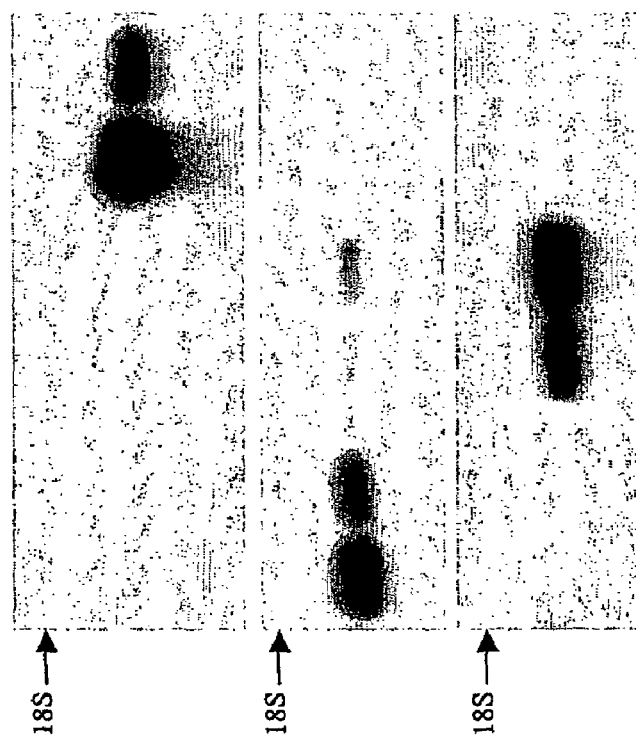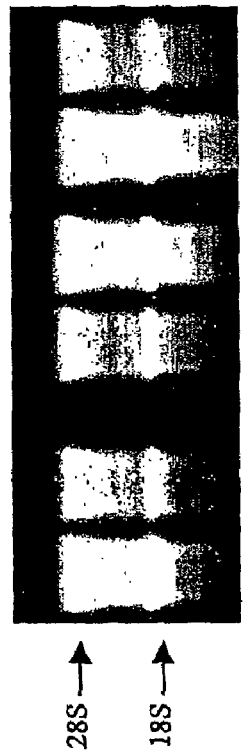

Figure 1A:
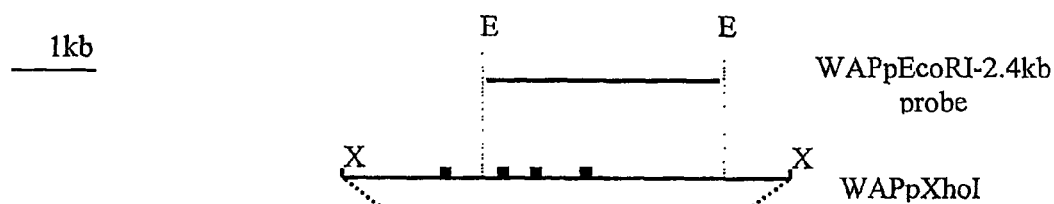

POSITION-INDEPENDENT AND TISSUE SPECIFIC EXPRESSION OF A TRANSGENE IN MILK OF TRANSGENIC ANIMALS

SEQUENCE LISTING

The instant application contains a "Sequence Listing" which has been submitted via duplicate CD-R, and is hereby incorporated by reference in its entirety. The CD-Rs are labeled "CRF" and "Copy 1," respectively, and each contains only one identical 317 kb file, created Jun. 29, 2004. The data contained in the duplicate CD-R "Sequence Listing" are identical to the data contained in the paper "Sequence Listing," submitted Apr. 6, 2004.

The present invention relates to an isolated insulator DNA molecule consisting of the 5' and 3' regions of the porcine wap gene locus and a method for insulating the expression of an introduced heterologous gene from silencing and variegation effect in chromatin into which the gene has integrated. The invention is also directed to mammalian cells comprising said insulator DNA molecule and non human animals obtained therefrom, which are preferably able to express a polypeptide of interest in milk.

The milk is one of the biological fluid which is considered as a major potential source of recombinant proteins for pharmaceutical use and human consumption. The microinjection of hybrid gene containing a promoter specific of the mammary gland into fertilized oocytes has been successfully done since 1987. A general review on transgenic animals as bioreactors and methods for obtaining transgenic animals is available in Houdebine (2000).

However, the proteins encoded by the transgenes may have deleterious effects on transgenic animal health when they are not specifically expressed in the mammary gland of lactating animals. In the other hand, the yield of foreign proteins in the milk of transgenic animals is not predictable and often low. Moreover, the level of expression varies among lines (Palmiter et al., 1984) and even sometimes among animals of the same line (Al-Shawi et al., 1988; Dobie et al., 1996). This fact is dependent mainly of the various integration sites of the transgene into the host genome. Consequently, it often occurs a silencing of the transgenes and variegation providing a mosaicism of transgene expression into tissues from a same animal (Dobie et al., 1997; Festenstein et al., 1996 and Alami et al., 2000).

Different approaches have been proposed to improve the expression of gene constructs. First, some cis-regulatory elements can be linked to the transgene and thus suppress the position effect. For example, the locus control regions (LCR) from the human β-globin cluster or from the CD2 gene are able to confer a position-independent, copy-dependent and tissue-specific expression even if the transgene is integrated near the centromere (Festenstein et al., 1996; Milot et al., 1996). Moreover, insulator elements like the 5'end of the chicken β-globin locus (Chung et al., 1993; Taboit-Dameron et al., 1999), the region spanning the DNase I hypersensitive site (HS) 2-6 of the human T cell receptor (Zhong and Krangel, 1999) or an Alu element from the keratin-18 gene (Willoughby et al., 2000) are able to confer position-independent expression in transgenic mice. For a review of such elements see also U.S. Pat. No. 6,100,448 (increasing expression of transgenes in plant cells using insulator elements), U.S. Pat. No. 6,037,525, (method for reducing expression variability of transgenes in plant cells), and U.S. Pat. No. 5,610,053 (DNA sequence which acts as a chromatin insulator element to protect expressed genes from cis-acting regulatory sequences in mammalian cells). The second possibility is to use long genomic fragments expected to contain all the elements sufficient for an appropriate expression of the transgene. Indeed, the correct expression of the human ApoB gene was obtained in the liver and intestine of transgenic mice after microinjection of a large genomic DNA fragment (70 kb downstream and 22 kb upstream the ApoB gene) but not with smaller fragments (19 kb downstream and 17.5 kb upstream the ApoB gene) (Nielsen et al., 1997).

So far, a few milk protein genes have been expressed in a position-independent fashion in transgenic animals. This was the case for the sheep β-lactoglobulin gene (Whitelaw et al., 1992), the rat WAP gene (Krnacik et al., 1995), the goat α-lactalbumin gene in a BAC vector (Stinnakre et al., 1999) and the human α-lactalbumin gene in a YAC vector (Fujiwara et al., 1997). However, the unpredictability of the expression pattern of most of the transgenes, attributed to the various integration sites of the transgene into the host genome, impedes the preparation of animals that efficiently express transgenes of interest in milk.

The present invention solves the above mentioned problems in that it provides insulator elements allowing position-independent expression of transgenes.

Another issue is to ensure an efficient production of transgenes of interest in milk. Whey acidic protein (WAP) is the major whey protein of rodents (Campbell et al., 1984; Hennighausen and Sippel, 1982), rabbit (Devinoy et al., 1988; Grabowski et al., 1991) and camel (Beg et al., 1986). It has been identified in pig milk (Simpson et al., 1998). The wap gene promoter from mouse or rabbit have been used to direct the production of recombinant proteins in the mammary gland of transgenic animals. The upstream region of mouse wap gene associated to the human protein C (hPC) gene allowed the production of 0.1 to 1.8 g/l of the hPC in the milk of transgenic swine (Van Cott et al., 1996). The bovine growth hormone gene controlled by a 6.3 kb upstream fragment of the rabbit wap gene was expressed at 1 to 16 g/l level in the milk (Thépot et al., 1995). However, these levels varied among lines regardless of the integrated copy numbers and the specificity of expression was dependent on the integration site.

The invention further provides with cis-regulatory elements which are able to direct the efficient expression of the transgene of interest in milk, leading to production of large quantities of heterologous proteins.

In this regard, we have cloned the pig wap cDNA and prepared BAC constructs containing the entire porcine wap gene. The comparison of the coding sequence of the pig wap gene to rodent or lagomorph wap sequence known in the art demonstrated that only exon sequences are partially conserved.

The porcine wap gene was localized on the subtelomeric region of the chromosome 18. The estimation of the expression of the swine wap gene in the mammary gland from lactating animals revealed a high level of expression. In order to compare the expression level of the porcine wap gene from the large genomic fragment which contained 70 kb downstream and 50 kb upstream the pig wap gene or the smaller one (1 kb downstream and 2.4 kb upstream), these two genomic fragments were transfected in HC11 cell line. The BAC construct was expressed fifteen times higher than the plasmid when reported to the integrated copy number. Thus, we demonstrated that the mouse mammary epithelial HC11 cell line is useful as a tool to identify the regulatory sequences of milk protein genes.

Then, we showed using HC11 cells, that one of theses BAC clones, which has 70 kb upstream and 50 kb downstream the wap gene, allowed an expression fifteen times higher than a fragment containing 1 kb of the upstream region.

The expression specificity of a transgene containing the porcine wap gene surrounding with 140 kb upstream region and 5 kb downstream region was tested. Level of expressions was compared between the different transgenic mouse line and the endogenous expression in the mammary gland of a lactating swine.

Thus, the invention provides long genomic fragments isolated around the porcine wap gene which contain all of the regulatory elements necessary to optimize gene expression of a transgene in milk of transgenic animals. Such sequences contain both cis-regulatory elements and insulators allowing position-independent and efficient tissue specific expression of transgenes in milk.

Description

The present invention is aimed at an isolated insulator DNA molecule consisting of the 5' and 3' regions of the porcine wap gene locus, wherein said DNA molecule is isolated from a NotI-NotI fragment of about 145 kb and 75 kb obtainable from BAC 905F9 or BAC 344H5 deposited on Dec. 13, 2000 at the Collection Nationale de Cultures de Micro-organismes (CNCM), Institut Pasteur, 28, rue du Dr Roux, 75724 Paris cédex 15, under the accession numbers I-2595 and I-2596 respectively.

The entire genomic sequence of the porcine wap gene from 40 nucleotides upstream and 2047 downstream the cap site is depicted as SEQ ID No1.

The term "insulator" refers to a DNA segment that prevent the influence of elements in the surrounding chromatin, which act on promoters to enhance or silence gene expression; V. Corces, Nature 376, 462 (Aug. 10, 1995). Where two insulators are employed, they may be the same or different. The insulator according to the invention may encompass fragments of the naturally occurring insulator isolated from the wap gene locus, so long as it retains function as an insulator. The length of the insulator is not critical, but may generally be from 100, 200, or 300 bases up 2000, 3000, 5000, 10000 or more bases in length. In connection with the invention, longer fragments may be used so as to incorporate the cis-acting elements of the wap gene locus and therefore allow efficient expression of heterologous proteins in milk of transgenic animals.

Thus, the DNA molecule according to the invention can further comprise the cis-acting regulatory sequences of the porcine wap gene. The cis-acting regulatory sequences are enhancers that can form a "milk box" and correspond to binding sequences of transcription factors such as GRE, MAF or Stat-5, MPBF, C/EBP and YYI or other factors.

In a second embodiment, the invention is directed to a vector comprising:
(a) at least one isolated insulator DNA molecule as described above;
(b) a promoter domain;
(c) a heterologous gene operably linked to the promoter domain.

In such a vector, at least one (1, 2, or more) insulator is positioned 5' of the promoter so as to operably insulate the transcription and expression of the gene from cis-acting regulatory elements in chromatin into which the gene has integrated.

Alternatively, at least one insulator is positioned 3' of the gene so as to operably insulate the transcription and expression of the gene from cis-acting regulatory elements in chromatin into which the gene has integrated. A vector in which the heterologous gene to be expressed in framed between two insulators is also contemplated.

The term "operatively associated," as used herein, refers to DNA sequences on a single DNA molecule which are associated so that the function of one is affected by the other. Thus, a transcription initiation region is operatively associated with a structural gene when it is capable of affecting the expression of said structural gene.

Vectors according to the invention can be retroviral vectors selected from the spumaviruses; the lentiviruses and the oncoviruses.

Retroviruses are enveloped single-stranded RNA viruses which infect animal cells. When a retrovirus infects a cell, its RNA genome is converted into a double-stranded linear DNA form, which is integrated into the host cell genome. Viral vectors, including recombinant retroviral vectors, provide a more efficient means of transferring genes into cells as compared to other techniques such as calcium phosphate-DNA co-precipitation or DEAE-dextran-mediated transfection, electro-poration, microinjection or lipofection of nucleic acids.

A third embodiment of the invention relates to a DNA construct comprising an expression cassette, which construct comprises, in the 5' to 3' direction, a transcription initiation region, a structural gene positioned downstream from said transcription initiation region and operatively associated therewith, and an insulator according to one of claims 1 to 3 positioned 5' to the transcription initiation region and/or 3' to the structural gene. Such DNA construct can take the form of a vector as mentioned above but also of a plasmid, naked-DNA, episomal vector or artificial chromosome. It is also possible to provide two distinct constructs, one comprising an insulator DNA sequence according to the invention and the other comprising the heterologous gene to be expressed, both construct being injected together in an host cell.

Advantageously, constructs mentioned above can be microinjected directly into early embryos, ES cells, totipotent cells and oocytes, or introduced in spermatic cells.

Among the preferred embodiments, a DNA construct or a vector as depicted above wherein said promoter is the rabbit wap gene promoter allowing efficient expression of a structural gene in milk of animals is contemplated (the rabbit wap gene promoter is described in U.S. Pat. No. 5,965,788). Of course, any other constitutive, or tissue-specific promoter may be employed in frame with the invention.

Among structural genes that can be employed are those encoding a polypeptide or protein selected from antibodies, growth factors, polypeptide, blood factors, enzymes or peptide as commodities or of therapeutic value.

A DNA construct or a vector as depicted above comprising the sequence SEQ ID No1 is also contemplated.

Another embodiment of the invention relates to a method for insulating the expression of an introduced heterologous gene from silencing and variegation effect in chromatin into which the gene has integrated, comprising:
(a) providing a vector or a DNA construct as mentioned above;
(b) transfecting a mammalian cell with said vector or DNA construct; and
(c) integrating the vector or the DNA construct into the chromatin of said cell, wherein the expression of a resultant integrated gene is insulated from cis-acting DNA regulatory sequences in the chromatin of said cell.

In a particular embodiment, the invention concerns a method for insulating the expression of an introduced heterologous gene from silencing comprising:
(a) providing an episomal vector as mentioned above;
(b) transfecting a mammalian cell with said vector.

The invention also relates to a method of making transgenic non-human animals having increased expression of an heterologous gene, said method comprising:
a) transforming a mammalian cell with a vector or a DNA construct as mentioned above;
b) and generating non-human animals from said cell.

A preferred mammalian cell may be an oocyte which has not undergone the final stages of gametogenesis and which can be infected with the herein retroviral vector.

The injected oocytes are then permitted to complete maturation with the accompanying meiotic divisions. The breakdown of the nuclear envelope during meiosis permits the integration of the proviral form of the retrovirus vector into the genome of the oocyte. The injected oocytes can be cultured in vitro under conditions which permit maturation prior to fertilization in vitro. Conditions for the maturation of oocytes from a number of mammalian species (e.g., bovine, ovine, porcine, murine, caprine) are well known to the art. One can refer for example to U.S. Pat. No. 6,080,912 (methods for creating transgenic animals) and to U.S. Pat. No. 5,994,619 (production of chimeric bovine or porcine animals using cultured inner cell mass cells).

Oocytes may also be matured in vivo to practice the present invention. Retroviral vectors capable of infecting the desired species of non-human animals which can be grown and concentrated to very high may be employed as mentioned above. The use of high titer virus stocks allows the introduction of a defined number of viral particles into the perivitelline space of each injected oocyte. In vitro culture conditions which permit the maturation of pre-maturation oocytes from a variety of mammalian species (e.g., cattle, hamster, pigs and goats) are well know to the art [see Parrish et al. (1985) Theriogenology 24:537; Rosenkrans and First (1994) J. Ani. Sci. 72:434; Bavister and Yanagimachi (1977) Biol. Reprod. 16:228; Bavister et al. (1983) Biol. Reprod. 28:235; Leibfried and Bavister (1982) J. Reprod. Fert. 66:87; Keskintepe et al. (1994) Zygote 2:97 Funahashi et al. (1994) J. Reprod. Fert. 101:159 and Funahashi et al. (1994) Biol. Reprod 50:1072].

Other cells that are very useful for obtaining transgenic animals, except humans, are totipotent, pluripotent and ES cells. Methods for culturing and transforming such cells are described in WO 00/27995 (ES cells), WO 00/15764 (propagation and derivation of ES cells), WO 99/27076 (pluripotent embryonic stem cells and methods of obtaining them), WO 99/10488 (site-specific recombination in eukaryotes and constructs useful therefor), U.S. Pat. No. 5,690,926 (pluripotential embryonic cells and methods of making same), WO 97/41209 (pluripotent rabbit embryonic stem cell lines and use in the generation of chimeric rabbit), WO 97/20035 (establishement, maintenance and transfection of totipotent embryonic stem cells from the embryos of animals), U.S. Pat. No. 5,166,065 (in vitro propagation of embryonic stem cells), WO 95/20042 (ES cells isolation), WO 94/23049 (the introduction and expression of large genomic sequences in transgenic animals), WO 99/09141 (porcine totipotent cells and method for long-term culture), WO 97/49803 (trangenesis by genetic transfer into one blastomere of an embryo), WO 97/20035 (establishment, maintenance and transfection of totipotent ES cells from embryos of domestic animals), WO 96/07732 (Totipotent cells for nuclear transfer) and AU3395695 (totipotent cells for nuclear transfer).

Therefore, the invention is also aimed at a mammalian cell, notably at a mammalian cell selected from oocytes, totipotent, pluripotent and ES cells, wherein a DNA construct or a vector as described above has integrated the chromatin of said cells.

According to the state of the art, it is now possible to produce a transformed a somatic cell such as a fibroblast with a vector or a DNA construct according to the invention and to use it for the nuclear transfer into a recipient cell which will in turn produce an embryo. Nuclear transfer techniques are described in WO 95/17500, WO 97/07668, WO 97/07669, WO 98/30683, WO 99/01163 and WO 99/37143.

As a result, another embodiment is directed to a transgenic non-human animal having increased expression of an heterologous gene comprising a cell according to the invention.

Such animals can be selected for example from the group consisting of cows, pigs, sheep, goats, rabbits, rats, and mice.

The invention is not limited to the embodiments depicted above and contemplates as well the following:

The invention also concerns the use of an isolated insulator DNA described herein for preventing the silencing and variegation effect of chromatin into which a heterologous gene has integrated.

For example, it is possible to practice the invention for insulating the differential expression of two genes, consisting of a providing:
(a) at least one isolated insulator molecules according to the invention;
(b) a first expressible gene; (c) a second expressible gene; (d) a promoter that mediates expression of said first gene operably linked to said first gene; (e) a promoter that mediates expression of said second gene operably linked to said second gene;
(f) an enhancer operably linked to the second gene so as to enhance expression of said second gene, wherein said one or more of the insulators is positioned in the construct 5' of the promoter operably linked to the first gene;

wherein the enhancer is positioned 5' of the promoter operably linked to the second gene which is positioned in opposite transcriptional orientation to said first gene; and further wherein one or more of the insulators is positioned 3' of the first and second genes.

Alternatively, it is provided a DNA construct for insulating the differential expression of two genes encoding two different proteins comprising:
(a) one or more isolated eukaryotic insulator molecules according to any of claim 2, or 3; (b) a first expressible gene; (c) a second expressible gene; (d) a promoter that mediates expression of said first second gene operably linked to the first gene; (e) a promoter that mediates expression of said second gene operably linked to the second gene; (f) a first enhancer operably linked to the first gene so as to enhance expression of said first gene; and (g) a second enhancer operably linked to the second gene so as to enhance expression of said second gene;

wherein one or more of the insulators is positioned between the first and second enhancer; wherein the first enhancer is operable to enhance the transcriptional activity of the promoter of the first gene; and wherein the second enhancer is operable to enhance the transcriptional activity of the promoter of the second gene; and further wherein one or more of the insulators is positioned at the 3' of the first and second genes.

Another possibility to practice the invention is to use an isolated insulator DNA described herein for preventing the silencing and variegation effect of chromatin into which two heterologous genes have been integrated. Indeed, it is possible to direct the simultaneous expression of two different structural genes, wherein at least one Internal Ribosome Entry Site is operatively linked to at least one of said genes.

Figure 1B:
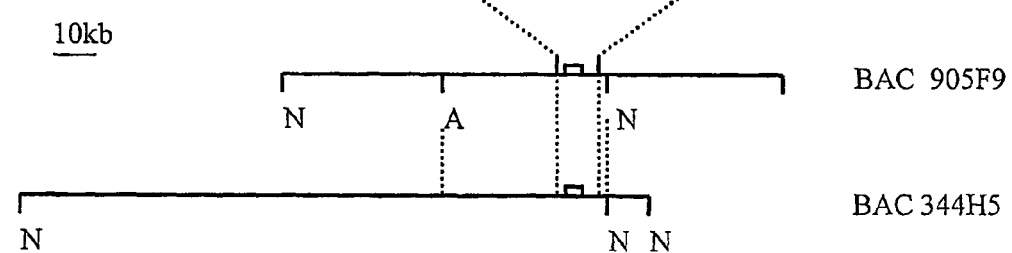

A general review of IRES controlled translation is available in Houdebine et Attal, 1999, Transgenic research, 8: 157-177 and in Ohlmann et al, January 2000, m/s (medecines/sciences), vol 16, 77-86. More specifically, retroviral vectors containing IRES and methods of gene transfer using retrotransposons have been described in WO 93/03143 and WO 92/07950, respectively. Different DNA constructs for expressing simultaneously two genes in a vector comprising a promoter and an IRES is depicted at FIG. 1 of WO 96/01324.

The wap gene has exons with large percentage of identity with rodent and rabbit wap gene. Introns are less conserved as judged by sequence homology and size. Moreover, some of the common transcription signals are also conserved. Indeed, the potential TATA box is a modified TATA consensus sequence like in other WAP gene and the polyadenylation signals is identical.

In order to determine if the cis-regulatory elements of the porcine wap gene may be interesting to direct production of recombinant protein in the mammary gland, an evaluation of the expression of the endogenous wap gene in pig was necessary. First, we determine if the level of expression of the porcine wap gene was comparable to the expression of the rabbit and mouse wap gene. We chose to evaluate the mRNA concentration at the beginning of lactation. It was easy to detect endogenous wap mRNA from the three species since only thirty minutes of exposition were required to reveal intense signals. The pig wap mRNA seemed to be slightly less abundant than those of the mouse and rabbit. Since the mouse and the rabbit wap gene are abundantly expressed in the mammary gland of lactating animals, the pig wap gene seemed also to be well expressed in the mammary gland of lactating swine.

In order to determine if the expression was more intense with large fragment of genomic DNA, porcine wap gene associated to only 1 kb of the promoter region (pWAPpXhoI) and one of the BAC clones which contained 70 kb upstream and 50 kb downstream of the porcine wap gene (BAC 905F9) were transfected in epithelial cell from mammary mouse (HC11). A lower number of the integrated copies was detected from cells transfected by the BAC clone than with the smaller genomic fragment. It may be explained by the size difference between the BAC clone (150 kb) and the plasmid (8,5 kb). Indeed, a DNA fragment 16 times lower than an other one may have more opportunities to be integrated in the host genome. This expression was not detectable by Northern blot analysis and a RT-PCR was performed to compare the two expressions. It was then demonstrated that the BAC 905F9 clone was expressed fifteen times higher than in the smaller genomic fragment when reported to copy number. This may be explained by the presence of additional enhancers and insulators in the long genomic fragment. Moreover, the expression of the wap gene from the BAC clones seemed to be more sensitive to lactogenic hormones since the level of expression increased gradually with insulin, insulin and prolactin, insulin and corticoids and the three hormones (data not shown). These results concur to the evidence that the genomic fragment contain the distal regulatory sequences of milk protein genes. However, only transgenic animals are expected to indicate if this BAC clone is able to give a specific and high expression in the mammary gland of lactating animals (see below).

In order to produce porcine WAP protein in the milk of transgenic mice, a 150 kb DNA fragment from a bacterial artificial chromosome insert containing the porcine WAP-encoding transcription unit was purified according to two different techniques. The first involved a simple phenol-chloroform extraction whereas the other used the GELase enzyme and a dialysis. Both were equally efficient to generate mouse transgenic lines. It then appeared that the usual phenol-chloroform technique may be used to prepare long DNA fragment for microinjection into mouse fertilized oocytes. However, the disadvantage of this method is that the DNA fragment harboring the gene of interest is not separated from the others. The remaining prokaryotic DNA may disturb transgene expression by favoring the methylation of the exogenous DNA or by interfering with the normal environment of the transgene. Interestingly, this fact was not observed. This result confirms that the long DNA fragment harboring the pig wap gene also contained insulators.

Eight animals were transgenic. Two were obtained with phenol-chloroform purified DNA and six with DNA prepared with the other method. One animal did never transmit its transgene and an other one died before he could reproduce. Six lines were then analyzed. All the lactating animals from these lines expressed the porcine wap gene in the mammary gland. Hence, the long genomic fragment allowed expression to be independent of the integration site.

Furthermore, this expression was detected only in the mammary gland. In a virgin animal, no porcine wap mRNA and no endogenous mouse wap mRNA were found by Northern blotting. The expression was therefore developmentally regulated. This DNA fragment thus contains the cis-acting elements involved in the control of the porcine wap gene expression.

The examination of mouse milk composition confirmed this conclusion. A protein expected to be pig WAP was detected by Coomassie brilliant blue coloration only in the milk and in the whey of animals from the line 16. Here, it is shown that the animal BAC16 expressed strongly the porcine wap gene since the corresponding recombinant protein was at a level higher than this of the endogenous murine protein and was more than ten times more concentrated than in the porcine whey. The concentration of the murine WAP protein is known to reach approximately 3 to 5 mg/ml (Hennighausen and Sippel, 1982). The porcine WAP protein was present at this level if not more in the milk of the animal BAC16.

It is further shown that the expression level correlates with the number of integrated copies. The line 16 which harbors 26 copies of the transgene has an expression level 8 fold higher than that of the line 28 which has only 3 copies. However, no difference in the level of expression can be shown clearly in animals harboring only one or two copies since the variation between lines was roughly equal to the differences between animals within the same line.

The porcine BAC clone containing the wap gene according to the invention is therefore able to direct transgene expression in the lactating mammary gland irrespectively of the integration site. So far, only a few milk protein genes have been expressed in a position-independent fashion in transgenic mice. This was the case for the sheep β-lactoglobulin gene (Whitelaw et al., 1992), the rat wap gene (Kmacik et al., 1995), the human α-lactalbumin gene in a YAC (Fujiwara et al., 1997) and the goat α-lactalbumin gene in a BAC (Stinnakre et al., 1999). The porcine BAC clone of the invention represents a new tool to tightly control expression of recombinant protein encoding genes in the mammary gland of lactating transgenic animals. In conclusion, the data here demonstrates that the BAC construct harboring the porcine wap gene contains cis-regulatory elements as well as insulators.

LEGENDS

FIG. 1: Partial map of the WAPpXhoI insert (A) and partial enzyme distribution over the two more interesting BAC clones containing the porcine WAP gene (B). (■) indicates the location of the four exons of the porcine WAP gene. (□) indicates the location of the entire porcine WAP gene. A: AscI; X: XhoI; E: EcORI; N: NotI.

FIG. 2: wap gene transcription in mammary gland of lactating swine, rabbit and mouse. Total RNA (10 and 20 µg) from mammary gland of five days lactating swine and from mammary gland of three days lactating rabbit and mouse were fractionated on denaturing 1.5% agarose/formaldehyde gels, blotted and hybridized to the mouse (A), swine (B) and rabbit (C) wap cDNA labeled by $^{32}$P-dCTP. The equal loading of RNA sample is shown by UV/Ethidium bromide picture of 28 and 18S rRNA (D).

FIG. 3: Porcine wap gene expression in mouse epithelial cell line (HC11). HC11 cell line was cotransfected with the RSVneo and pWAPpXhoI or BAC 905F9. Pools of clones were selected by G418 (150 µg/ml). Cells were cultured as described in. Materials and Methods and harvested 48 h after the hormonal treatment (Insulin, Dexamethasone, Prolactine). A: Specific porcine wap RT-PCR was performed on non transfected HC11 cell line (NT), pWAPpXhoI pool (pWAP-pXhoI) and BAC905F9 pool (BAC905). PCR products were electrophosed on 2% agarose gel. B:PCR products were blotted on nylon membrane and hybridized with labelled porcine cDNA wap1.4 probe. C: To normalize PCR amplification, the endogenous mouse GAPDH cDNA was amplified from RT products, electrophosed on 2% agarose gel, blotted and hybridized with the labelled mouse GAPDH cDNA probe.

D: The number of integrated copies were evaluated by Southern blot using 10 µg of genomic DNA from non transfected HC11 cells (NT), pWAPpXhoI pool (pWAPpXhoI), BAC905 pool (BAC905) and swine genomic DNA digested by EcoRI during 4 h and hybridized by WAPpEcoRI-2.4 kb probe.

Figure 4:
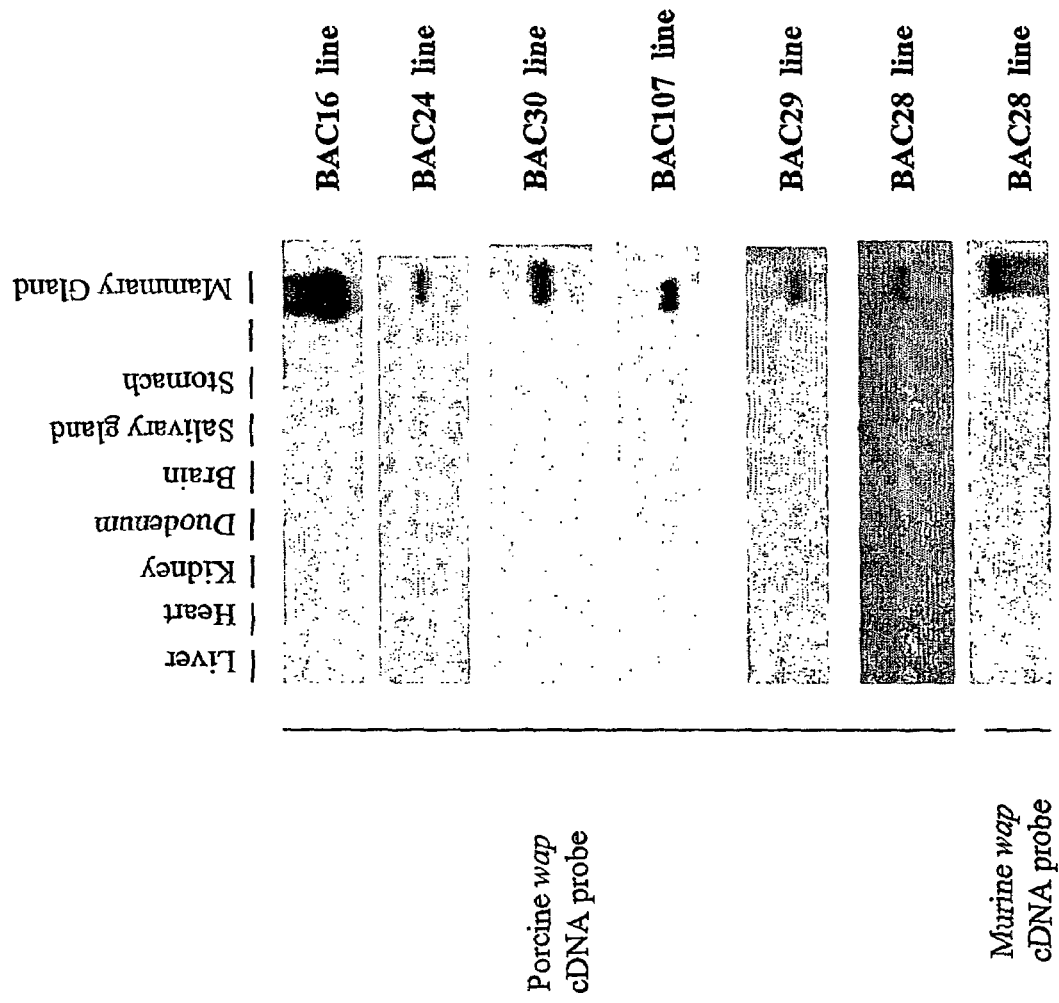

FIG. 4: Tissue specificity expression of the porcine wap transgene

Total RNA was prepared from various tissues of the different transgenic lines. Total RNA (10 µg) was added in each lane of a formaldehyde gel, transferred to a nylon membrane, and hybridized with a [$^{32}$P]-labeled porcine wap cDNA probe and a [$^{32}$P]-labeled murine wap cDNA probe. Hybridized material was visualized using X-rays films.

Figure 5:
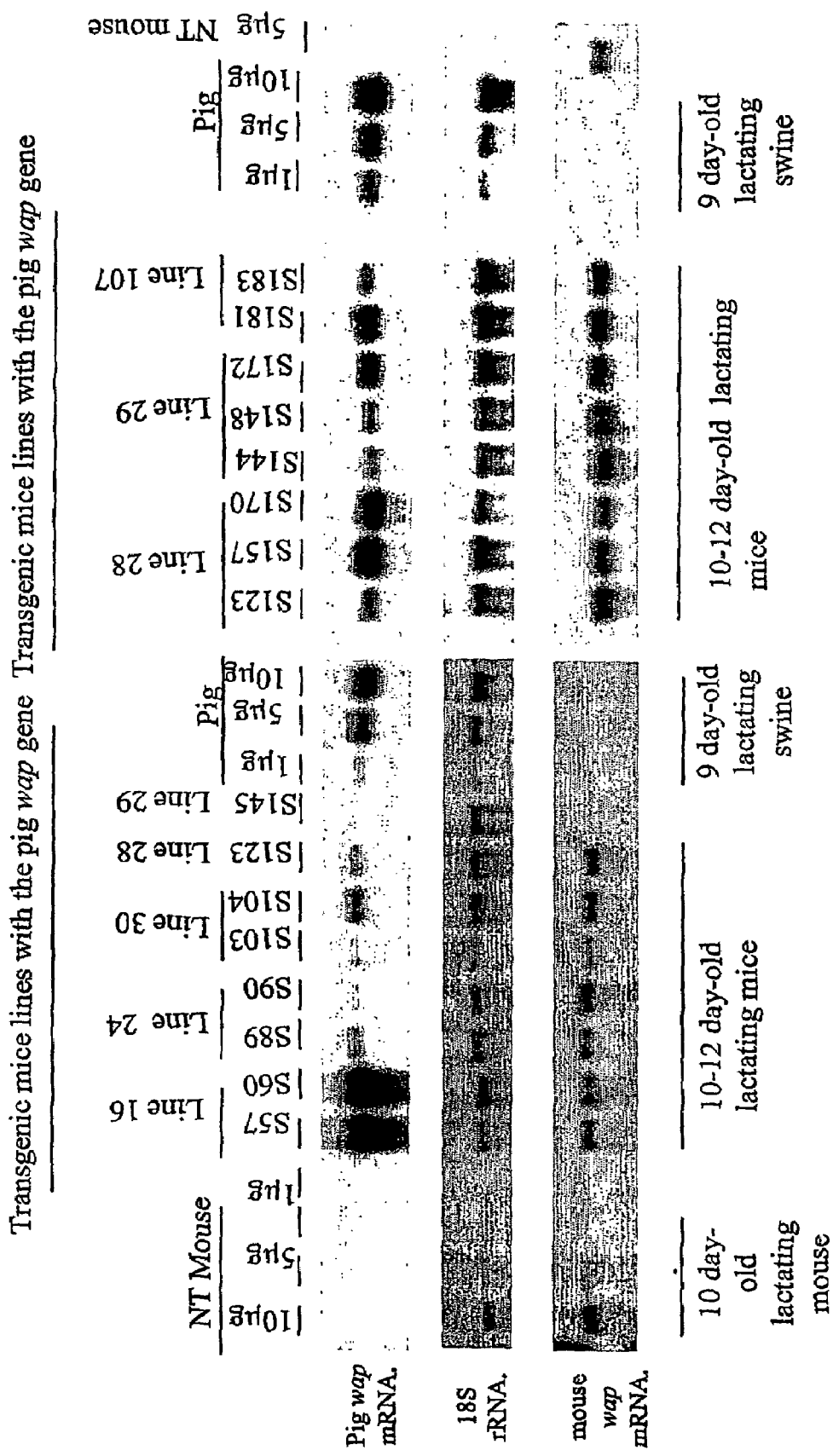

FIG. 5: Comparison of the level of the porcine wap mRNA in the mammary gland of 10-12-days lactating transgenic mice and of a 9-day lactating swine Total RNA was prepared from mammary gland of a 10-day lactating non transgenic mouse (NT), 10 to 12 day of lactating transgenic animals, a virgin transgenic animal (S145) and a 9-day lactating swine. 10 µg of total RNA of the transgenic mice and 10, 5 and 1 µg of total RNA of the lactating non transgenic mouse and the lactating swine were added in each lane of a formaldehyde gel, transferred to a nylon membrane, and hybridized with a [$^{32}$P]-labeled porcine WAP cDNA probe (pig wap mRNA.), a [$^{32}$P]-labeled 18S rRNA probe (18S rRNA), and a [$^{32}$P]-labeled murine wap cDNA probe (mouse wap mRNA.). Hybridized material was visualized using X-rays films.

Figure 6:
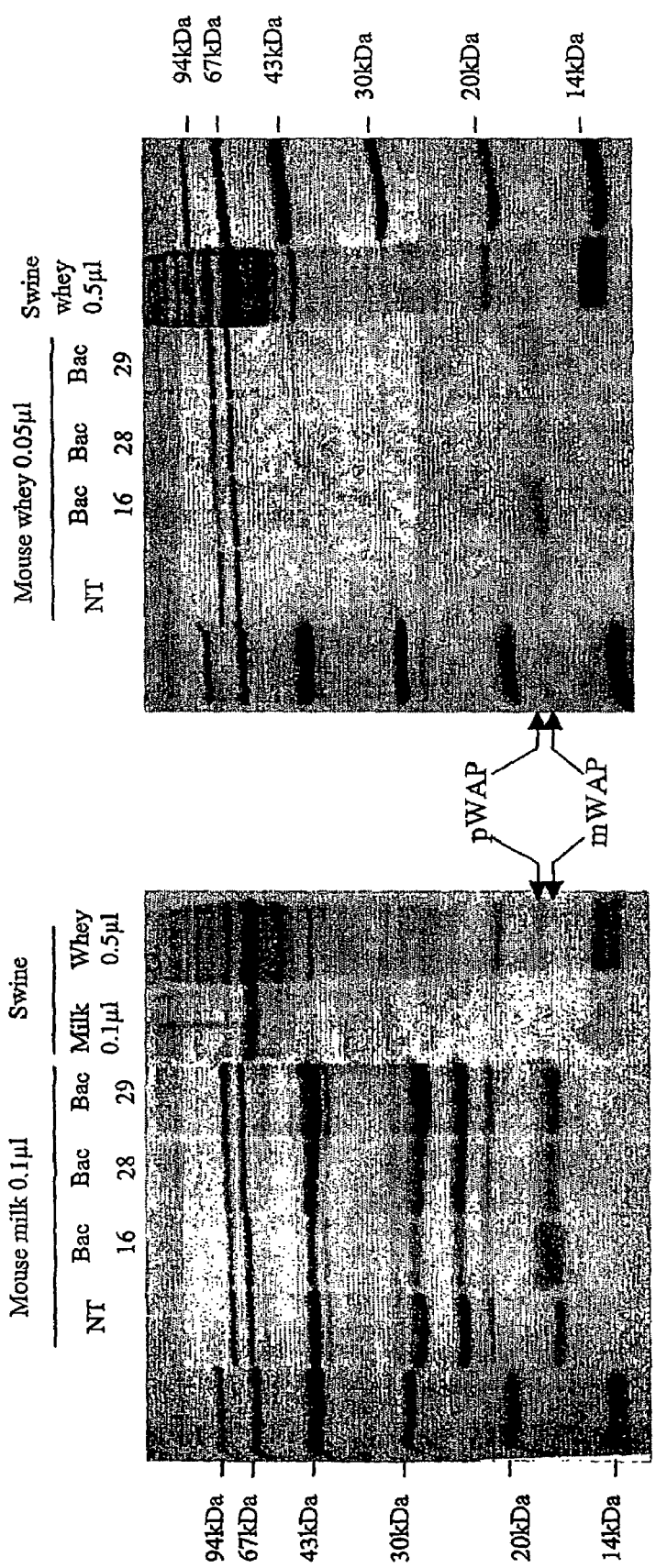

FIG. 6: Comparison of the porcine WAP protein concentration in the milk and in the whey of 10-12-days lactating transgenic mice and of 9-day lactating swine Milk (0.1 µl) from a non transgenic mouse (NT), from transgenic mice (Bac16, Bac28, Bac29) and from a swine and swine whey (0.5 µl) (A.) or whey (0.05 µl) from a non transgenic mouse (NT), transgenic mice (Bac16, Bac28, Bac29) and swine whey (0.5 µl) (B.) were loaded on 16% SDS/PAGE and electrophoresed for 2 hours at 90V. Proteins were visualized by coomassie brillant blue coloration. Porcine WAP protein (pWAP) and murine WAP protein (mWAP) are indicated by arrows.

Figure 7:
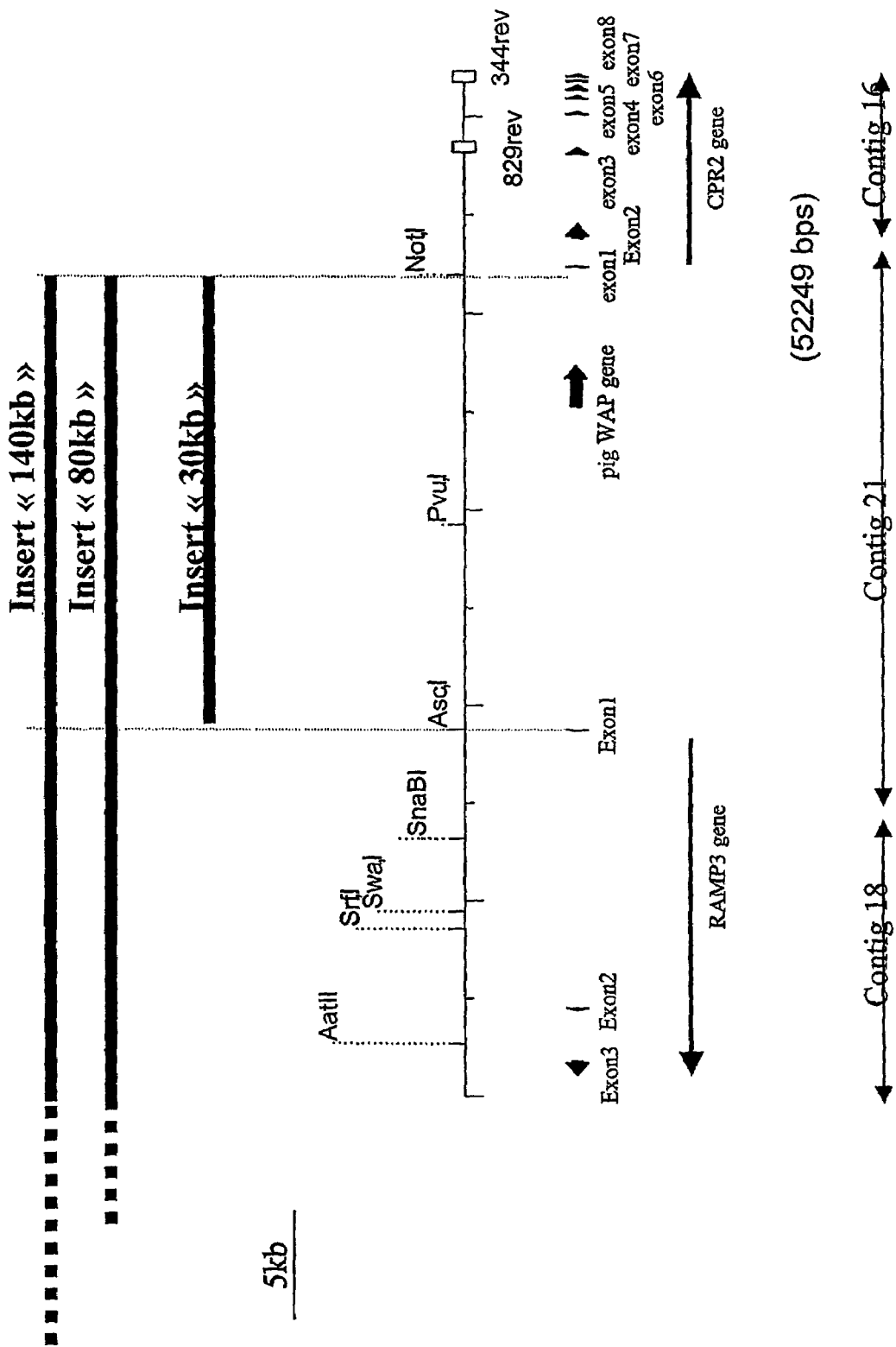

FIG. 7: Pig wap gene locus.

Figure 8:
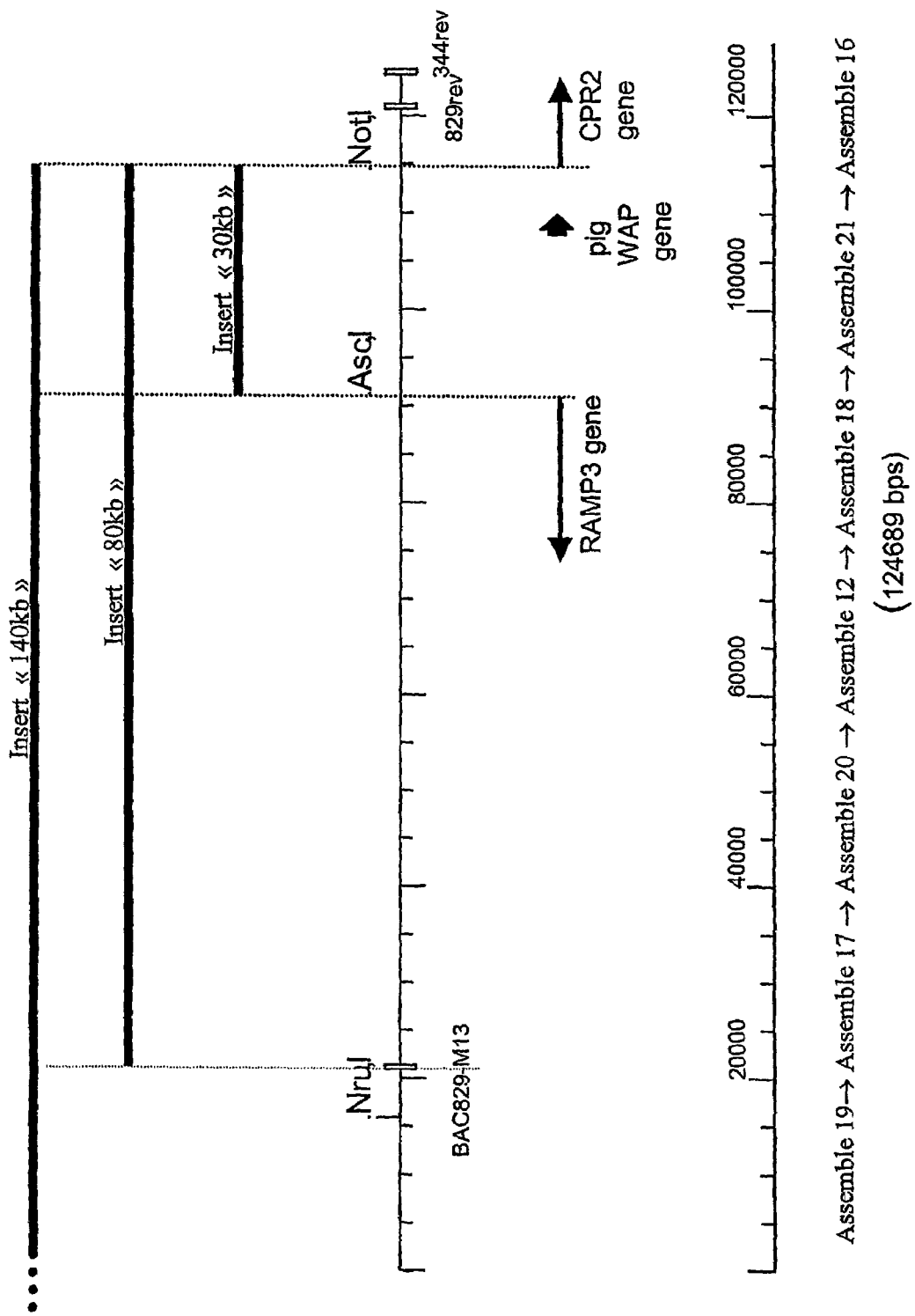

FIG. 8: The sequences of the page are SEQ ID No2 (assemble 19), SEQ ID No3 (assemble 17), SEQ ID No4 (assemble 20), SEQ ID No5 (assemble 12), SEQ ID No6 (assemble 18), SEQ ID No7 (assemble 21), and SEQ ID No8 (assemble 16). The complete sequence of the locus is therefore the continuation of SEQ ID No2 to SEQ ID No8.

EXAMPLE 1

Isolation and Characterization of Porcine wap Gene

Since the nucleic acid sequence of the porcine wap gene was unknown, the cloning of at least a part of the pig wap cDNA was necessary to isolate large genomic fragment from a BAC library. Thus, primers had to be designed in order to amplify specifically the porcine wap cDNA from the mammary gland of a lactating pig. The comparison of the mouse (Hennighausen and Sippel, 1982), rat (Campbell et al., 1984) and rabbit (Devinoy et al., 1988) WAP cDNA sequences showed that two regions are well conserved: the sequences of the signal peptide and the beginning of the third exon. Consequently, two primers were chosen in these conserved regions in order to amplify by RT-PCR the 5'end of the porcine wap cDNA. The unique band (220 bp) obtained by RT-PCR was isolated, cloned in pGEM-T vector (Promega) and both strand were sequenced. An examination of the three possible reading frames revealed that one of them showed a homology of 91.3% with the amino acid sequence of the porcine WAP published by Simpson et al., (1998). Two additional amino acids ($aa_{39}$ and $aa_{40}$) deduced from the sequence of the cloned DNA fragment were found in this part of the WAP protein. This difference between these two WAP protein sequences may result from errors in PCR or sequencing. Alternatively, it may reflect a polymorphism in the porcine wap gene.

From the sequence of the 5' end of the porcine wap cDNA, two specific primers from the porcine wap gene were designed and the porcine BAC library was screened by PCR reaction with the two primer combinations. Five clones (283E5, 344H5, 829G1, 829G6, 905F9) containing the porcine wap gene were isolated and a restriction map was established (FIG. 1). The length of the genomic DNA fragment cloned in these BAC vectors ranged from 120 to 155 kb. Two clones appeared particularly interesting. The BAC 905F9 clone contained the wap gene in the middle of its insert and it then encompassed 70 kb upstream and 50 kb downstream the wap gene. The BAC 344H5 clone encompassed 130 kb upstream of the cap site of the wap gene. These two clones may contained some important elements for the regulation of the wap gene.

From this restriction map, we determined that a 5.4 kb XhoI fragment contained at least the 5'end wap gene. This XhoI fragment was cloned into the XhoI site of the plasmid vector Bluescrpit KS-. A primer walking strategy was chosen to sequence the two WAP gene DNA strands by the dideoxy method. The entire WAP gene was found in the 5.4 kb XhoI fragment and its sequence is available in the EMBL database under the accession number No AF320306.

The porcine wap gene extended over 2 kb. A putative TATA box was found at the expected position, ie −30 bp from the cap site. This TATA box did not look like a typical TATA consensus sequence (Breathnach and Chambon, 1981) but showed a modified sequence (TTTAAAA). Interestingly, this sequence was also found in the WAP gene of the other species (Devinoy et al., 1988) and in most of the milk protein genes studied so far. The pig wap gene was composed of four exons containing 109, 141, 160, 147 nucleotides respectively and three introns formed by 635, 327, 528 nucleotides. The first exon encoded the 28 nucleotides of the 5'-P untranslated region of the mRNA, the 19 amino acids of the signal peptide and the first 8 amino acids of the secreted WAP protein. The last exon included the last 4 amino acids and 129 nucleotides forming the 3'OH untranslated region.

Even if the structural organization of the wap gene was well conserved between species, a comparison of the sequence of the entire wap gene had revealed that only exon sequences were conserved. The sequence of introns showed a very low percentage of identity and their sizes were quite variable. For example, the third intron contained about 1.1 kb length in the mouse, approximately 500 bp in the rat, 369 bp in the rabbit and 517 bp in the pig. The amino acid sequence of the porcine wap showed a homology of 75, 50, 40 and 35% with the WAP proteins from camel, rabbit, rat and mouse respectively (Simpson et al., 1998). The porcine wap cDNA sequence showed a homology of 67.2, 61.6, 59.6% with wap cDNA from rabbit (Genbank:X07943), rat (Genbank:J00801) and mouse (Genbank:V00856) respectively.

EXAMPLE 2

Endogenous wap Gene Expression in Lactating Mammary Gland Materials and Methods

Twenty and ten μg of total RNA from the mammary gland of 5 days lactating swine, 3 days lactating rabbit and 3 days lactating mouse were separated by electrophoresis in three 1.5% agarose formaldehyde denaturing gels as previously described (Puissant et al., 1994). RNA was fragmented by treatment with 50 mM NaOH and then transferred by capillarity onto Biohylon-Z+ membrane (Bioprobe) in the presence of 50 mM sodium phosphate, pH 7. The mouse, rabbit and pig specific probes were obtained by PCR amplification with the degenerated wap1/wap4 primers using wap cDNA from rabbit, mouse and pig as template. The three probes were simultaneously labeled using the random priming technique (Sambrook et al., 1989). Hybridization was carried out overnight at 65° C., followed by autoradiography as previously described (Puissant et al., 1994).

Results:

The WAP protein was firstly isolated from the rodent milk and later in lagomorph, camel and pig milk. Its amount in the whey from different species is variable. Indeed, it was found at the concentration of 1 to 5 g/l in (McKenzie and Larson, 1978; Piletz et al., 1981; Hennighausen et al., 1990) versus 15 g/l in rabbit (Grabowski et al., 1991). Moreover, the production of endogenous WAP depends on the physiological state of the mammary gland since the level of the mouse wap mRNA increases several thousand-fold between the virgin state and mid lactation (Pittius et al., 1988a; Pittius et al., 1988b).

In order to know if the use of the cis-regulatory elements from the BAC clones encompassing the porcine wap gene may be interesting, it was necessary to determine if the level of the expression of the porcine wap gene was comparable to the expression level of the wap gene from rabbit and mouse. Total mammary RNA from five days lactating swine, three days lactating mouse and three days lactating rabbit were extracted and separated by electrophoresis. To obtain probes as similar as possible, three PCR amplifications were performed on RT products from mammary gland RNA with the same primers already used to clone pig wap cDNA and designed according to the conservation of the rabbit, mouse and rat wap cDNA. The three PCR products were purified and then simultaneously labeled with $^{32}$P-dCTP by random priming technique in order to obtain specific activities as similar as possible. Hybridizations of the Northern blots were simultaneously carried out.

In the mammary gland of mouse, rabbit and swine, the wap mRNA was easily detectable (FIG. 2A, FIG. 2C and FIG. 2B respectively) since after only thirty minutes of autoradiography a signal was present. Each probe showed strictly species specific signal except for the porcine wap cDNA probe which partially cross-hybridized with the rabbit wap mRNA (FIG. 2B).

The UV/ethidium bromide picture (FIG. 2D) showed the equal loading of RNA. We may then compare the mRNA level of the different wap genes by quantification of the signals by phosphorimager. We found that the hybridization signal with the porcine wap mRNA was 5 to 8 fold lower and 6 to 8 fold lower than this observed with the mouse wap mRNA and the rabbit wap mRNA respectively.

EXAMPLE 3

Porcine wap Gene Expression in HC11 Cells Materials and Methods

The mouse mammary epithelial cell line HC11 was cultured in growth medium containing RPMI1640 (Eurobio), 10% heat-inactivated fetal bovine serum (FBS, Sigma), insulin (Life Technologies) 5 μg/ml and EGF (Life Technologies) 10 ng/ml as previously described (Ball et al., 1988). Cells were transfected by Lipofectamine® (Life Technologies) according to manufacturer's recommendations with 5 μg of plasmid or BAC DNA and 0,5 μg of the selection plasmid pRSVneo for one 6 cm diameter dish under 50% of confluence. Transfected cells were selected by adding 150 μg/ml of Geneticin in the growth medium. The pools of clones (at least 50 to 100 clones for each transfection) were cultured until confluence. After reaching the confluence, cells were cultured in the growth medium for 4 additional days followed by one day in the growth medium depleted of FBS and EGF but supplemented with transferrin and non essential amino acids (GC3-like medium). Milk protein gene expression was finally induced for the next two days by adding the lactogenic hormones to the GC3-like medium: Insulin (5 μg/ml), Dexamethasone ($10^{-6}$M) and Prolactin (1 μg/ml).

Total RNA was prepared by RNAxel technique (Eurobio) according to the manufacturer's recommendations. RT-PCR analysis was carried out with the AMV reverse transcriptase (first strand cDNA synthesis kit for RT-PCR, Roche Diagnosys Boehringer Mannheim Corp., Indianapolis, USA) using 1 μg total RNA, the oligo(dT) primer and a combination of wap primers and of mouse GAPDH previously described (Lee et al., 1999).

The number of integrated copies was evaluated by Southern blot. 10 μg of genomic DNA were digested by EcoRI during 4 hours, fractionated on 1% agarose gel in TBE 1× and then blotted on Biohylon-Z+membrane (Bioprobe). Hybridization was performed with the labelled WAPpEcoRI 2,4 kb probe.

Results:

HC11 cell line is derived from the spontaneously immortalized COMMA ID cells which were isolated from the mammary gland of a midpregnant mouse (Ball et al., 1988). In this cell line, milk protein genes are sensitive to lactogenic hormones (insulin, hydrocortisone and prolactin) and to cell-cell interactions. Moreover, the transfected rat β-casein-cat gene expression was considerably enhanced under optimal conditions of induction previously defined (Doppler et al., 1990). In order to determine if the use of large genomic fragments of the porcine wap gene containing more regulatory elements allows a higher and better expression than smaller fragments, the comparison of the expression level of the porcine wap gene associated to only 1 kb of the promoter region (pWAPpXhoI) or associated to 70 kb upstream and 50 kb downstream of the porcine wap gene (BAC905F9) was performed. These two genomic fragments were transfected independently in HC11 cell line with a selection plasmid, pRSVneo. Pools of 50 to 100 clones were isolated by geneticin selection. Pools were maintained under confluence for four days in the complete culture medium and one more day in culture medium depleted in serum and EGF. Induction was then performed during two additional days with insulin, dexamethasone and prolactin. The level of expression in each pool was estimated by RT-PCR (FIG. 3).

Figures 3A, 3B, 3C, 3D:
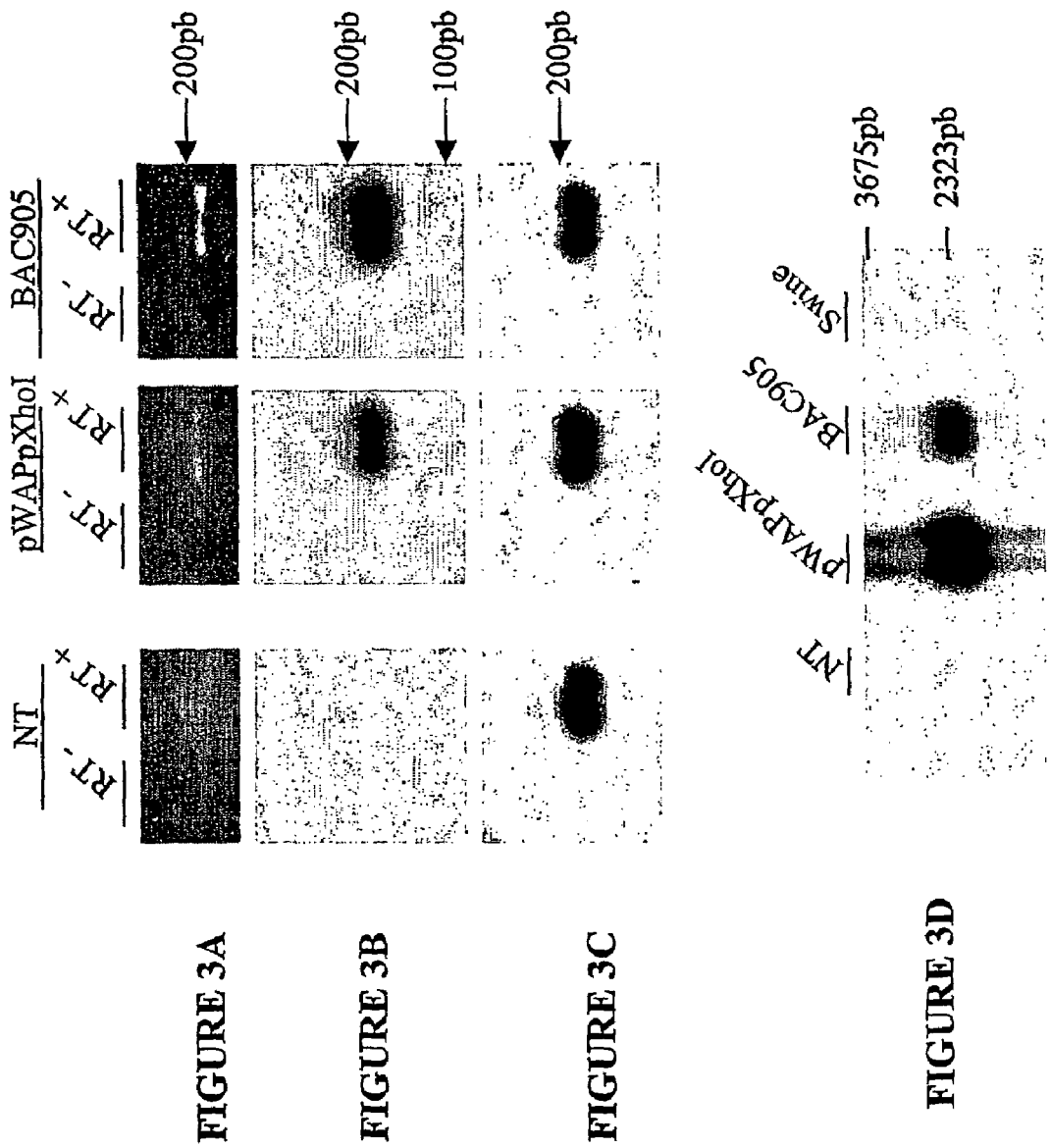

The primers used for RT-PCR were specific of the porcine wap cDNA since no signal was obtained with the non transfected HC11 cells. The UV/ethidium bromide picture showed a higher amount of RT-PCR product with the RNA from BAC905F9 pool cells than from the pWAPpXhoI pool cells (FIG. 3A.). These RT-PCR products were transferred to nylon membrane and hybridized with the porcine wap cDNA probe. To normalize the RT-PCR amplification, the endogenous mouse GAPDH cDNA was amplified (FIG. 3C.) from the same RT sample by specific primers previously described (Lee et al., 1999). The quantification of the radioactive signal (FIG. 3B.) by the Phosporimager™ showed that the expression of the porcine wap gene was three times higher in cells transfected by the BAC905F9 clone than in cells transfected by the pWAPxhoI plasmid. Southern blot analysis (FIG. 3D.) revealed that 28 copies of the wap gene were integrated in the HC11 cell line genome in the case of cells transfected by the BAC 905F9 clone instead of 140 copies in the case of pWAP-pXhoI transfection. Thus, the BAC clone allowed a fifteen fold higher expression per wap gene copy than a smaller genomic fragment.

EXAMPLE 4

Level of Expression in the Mammary Gland of Lactating Transgenic Mice

Materials and Methods

Isolation of the Porcine wap Gene BAC Insert for Micro-Injection and identification of Transgenic Animals The isolation and characterization of the porcine wap gene BAC clones is reported in example 1 above. The BAC 344H5 clone was chosen for this study. BAC DNA prepared with the Nucleobond AX100 column from the Macherey-Naget kit was digested to completion with NotI and the DNA fragment used for the micro-injection of fertilized oocytes was prepared according to two different techniques. The first technique consisted in purifying the DNA fragments obtained after digesting the BAC by NotI by phenol-chloroform extraction. This fraction was directly microinjected into fertilized oocytes. In the second technique, the NotI DNA fragments were size-fractionated by field-inverted gel electrophoresis using a 1% low melting point agarose gel. The BAC insert containing the porcine wap gene was then isolated by GELase (Epicentre) and dialyzed as previously described (Schedl et al., 1993). The concentration of the purified DNA was estimated on a 1% agarose minigel. This BAC fragment, diluted at 1 to 5 ng/μl, was microinjected into the pronuclei of C57B16 X CBA fertilized oocytes. Transgenic mice were identified by PCR analysis performed on genomic DNA extracted from tails as previously described (Attal et al., 1995). Two specific primer sets were used. After 30 cycles of amplification, the PCR products were detected in 1% agarose gel.

Evaluation of Transgene Copy Number in Transgenic Mice by Southern Blot Analysis In order to estimate the copy number of the transgene in each line, genomic DNA were extracted from tails after digestion by proteinase K (Roche) as previously described (Hogan et al., 1986). Genomic DNA (5 μg) from transgenic mice and from a swine was digested to completion with EcoRI restriction enzyme and size fractionated in 1% agarose gel overnight. The fragmented DNA was transferred onto nylon membrane (NytranN, Schleiher et shuell). The blot was hybridized with the labeled WAPpEcoRI 2.4 kb probe, shown in FIG. 1A. Signal quantification was done by autoradiography scanning using a Pharmacia LKB image-master DTS scanning system, according to the manufacturer's guidelines. The signal derived from the hybridization with porcine DNA serves to the two copies reference.

Expression of the Transgene

RNA was prepared by SV total RNA isolation system (Promega) according to the manufacturer's recommendations. Northern blot analysis was performed using 10 μg of the total RNA per sample and size fractionated in formaldehyde/agarose gel (Puissant et al., 1994). The fragmented RNA was transferred onto Biohylon-Z+ membrane (Qbiogene) and hybridized with the appropriate labeled probes. The hybridization signal obtained with the 18S rRNA probe (Raynal et al., 1984), was used as an internal standard to normalize the RNA loading between samples. The murine wap mRNA signal served as an internal standard to estimate differences of the endogenous gene transcription between animals.

Milk or whey protein were fractionated in 16% SDS/PAGE gel at 90V for 2 hours. Proteins were visualized a Coomassie brilliant blue R coloration.

Results

Generation of Transgenic Mice

Five BAC clones containing the porcine wap gene have been described above. When the pBeloBac11 vector was constructed, a NotI restriction site was introduced in its polylinker to separate easily the genomic fragments from the prokaryote DNA vector. Unfortunately, the five porcine wap gene BAC clones contained a NotI restriction enzyme site in their insert, located only 5 kb after the polyadenylation signal site of the porcine wap gene. Hence, it appeared difficult to use a long region downstream of the wap gene. We chose to generate transgenic mice with the BAC344H5 clone which contains the longest region upstream of the porcine wap gene (≈145 kb from the cap site).

Different techniques to extract DNA fragment from BAC clone useful for microinjection into fertilized oocytes have been described. Chrast and collaborators (1999) have tested three methods to extract DNA from 1% low melting point agarose gel. The first one consists in digesting agarose by agarase and purify DNA by a Qiagen tip100 column. The second method uses phenol-chloroform purification and ethanol precipitation instead of Qiagen column. The third method uses the electroelution from agarose. It was shown that the electroelution resulted in the best DNA yield and integrity. These techniques were tested to prepare the NotI fragment from the BAC344H5 clone. None of them gave DNA fragments utilizable for microinjection. For this reason, we chose to purify the insert of approximately 150 kb using two techniques. The first one did not involve the purification of the insert of interest from the two others since digested DNA was purified only by conventional phenol-chloroform extraction. The second technique involved the separation of the wap gene insert from the two others by size fractionation on 1% low melting point agarose gel and pulse field inverted electrophoresis The DNA was purified from agarose by GELase digestion following by a dialyze. These two preparations were microinjected into mouse eggs to produce transgenics.

Two transgenic animals (line 16 and 17) were identified by PCR analysis using genomic DNA from 21 born animals obtained with the DNA purified by phenol-chloroform. With the DNA prepared by the method using the GELase enzyme, 33 animals were born and six of them (line 24, 26, 28, 29, 30 and 107) were transgenics. The rate of transgenic animals was quite similar with one or the other DNA preparation. The animal BAC17 failed to transmit the transgene to its progeny. Nevertheless, 3 integrated copies were detected by Southern blot in this line. The animal BAC26 died before its reproduction and foreign DNA was not detectable by Southern blot. All other founders transmitted the transgene to their progeny and animals from the first generation were studied for transgene expression. The number of integrated copies was estimated by Southern analysis using EcoRI-digested genomic DNA from two or three mice per line. The probed used for hybridization was the 2.4 kb EcoRI fragment of porcine wap gene (FIG. 1A). Line 16 harbored 26 copies of the transgene, lines 24, 29, 30 had 1 copy, line 107 2 copies and line 28 3 copies.

Specificity of Transgene

Northern blot analysis using RNA from different tissues of transgenic animals from each lines showed that the porcine wap gene was expressed abundantly in the lactating mammary gland in all the transgenic lines (FIG. 4). The BAC vector containing the porcine wap gene thus prevented the extinction of the transgene frequently observed with gene constructs containing short genom DNA fragments. In all the six lines studied, the porcine wap mRNA was only detected in the mammary gland of lactating animals. No ectopic expression could be seen in the other examined tissues (liver, heart, kidney, duodenum, brain, salivary gland or stomach). Each Northern blot was hybridized with a mouse wap cDNA probe. The expression pattern of the porcine wap gene was compared to the endogenous wap gene expression. The expression of the porcine wap gene from the BAC344H5 clone integrated randomly in the mouse genome was as specifically expressed in the mammary gland as the mouse endogenous wap gene.

Level of Expression in the Mammary Gland of Lactating Transgenic Mice

In order to evaluate the level expression of the transgene in the mammary gland of the lactating transgenic animals and to compare it to the expression of the endogenous pig wap gene, total RNA from the mammary gland of a non transgenic lactating mouse, of transgenic lactating mice and of a lactating pig were analyzed by Northern blot (FIG. 5). Scale of total RNA loading (1, 5 or 10 µg) from mouse and pig were used to estimate more easily the level of specific mRNA. The first hybridization with a porcine wap cDNA probe showed that it did not cross-hybridized with the endogenous mouse wap mRNA since no signal was detected with the RNA from mammary gland of a non transgenic 10 day-lactating mouse. The data obtained from two or three transgenic animals per line revealed that the level of expression was quite different between the lines. The line 16 expressed abundantly the transgene whereas the five others showed similar expression level. One virgin female from the line 29 was also tested by Northern blotting. No porcine wap mRNA was found in the mammary gland of this animal. The same was true for the endogenous murine wap mRNA measured by a second hybridization with the mouse cDNA probe. The expression was therefore specific of the mammary gland of lactating animals.

The mouse wap cDNA probe was used as an internal standard to estimate the expression level of the endogenous milk protein gene. All animals showed a comparable mouse wap mRNA concentration except for the virgin animal (FIG. 5). The 18S rRNA probe was used as an internal standard to estimate the RNA loading in the gels. The level of expression of the porcine wap gene in the transgenic mice was compared to those of the endogenous porcine wap gene in a 9-day lactating swine. The ratio between the signals from the porcine wap cDNA probe hybridization and from the 18S rRNA probe hybridization were calculated. This ratio from the porcine mammary gland was arbitrary fixed to 1 and the other referred to it. Results are summarized in the table one. Only the line 16 had a content of porcine wap mRNA higher than a 9-day lactating swine. Two of three tested animals from the line 28 had porcine wap mRNA concentration similar to this observed in pig. The other animals showed a lower level of expression. The expression level varied slightly between animals from the same line, except for the line 28 and 107. Indeed, in one of the three studied animals from the line 28, the wap gene expression was nine 9 times lower expression than in two other animals. From the line 107, the animal named BAC183 showed a signal four times lower than the animal BAC181. In no case, different level of expression of endogenous murine wap gene could be seen.

TABLE 1 the wap gene expression level in the mammary gland of lactating transgenic mice Expression is the ratio between the porcine wap mRNA concentration in transgenic mice and the porcine wap mRNA concentration in a lactating swine. Copy numbers were estimated from Southern blot analyses carried out on two or three transgenic animals from each line. Porcine genomic DNA served as a 2 copies reference.

| Founders | F1 animals | Expression ratio | Integrated copy number | Expression/2 copies |
|---|---|---|---|---|
| Bac 16 | | | 26 | |
| | Bac 57 | 12.02 | | 0.92 |
| | Bac 60 | 9.63 | | 0.74 |
| Bac 24 | | | 1 | |
| | Bac89 | 0.36 | | 0.72 |
| | Bac90 | 0.14 | | 0.28 |

TABLE 1-continued the wap gene expression level in the mammary gland of lactating transgenic mice Expression is the ratio between the porcine wap mRNA concentration in transgenic mice and the porcine wap mRNA concentration in a lactating swine. Copy numbers were estimated from Southern blot analyses carried out on two or three transgenic animals from each line. Porcine genomic DNA served as a 2 copies reference.

| Founders | F1 animals | Expression ratio | Integrated copy number | Expression/2 copies |
|---|---|---|---|---|
| Bac 30 | | | 1 | |
| | Bac103 | 0.37 | | 0.74 |
| | Bac104 | 0.56 | | 1.12 |
| Bac 28 | | | 3 | |
| | Bac123 | 0.22 | | 0.14 |
| | Bac157 | 1.52 | | 1.01 |
| | Bac170 | 1.92 | | 1.28 |
| Bac 29 | | | 1 | |
| | Bac144 | 0.31 | | 0.62 |
| | Bac148 | 0.23 | | 0.46 |
| | Bac172 | 0.53 | | 1.06 |
| Bac 107 | | | 2 | |
| | Bac181 | 0.58 | | 0.58 |
| | Bac183 | 0.12 | | 0.12 |

When the expression level was reported to the number of two integrated copies in transgenic mice, it appeared that it was quite similar to the level of expression of the pig wap gene in its natural genomic environment. Except for the two animals noted before (Bac123 and Bac183), the expression levels per 2 integrated copies related to the level of porcine wap gene expression varied not more than 1 to 3 fold between each animal. The expression of the transgene was therefore essentially correlated to the number of integrated copies.

To confirm the RNA analysis, the protein of the mouse milk were performed using denaturing polyacrylamide gel electrophoresis. Since no specific antibody anti pig WAP was available, the Coomassie brilliant blue R coloration was used to reveal the presence of each proteins in the mouse milk (FIG. 6). The porcine wap protein was displayed only in the milk or the whey from the animal Bac16. It is interesting to note that, in the same conditions, the endogenous WAP protein was not detected in the pig milk.

EXAMPLE 5

Further Characterization of the WAP Locus in Pig

The WAP locus in pig has been sequenced. Sequences of the invention are depicted as SEQ ID No2 (assemble 19), SEQ ID No3 (assemble 17), SEQ ID No4 (assemble 20), SEQ ID No5 (assemble 12), SEQ ID No6 (assemble 18), SEQ ID No7 (assemble 21), and SEQ ID No8 (assemble 16) (see FIGS. 7 and 8).

The complete sequence of the locus is therefore the continuation of SEQ ID No2 to SEQ ID No8. A gene having a strong homology with human RAMP3, encoding a transporter protein of a calcitonine-like receptor, has been found in this WAP locus.

In addition, transgenic mice containing the NotI fragment of BAC905F9 of about 80 Kb long and the AscI-NotI fragment of BAC344H5 of about 30 kb long have been obtained. We observed that the 80 Kb fragment allows high and specific expression of a transgene in the mammary gland of lactating transgenic mice.

REFERENCES

Alami, R., J. M. Greally, K. Tanimoto, S. Hwang, Y. Q. Feng, J. D. Engel, S. Fiering and E. E. Bouhassira. 2000. Beta-globin YAC transgenes exhibit uniform expression levels but position effect variegation in mice. Hum Mol Genet 9(4): 631-6.

Al-Shawi, R., J. Burke, C. T. Jones, J. P. Simons and J. O. Bishop. 1988. A Mup promoter-thymidine kinase reporter gene shows relaxed tissue-specific expression and confers male sterility upon transgenic mice. Mol Cell Biol 8(11): 4821-8.

Attal, J., M. Cajero-Juarez and L. M. Houdebine. 1995. A simple method of DNA extraction from whole tissues and blood using glass powder for detection of transgenic animals by PCR. Transgenic Res 4(2): 149-50.

Ball, R. K., Friis, R. R., Schoenenberger, C. A., Doppler, W. and Groner, B.: Prolactin regulation of beta-casein gene expression and of a cytosolic 120-kd protein in a cloned mouse mammary epithelial cell line. Embo J 7 (1988) 2089-95.

Bavister, B. D., Leibfried, M. L. and Lieberman, G.: Development of preimplantation embryos of the golden hamster in a defined culture medium. Biol Reprod 28 (1983) 235-47.

Bavister, B. D. and Yanagimachi: The effects of sperm extracts and energy sources on the motility and acrosome reaction of hamster spermatozoa in vitro. Biol Reprod 16 (1977) 228-37.

Beg, O. U., H. von Bafir-Lindstrom, Z. H. Zaidi and H. Jornvall. 1986. A camel milk whey protein rich in half-cystine. Primary structure, assessment of variations, internal repeat patterns, and relationships with neurophysin and other active polypeptides. Eur J Biochem 159(1): 195-201.

Breatinach, R. and Chambon, P.: Organisation and expression of eucaryotic split genes coding for proteins. Annu Rev Biochem 50 (1981) 349-83.

Campbell, S. M., J. M. Rosen, L. G. Hennighausen, U. Strech-Jurk and A. E. Sippel. 1984. Comparison of the whey acidic protein genes of the rat and mouse. Nucleic Acids Res 12(22): 8685-97.

Chrast, R., Scott, H. S. and Antonarakis, S. E.: Linearization and purification of BAC DNA for the development of transgenic mice. Transgenic Res 8 (1999) 147-50.

Chung, J. H., Whiteley, M. and Felsenfeld, G.: A 5' element of the chicken beta-globin domain serves as an insulator in human erythroid cells and protects against position effect in Drosophila. Cell 74 (1993) 505-14.

Corces, V. G.: Chromatin insulators. Keeping enhancers under control [news; comment]. Nature 376 (1995) 462-3.

Devinoy, E., C. Hubert, E. Schaerer, L. M. Houdebine and J. P. Kraehenbuhl. 1988. Sequence of the rabbit whey acidic protein cDNA. Nucleic Acids Res 16(16): 8180.

Dobie, K., M. Mehtali, M. McClenaghan and R. Lathe. 1997. Variegated gene expression in mice. Trends Genet 13(4): 127-30.

Dobie, K. W., M. Lee, J. A. Fantes, E. Graham, A. J. Clark, A. Springbett, R. Lathe and M. McClenaghan. 1996. Variegated transgene expression in mouse mammary gland is determined by the transgene integration locus. Proc Natl Acad Sci USA 93(13): 6659-64.

Doppler, W., Hock, W., Hofer, P., Groner, B. and Ball, R. K.: Prolactin and glucocorticoid hormones control transcription of the beta-casein gene by kinetically distinct mechanisms. Mol Endocrinol 4 (1990) 912-9.

Festenstein, R., M. Tolalni, P. Corbella, C. Mamalaki, J. Parrington, M. Fox, A. Miliou, M. Jones and D. Kioussis. 1996. Locus control region function and heterochromatin-induced position effect variegation. Science 271(5252): 1123-5.

Fujiwara, Y., M. Miwa, R. Takahashi, M. Hirabayashi, T. Suzuki and M. Ueda. 1997. Position-independent and high-level expression of human alpha-lactalbumin in the milk of transgenic rats carrying a 210-kb YAC DNA. Mol Reprod Dev 47(2): 157-63.

Grabowski, H., D. Le Bars, N. Chene, J. Attal, R. Malienou-Ngassa, C. Puissant and L. M. Houdebine. 1991. Rabbit whey acidic protein concentration in milk, serum, mammary gland extract, and culture medium. J Dairy Sci 74(12): 4143-50.

Hennighausen, L., Burdon, T., McKnight, R., Shamay, A., Sankaran, L. and Wall, R.: Regulation pf milk protein gene. Transgenes, development and Disease 174 (1990).

Hennighausen, L. G. and A. E. Sippel. 1982. Mouse whey acidic protein is a novel member of the family of 'four-disulfide core' proteins. Nucleic Acids Res 10(8): 2677-84.

Hogan, B., F. Costantinii and E. Lacy, 1986. In manipulating the mouse embryo: A laboratory manual, Cold Spring Laboratory Press.

Houdebine, L.-M., 2000. Transgenic animal bioreactors. Transgenic Research 9:305-320.

Houdebine L.-M. et Attal J, 1999. Internal ribosome entry site (IRESs): reality and use. Transgenic research, 8: 157-177

Krnacik, M. J., S. Li, J. Liao and J. M. Rosen. 1995. Position-independent expression of whey acidic protein transgenes. J Biol Chem 270(19): 11119-29.

Lee, D., Ha, S., Kho, Y., Kim, J., Cho, K., Baik, M. and Choi, Y.: Induction of mouse Ca(2+)-sensitive chloride channel 2 gene during involution of mammary gland. Biochein Biophys Res Commun 264 (1999) 933-7.

McKenzie, R. M. and Larson, B. L.: Purification and partial characterization of a unique group of phosphoproteins from rat milk whey. J Dairy Sci 61 (1978) 723-8.

Milot, E., Strouboulis, J., Trimbom, T., Wijgerde, M., de Boer, E., Langeveld, A., Tan-Un, K., Vergeer, W., Yannoutsos, N., Grosveld, F. and Fraser, P.: Heterochromatin effects on the frequency and duration of LCR-mediated gene transcription. Cell 87 (1996) 105-14.

Nielsen, L. B., McCormick, S. P., Pierotti, V., Tam, C., Gurm, M. D., Shizuya, H. and Young, S. G.: Human apolipoprotein B transgenic mice generated with 207- and 145-kilobase pair bacterial artificial chromosomes. Evidence that a distant 5'-element confers appropriate transgene expression in the intestine. J Biol Chem 272 (1997) 29752-8.

Ohlmann et al, January 2000, m/s (medecines/sciences), vol 16, 77-86.

Palmiter, R. D., T. M. Wilkie, H. Y. Chen and R. L. Brinster. 1984. Transmission distortion and mosaicism in an unusual transgenic mouse pedigree. Cell 36(4): 869-77.

Parrish et al. (1985) Theriogenology 24:537

Piletz, J. E., Heinlen, M. and Ganschow, R. E.: Biochemical characterization of a novel whey protein from murine milk. J Biol Chem 256 (1981) 11509-16.

Pittius, C. W., Hennighausen, L., Lee, E., Westphal, H., Nicols, E., Vitale, J. and Gordon, K.: A milk protein gene promoter directs the expression of human tissue plasminogen activator cDNA to the mammary gland in transgenic mice. Proc Natl Acad Sci USA 85 (1988a) 5874-8.

Pittius, C. W., Sanrkaran, L., Topper, Y. J. and Hennighausen, L.: Comparison of the regulation of the whey acidic protein gene with that of a hybrid gene containing the whey acidic protein gene promoter in transgenic mice. Mol Endocrinol 2 (1988b) 1027-32.

Puissant, C., M. Bayat-Sarmadi, E. Devinoy and L. M. Houdebine. 1994. Variation of transferrin mRNA concentration in the rabbit mammary gland during the pregnancy-lactation-weaning cycle and in cultured mammary cells. A comparison with the other major milk protein mRNAs. Eur J Endocrinol 130(5): 522-9.

Raynal, F., B. Michot and J. P. Bachellerie. 1984. Complete nucleotide sequence of mouse 18S rRNA gene: comparison with other available homologs. FEBS Lett 167(2): 263-8.

Rosenkrans, C. F., Jr. and First, N. L.: Effect of free amino acids and vitamins on cleavage and developmental rate of bovine zygotes in vitro. J Anim Sci 72 (1994) 434-7.

Sambrook, J., Fritsch, E. F. and Maniatis, T.: Molecular cloning: A laboratory manual. Cold Spring laboratory press, 1989.

Schedl, A., Z. Larin, L. Montoliu, E. Thies, G. Kelsey, H. Lehrach and G. Schutz. 1993. A method for the generation of YAC transgenic mice by pronuclear microinjection. Nucleic Acids Res 21(20): 4783-7.

Simpson, K. J., P. Bird, D. Shaw and K. Nicholas. 1998. Molecular characterisation and hormone-dependent expression of the porcine whey acidic protein gene. J Mol Endocrinol 20(1): 27-35.

Stinnakre, M. G., S. Soulier, L. Schibler, L. Lepourry, J. C. Mercier and J. L. Yilotte. 1999. Position-independent and copy-number-related expression of a goat bacterial artificial chromosome alpha-lactalbumin gene in transgenic mice. Biochem J 339(Pt 1): 33-6.

Taboit-Dameron, F., Malassagne, B., Viglietta, C., Puissant, C., Leroux-Coyau, M., Chereau, C., Attal, J., Weill, B. and Houdebine, L. M.: Association of the 5'HS4 sequence of the chicken beta-globin locus control region with human EF1 alpha gene promoter induces ubiquitous and high expression of human CD55 and CD59 cDNAs in transgenic rabbits. Transgenic Res 8 (1999) 223-35.

Thépot, D., E. Devinoy, M. L. Fontaine, M. G. Stinnakre, M. Massoud, G. Kann and L. M. Houdebine. 1995. Rabbit whey acidic protein gene upstream region controls high-level expression of bovine growth hormone in the mammary gland of transgenic mice. Mol Reprod Dev 42(3): 261-7.

Van Cott, K. E., B. Williams, W. H. Velander, F. Gwazdauskas, T. Lee, H. Lubon and W. N. Drohan. 1996. Affinity purification of biologically active and inactive forms of recombinant human protein C produced in porcine mammary gland. J Mol Recognit 9(5-6): 407-14.

Whitelaw, C. B., S. Harris, M. McClenaghan, J. P. Simons and A. J. Clark. 1992. Position-independent expression of the ovine beta-lactoglobulin gene in transgenic mice. Biochem J 286(Pt 1): 31-9.

Willoughby, D. A., Vilalta, A. and Oshima, R. G.: An Alu element from the K18 gene confers position-independent expression in transgenic mice. J Biol Chem 275 (2000) 759-68.

Zhong, X. P. and Krangel, M. S.: Enhancer-blocking activity within the DNase I hypersensitive site 2 to 6 region between the TCR alpha and Dad1 genes. J Immunol 163 (1999) 295-300.

The invention claimed is:

1. An isolated DNA molecule comprising the 5' and 3' regions of the pig whey acidic protein gene locus, wherein said DNA molecule is about 145 kb or 75 kb in length and is isolated from a NotI-NotI fragment of about 145 kb or 75 kb obtainable from BAC 905F9 or BAC 344H5 deposited at the Collection Nationale de Cultures de Micro-organismes (CNCM) under the accession numbers I-2595 and I-2596 respectively.

* * * * *

SEQUENCE LISTING

<160> NUMBER OF SEQ ID NOS: 8

<210> SEQ ID NO 1
<211> LENGTH: 2087
<212> TYPE: DNA
<213> ORGANISM: Pig

<400> SEQUENCE: 1

```
cgctgcctcc tttaaaaatg ccccagggcc accagccacc atctgccacc tgcctgccag     60
ccaccaccat gcgctttctt accagtctgg ccctggccct gatcgccctg gaggctgccc    120
tcgcactggc cccagccctc aatctgccag gtaggcccag gagggtcgtc ccgaccttcc    180
ccctctccag gtgtgcccca aaacactatc agacctcac  agtctggcga ccaggacaag    240
aggagcagaa tcgggaaggc acatcccag  ggtcagtaac aacctaagca tgggatggga    300
gctcccatgg tggcacagca agttaaggat ctggcattgt ctctgcagca gctcgggtcc    360
ttgctgaagc acaggttcca tccctggcct aaggacttcc atttgcagcg tgtgtggggt    420
ggggaaaaa  aaagtgggt  gctgcccaga gactcccaca tgctggggaa caaagctaca    480
gggctgaggc cactgtccct ggaaaagaag tgaccagaca gtgaagtgga tgtgggggc    540
acctgtcctg tcctcaggt  cttaactcca cctcctgcag tgggcctgtg gccttgttcc    600
cgaattctca cagctgactc acacttctgt cagcggtcac atttctggca ttttccttc     660
ctggaagcag ggtgttgggg tgccgaggag caggctcccc acgcttcttg tccttgcccc    720
accctgctct tccctaagga gccccatccc accgccccc  acccacctgc ccaccctgtg    780
tgcagggctg gccacgtgcc cagagctcag ctcctcctcc gaggacccct gcgtaatctc    840
ctgcgtcaac gatgagagct gtccccaagg caccaagtgc tgcgccagga gccctgcag    900
ccgatcctgc acggtccccc tcctgggtaa tgccacccat ccctgtgccc agcagagcc    960
ctgctggagg gagggctttg ccaagtgtcc gcctagagtc tgcactccgc acccctctct   1020
cagagaaccc ccggcagccc cacgcactcg gcctggccct gacacgggcc cacggctgga   1080
cccagtcgag gctcccccac ttcttccaat gtcatgcagg ctgcagtctc cctcccggcc   1140
ctgaaggccc caaaccacta aggggtggg  ggtgggggc  ccacggaaga cccacagcag   1200
ggcaggccca gcaagccagc aggtgaggaa ggcctctccc atctctctcc cagtgcctgt   1260
ccccaaggcc ggccgctgcc cctgggtgcc ggccccgctg gccccctgagc tctgcttgga    1320
gaaaaatgag tgctccaggg acgaccagtg tagggggcaac aagaagtgct gcttcagctc   1380
gtgtgccatg aggtgtctgg accctgacac aggtaagttc caagacccc  actcctggga   1440
caccgttctg ggccaccgcc ctgggaatgg tggacttggc ttctcccttg gcctcccctg    1500
aacttggtgg cctccacagg gccccaaagg ccatgatatt caacagaggg tgggggctta    1560
agggacagcg tgacccaggc tgcaccagcc acagacttct gcaggcccct gatgtggtca    1620
ctgggataca gagggtctcc gtctagcaga ggggctcag  aggagccctg acttccgggt    1680
gggacttcag ccaggcccgc ctgccacgct tgtgcctttg ccactcaatc tggggaggag    1740
acctgggcta ggagcccaga gatgcggttc ctggataacc agtccctgcc acccttgacc    1800
ttgccggccc acctacggca atgatgaggg cccaggaggg atgggtgtgg acggctcgct    1860
ggcttgccca cacagtccct ccctccccgc cccacatggg ctgggctcca cctcctctga    1920
ggcctccgtg tccctacag  aggccctct  tcagtgaggg acatccctgg gagccccgg    1980
ctgcaaggag tgaccagccc gagtccactc agcaagaacc ttctctctcg gatccagaga   2040
```

```
ccacacgatg cctcctatct gctgctaata aaaacctact cggcttc         2087

<210> SEQ ID NO 2
<211> LENGTH: 26642
<212> TYPE: DNA
<213> ORGANISM: Pig

<400> SEQUENCE: 2
tgagtagata ctatttttt ttgggtctt tttagggcca cacccatggc atatggatgt    60
tcccaggcta ggggtcgaat cggagctgca gttgccggcg tgcaccacag ccatagcaat   120
gccagatctg agccgtgtct gcgacctaca ccacagctca cggcaatacc agatccttaa   180
cccactgagc caggccaggg atcgaacccg caacctcatg gttcctagtc ggatttgttt   240
ctgctgcgcc acgatgggaa cacctggata ctattttta tcccatttta gagatgtgga   300
agtggacata gaggggtgag ccggttggaa ccctcatagt cagagatctc tgcacttgca   360
tttgtccaaa cacttaaacc aaatcatatg tatttatctc ctccacccct ggacaccagc   420
aaatcaaaca tgtctgcaac tctcatatat tagaaaaata caccctttgta atacattaaa   480
aggattgtac accaattcca gggataccgg gatggttcag tatctgcagc tcaatcgtgt   540
gatacaccac atgaacaaaa tgaaggataa aaatcgtgtg atcatcgcaa tagaggtaga   600
aaaagccttt gataaaattt aacttctctt tatgctaaaa actcaacgaa agtgcacttg   660
gaaggaatgc gccacagcgt aataaaacca cgtgcggcta atggcctgct caaaggtgaa   720
aagccaaaag cttttcctct acgaccagaa acaagacagg aagcccactc ttgtcacttt   780
tattcgacag tacggaaagt cctagtgagc gtgattaggc aagaaaatcc aaattggaaa   840
ggaagaaata aaacggtctc tctctttgca gattgcatga tattatgtat agaaaacctt   900
aaagactcca ccgaaaaact atgagaactg gcaaaggaat tcaggaaagt tgcaggatac   960
aaaaccagta cgcaaacatc agttgccttt ctatacactt ataacagacg agcagaaaaa  1020
gaaattagaa aagcaatctc atttataatt gcatcataaa gaataaaatg tatgtgtata  1080
cgatggaata ttacttgtcc ataaaaaaga ataaaataat gtcatttgca cacacatgga  1140
tgaacctaga aattatcata ctaagtgaag ttagtcaaat agtgaaaggc aaacatatga  1200
tatcacttct atgaagaatc aaagaaaaag gatacaaatg cacttatttg caaaacagaa  1260
acagactcac agacctttt ttttgttttt ttggggggg gcagggctgc acctgcagca  1320
tatggaggtt cccaggctag aggtcgaatt ggagatacat ctgctagcct acaccacagg  1380
cacagcaacg ccagatccaa gtcatgtctt cggcctacac cacagctcac tacaacgcca  1440
gatccttaac cccctgatcg aggccaggga ttgaacctgc gtccgcatgg atcctagcca  1500
cgttcattac cgctgagcca caatgggaac gcctgagtca cagtttttaga gtactaaaag  1560
aaaggaattg tcaacacaga gttctgtatc tgtcagaaaa attttttagga atgaggttga  1620
aataaaatct ttcaaagaag aagaaaaact tagagaattc attgccggca ctgctccaaa  1680
gaattattag aagaatttct cagacagatg gaaaagaatg ccagaaagac tgtgtacatc  1740
aggaagaaag gagtgtaaga gatgctaaat ataagcaagt gtaatcgatt atttttctct  1800
tctggagttt taaagaatag gattgaatgt tggaaggaaa aaaataccac tgcctgatgg  1860
tgttttaaat ttatgtaggt ataataattt caagataaat atagcataaa aggtggaggg  1920
caaagggaac catattgtgg taagtttcta ctttataact gagaataaaa ttgatatcaa  1980
agggagcatc actgaaaata ttatacaaac agacacagta aaaaaaaaat cacaatagat  2040
```

```
acattgaaat ggaatataca tgatatttag caacccaaaa gcaggcagga aaggggtaac    2100
agaggaacaa aagtcagaag gaacaaggag aaaaccaacg ataggatggc agacttacct    2160
gaattcatta cattaaatgt aaatggtctg aacccaataa aaagaatgaa attgtcagaa    2220
tggataaaaa atggaaccca acgatctgct gtccctagac tccatcttta aacagaatga    2280
catgggcaaa ttaaacttaa aaggatggaa caagaagaat ttaatatcac tttcagtcta    2340
tgacaggtca tatggacaaa aaaattgtca tatagacgac ataaagaata caagtagatt    2400
ttctgagtta aatcacactc agattgtatc actcagattt gatttgtata agtcaaaacc    2460
aaggattgcc tatatatata gaatggataa acaacgagga cctactgaat tgcacaggga    2520
attatactca atatcttgta ataacacata atagaaaaaa gtctgaaaaa gaatatatgc    2580
atgtataagt tcatcacttt attgtacact tgaaacggac acaacattgt aaattaacta    2640
tacttcaata aaaaaaatta aaaaaccaaa aaccccccaag attatactgt atcttataaa    2700
atgcctttta tggaaacact caagtaacag tcacagaaat tgaccaatct gatgaatgcc    2760
cacccaataa attgatttca gatactgcat ttctcatctc tagatgctcc atctggttct    2820
tttaaaatct tcccccccacc tcatcatgtt cttgttttct tcaacatcct gttgttagtg    2880
ttgccgtgtg gcgtgtagac cagggatttt ctctaatgag aaaacacttc tctagcaagc    2940
cagatagtaa gtatttcaga cttttgtgagc cataaggtct ctgtcacaac gtttcaactc    3000
tgctattaca gcacaaaaca atatgtaagc tactgagcgt gactattcca attaagcttt    3060
atttatagac actgaaattt tgaactgaat acaattattt ttatcttttt tttttttgc    3120 tttttagggc caaacctttg gcatgtggaa gttcccaggc taggggtcaa atgggagcta    3180
cagctgttgg cctacaccac agctcatggg aatgcaggat ccccgagtca ctgagcaagt    3240
ctagggatgg aacccacacc ctcgtggaca ccagttggat tcatttacgc tgcatcacaa    3300
taggaattct gaatactgtt tttaattgtc ttgaaatact attatccttt tgactttttc    3360
cagcttgtag aaaaggtaca aactattctg agctcatagg tgaaaaaaat gcatgataga    3420
aaatgtttgt ttcttaggtc cgaagctgga ccctagctta gagcatccct cacgctgggt    3480
accatggatg gtgaaaggga tggagagccc aaggacctat gttctgactg gtcatgggat    3540
aaacattcca tgccctgtgt gaggtctggg cattctttcc ccagccttgt ggaactttgc    3600
ttagtatact tagtatactt agtatactta gtaactttgc cgagtgcgtc ttatagactt    3660
agcccagcac caggaaaaac tcaaggcgcc ccttgcggag gttttggggt tctctttctt    3720
gcatacacat ttcttcctga aatgccctca cctgctaact gcctcagcct ctccttctcc    3780
cacctcctca ccgcagcaag gctgaccccc tccaccaggg tccttcttcc ctaggctcct    3840
cagcaaggca tggcgtttct tcttgtttat tgaagctag ttgatttaca atattgtgtt    3900
aatttcaggt gtacaacaaa gtgattcaca gaaacatatg tacctggata gatacacatc    3960
ttccttttca gattctttc tgttacaggt tattatacga tattaagggc agctccctgt    4020
gttcaattgc aggtccttgc tggctggcta ttttatgcta atcccaaacc cttcatttat    4080 ccctacccccg cctttgctt ttggtaaccg taagtttgtt ttctatgtct gtgagtctat    4140
ttctgttttg taaataagtt catccgtatt gtattttat ttatttattt atttgtttat    4200
ttatttattt atttatttat ttatttattt ttagggctgc acctgcagca tatggaagtt    4260
cccaggctag tggtacaatc ggagctatag ctgctggcct acgccacagc cacagcaacc    4320
ctgtgggatc tgagccacat ctgtgaccta ccatagct cacagcactg ccagatcctt    4380
aacccactga gcaaggccgg agatcgaact cgtgtcctcg tggacactag ttgggttcat    4440
```

-continued

```
tactgctgag ccacgatggg aactcttgta ttacattttt agaatccaca tagaggagac    4500
ctcatatgat atttgtcttt ctctgtgtga cttatttcac ttagtatctg gcatggcatc    4560
tttcttttgc cacacccgag gcacgtagaa gttccctggc cagggacgga acccacacca    4620
ctgtagtaac cagagccatg gcagtgacaa tgtcggatcc ttaacccact gagccacagg    4680
gagctccttg ggtgttgcat cttggtggga cattgaagtg atgtcgggc tcatggctca     4740
gtgcggacag caggtgattc atagctgtcc gggttctttc ttgtgggaag ctattccagg    4800
tcttatcagt ggcttttgcc atgcatacga ttgacgtgaa acactgcagc agctttattc    4860
tggttagtgc ttgccttgtg cttttttcttg gtgtttgttt atttgtcttt catagtcaaa    4920
agcattcagg tttagttgtt caagtccatg taacggcctt tgcttttttt tttttttttt    4980
ttgaatagct cagctttta ttatcgaatg ttatagaagt ttagtcaaaa agaccaaagc     5040
ccatatcatc atcagactcc tcagattctt ttttctttgt ttctactttc ttctcctcag    5100
ctggggcagc agtgttggct ggggcaggac ctcctgctgg tgcagcacca gctgctgggg    5160
caggtcacca gcccccacat tgcagatgag gctcccgatg ttgacattgg ccagagcctt    5220
tgcaaacaag cctggccaga atggctcaac atttacacct gctgctttaa tgagagcatt    5280
gatcttatcc tccgtgaccg tcacctcatc gtcgtgcaga atgagggcag agtagatgca    5340
ggcgagctcc gagacggagg ccatggtgcg gaccaatgct aggtggggc tgccaggcgc     5400
ggtgctagtc gccggatgaa gtgagggcct caccccaact cggccttagc ttcctcggaa    5460
gaatcgagca ccttagcggc agctgaggaa aggggccctt tgcttttaa gagggagggt     5520
aatgcgttta cgtggttgtg atcacgcccg cgtgtttttt gggcttcgct gactgatttt    5580
gcggttgtct gtttaccacg ctctttgcct gcttcttgaa ccctccctcc cgacactcac    5640
agggcccaca cttacttcat tcatttcccc ctccgtcgct ttggcagctt acttccgaat    5700
tctcttcctt cagtggcctt aagttcttag cacaaggaac ataaagcttg aagttaaaag    5760
acatctccgt ttctcttctc agctcactca cccagaacgc cttgctcatt tgttgtgtgc    5820
ctctgtctta gctctcattt ctatgtgttt gagaccagaa gaaagttttt ttttttttt     5880
ttttttgct ttttagggca acacccacag catatggagg ttcccaggtt aggggtggaa      5940
tcggaactgc agctgccggc ctacaccaca gccacagcca ggctggattt gacccgtgtc    6000
tgtgacccac accacagctc acggcaacgc cggatcctta acccactgag caaggccagg    6060
gatcgacccc acagcctcgt ggttcctagt tgggttcgtt aaccactgcg caatgacggg    6120
aactccctag ttcttcaaat tgagtgtaaa tctccttttt tgtttctcac ttgactttct    6180
ctccccaccc atctcatgac tgatagcaga gaagactcaa gttccgtccg tcccagagtt    6240
catctcccac caccccgtta ttgtcctgtg tgtccctcc gagttctggg gtgcacgggt      6300
catgcggcag ggggtgcacc tgattgtgag gggtggctgg ccaccctcgt gtctggttcc    6360
ttttggggcc gtctgggccc agctcgggt tggtgtggct cttgccctgg caccttgtct      6420
gcaccacctt cagcctgaag ttgctctgct tccttggctc agcatcccca cgcttggaga    6480
gggcgcagga aaacccgctt ctccacgggg cctcggagtc cagcctgtgt gctgctctga    6540
gtagacacac cccagtggcc atgtccacgc tcctgtcccc tgttctgctg tcaggtctgc    6600
gtgtctgtgc agggttgttg tggcgggagg aggaatccgc tctctgtctg ttttctgaag    6660
cctaagcccc ggtcttctct cagaatccta gagctcccag ggctgccctg gaaagcatgc    6720
ggctgagacc ctcgcagggg ctcccagag catccagctc tctgcttctc cctacccacc     6780
```

```
tcccttccca ccccagagag ggctgtttgg gggcgggtgt gcctgggagc ccacacctgc   6840
cctgggaaag gtgaacaggg caagtgtgcc ccgtagtcac gtctgaaagc ccagaagctg   6900
gtgcacaaac actgtgttgt gtgtctgcct gtctgaggcc cccctttcct ggggtggtgg   6960
tggtggtgtg tagacagggg ggctgaggcc acactctaca taattagcac acgtttgggt   7020
gcacacgcgc agcgtgcctg tacacaagtg cacacacgta tatttagacc actctgtcct   7080
agactgagag tcacatatag aagccagtgg gggtgggggt ggggtcttta aatcaagaaa   7140
aaagcttgga gggggttcccg tcgtggctca gtggaaacga atctgactag taaccacgag   7200
gatgagggtt cgatccctga cctcactcag tgggttaagg atctggcgtt gccactagct   7260
ctggtgtagg tcgcagattc ggctcggatt tggagttgct gatggagaag tcaactgacc   7320
ttaaggtgtg atcatttcgc aaaacatacg tctatcaaat catcagactg tgctgaaact   7380
tacacgatgt tatatgctga ttacatccca gtaaagctgg ataaatgaat gaatggctga   7440
ataaatgaat ggcttgtgcg tccttgagcc ccaaagaaaa caagttacat aaaaatgggg   7500
atgggacaga gagcagggtg acttcataga ttcttttttt ttttgaaaca gagccaatac   7560
atcgaatgac tttataaacc atgactttca aattttgagc atctaatcaa gctctcgctc   7620
tgcagccggg cctcagcttg tttcctctgt gtctcccagc acgggagagg cgagggctgg   7680
tactgcctgt gcccttcctt catttatctg cagggtcgag tggctggtgg ggccacctca   7740
gctgccaact catttactct gaccccgca gccccgtggc cgatggagaa acccggcct    7800
ccaagtggct ggagatgagt ttgtcgcccg catgccctgt tcctggccgc agcgaggagg   7860
accccacccg ctgtggccct gcctcgtgat ggagcctggc cctccgggca ggggcagctg   7920
ctcctgtggc cccaggggca gggtgggggt gggggctttc agcacagcac tttcctggaa   7980
aagtgattct attttcaaac gctggcacaa gactcttcct gatggcagtg cttctaatta   8040
gtctgagaaa acaaatagtt cttccatcag gggaaaaatt ttgattggca gctcgttatc   8100
accctgcggc cccagtggct gagtcagccg gggacacttg cgtcctgccg atcacccagg   8160
ccggcagcct cctgggcctc actctgtacc tgctgcctcc ggcttctgca ttcacccggg   8220
gtaccctcac catggctgca tcgactcagg ccctcttctt tctttgttga aggaatgatg   8280
tgatgaatta attttctttg gccacaccca cgcatgtgaa agttctgggt ccagggattg   8340
aacctgcacc agaaaaggga cccaagccac tgcagggaca atgcctgacc ttcacctctt   8400
accccacagg aggactcctt agtgagtagg tttatgggtc aactaggcta ggctctcttg   8460
cctggatgtg tgatcaaaca ctggtctaga tgacaccctg aagttactta gatgagatga   8520
gtgtttaaat cagaaaactg agtaagcaga ggaacctctc gaatgtgggt gggccgtgtc   8580
tagtcagttg acggccttaa gagaaaagat ggagcttcct tggggaagag gatattcgcc   8640
tccagatctg agctgcaggt tcagctcctt cttcggtctc ctgtctgcca cctgccctgc   8700
agatttgggg ctggccagcc acacagtagt gtgagccaac tccttaaatt aacccctccc   8760
cgacatatat gacacacaca cacgttgtat gtataataca tatatattta cacacataag   8820
gacatacatg tgtgtgtata tatatacaca gacatataca tacaagtaca cacacacaag   8880
gatatacacg ggctcaaagt agagatgcag ccgggcacct gagaggcgcc aggaagggga   8940
gatgcagcgc ctctgcctta acctcccact gggctcttgc ccatctcatc ttatagaaac   9000
ccacggtgcc atcagcacca gctcagaagt ttaaattgag gcattttgtg gaatagcttc   9060
agtctcacag cactatctca gtttctctca agtaaaaaag aaagactaag ctaaaaccat   9120
tcaacctgct tctgtgcatt tattcggcgg ctcacatcct gctgtgcttc aggtgccaag   9180
```

```
gaaaacccat gtctgtcctg acactgggtg ggtagttggg acctgcgcaa ttccagcagg    9240
gtacaaccca ggcctcccct cccttcactg tgggcagggc tagtccttcc cggggacggt    9300
gctggatgcc cacggtgtct cgaagctgct gctgaaactg gctggtccca attcacatgt    9360
gacctctggt tagagctttg agctggagac tggcacgtgc catctgcctc cacgcggacg    9420
gagccacgag ccacggcagc tgccgaccct cggaccccct gcaaggagct cagggcggag    9480
ctcaggagga ggcgctctgt gctctgggaa acctggcaga acaggtcttc agagagttag    9540
acaccctttt ttcaggagag gattttatga gcccagttct tgcatctcct cgaatctaga    9600
aaagcactaa aatccttctt ggtggcgtct gctcctggtg accagcagtg accctccaga    9660
gaccagcagc caccttctgt aagaggggtg ctggttgcat ggccctcccc cccttcaccc    9720
aaatcgcata taccgaca tcccctacg tctttggagc ggtatttcag agctctctga    9780
aatactgcct ctcgggctat agttcttatt ttgcccccaa taaacttaac tctcaactt    9840 caggctgtgc actttttttt caagccaaca gagcgaggct ccttgccctc tctgacttga    9900
attctggtcc tttccttgtg cctcttcctc cattccttag gctataacgg tttaggcctc    9960
tggagctgga gtgggtggtg gtgggggag atgaaggaa ggagaaaggg gggaaggaaa    10020
actattgccg gggctctggc tagaggatgc gcgggctcca gcaagcatga gaagtccagg    10080
ctgggcaacc tgccgcctcc tgcagaggaa actcagcccc tgtctgcctc tgtggccccc    10140
agaggttcat cccatgggaa ccatcttccc tccacctgcc ccttggggta gggtctgcag    10200 cggcccact ttagttttct ctggtgtcaa gtccatgttc aatgggagca ttcctacagt    10260
tacactgggg accccatccc gtccccagcg acaccctttgc caaggtcctc tggaagggc    10320 acgcttccct aaacagtcct caagtgcttc acctttgtta tttcaaaacc tgcatttaat    10380
tttgtttcaa ttgcccaagt cacagtctac agcttaaagt tactatgctg cagggagttc    10440
tgttgtggct cagcagaagc gaatccgact aatatctaca aggatttagg ttcgatccct    10500
ggcttcgctg agtaggtcag ggatctggca ttgccatgag ctgtggtgta ggtcacagat    10560
gctcggatct gggattgctg tggccggcag ctggagctat gactcaaccc ctagcctggg    10620
aacttccata tgccatgggt ttggccctaa aaagcaagca acaaaccaa ccaactaacc    10680 aacaaacaaa aaagccaacc aaccagttgc tatgccgcat aggatccatc tcgcgagacc    10740
cagagaccaa cactgagggt gcacgagggc ttccttgtcc aggttcatga gctccttaca    10800
cgtactgaaa ctacaccatg tgctcaggaa catctatggt atctgatgct atttctggtg    10860
ctgtgctatt taaattcaaa aaatttcctc tatattatga tgttccgaca tcttccaagt    10920
cctttctggc tggggaggga attcccttac tgagttaacc agtccttaga gacagcaaag    10980
gactagtcca ggaacaggcc tgtgatgtgt gaaccaacca atccagagcc agacctcctc    11040
gcggccaccc caggaggcag tattcctcca ccttcatcac ccctgggcca ggtgccacac    11100
ctaggttaga gctgtcagaa ttgttgcaac gagcctgtcc taagcggttg gctctgccct    11160
gctttgtcct tccaatggca accctaataa agacctgac tttggctctc cctccacgcc    11220
tgttctctgc ctcctgacca ctcagggcta ccctgtggcc cttcatcgcg ttccatgtcc    11280
tccaagtgta acaagtttct ctctctctcg tggctgcacc tgactggcca tcttgtaaaa    11340
gagcccagcc taggagacaa gacatttttg cctattccta ccaattttc ctttcttccc    11400 ttcttgcatc cctcattcct tctctccttc ctttcttcaa aagttttggg ccacacccat    11460
agcctatgaa agttcccagg ccagggattg aatctgagca acagctgcaa cctatgccac    11520
```

```
agctggagca atgctggatc cttaacccac tgccctgggc tggggtcaaa cccacacctc   11580
cgcagtgacc tgatctgctg cagttggatc cttagtccac tgcacccag  caggaactcc   11640
taactctttc ttcactgaag tacagttgac ttatgatatt gtgttagtac cttcactgaa   11700
tcaaacttgg gttctctgca tgaagtaaag ccaatccact gacacccagt tttggtgaag   11760
gaaagggcag cgtttttgc  aggtgccaag caaggagtcc aggcagctgg tgcctaaaag   11820
acctgaactc cctgatggtt ttcagggaaa ggtttttaaa gacaggctga gggaggggt    11880
ttggggtgtg tgtgcttgac tctgggacat tcttctgact gatcggtcat gaggtaacag   11940
gcagtcaata tcatcaccct tctggttcca accagaacca gaagcttcca gaagcttgtg   12000
ggaggcatgc agataacttc ttccacatgg tagaggtttg aatagctgca aaacagctca   12060
aaggacatgt ctcagaatat tatctatagt ccttgaggaa gaactgaagg tcctggactc   12120
tgcttaatgg ctaaactatt gttattttgt ctcgcttgac tgttttcctc tgtttatgca   12180
ttttctcact tctctggtta aattgattct ttggaactct gggaaggcat gagaggctac   12240
agttttccta catacaagag gcaggcagag gacatggtgt atagatgggg gtttgtccta   12300
ggaaggctcc atagggtcct gcttggttac agttttaggt ataaagcaga gtggttcagt   12360
attttgtag  atcgcactga ttgatggtta gacaagagcc ttgaaggact gtgataaatg   12420
ggtatttcca cccaccttgg ggcaagagtg gctgccagcg gcaattatgg gtcttctgca   12480
aactgactgc accctcttcc ttctaactcc gtttcctcct gacttccaag catgacacag   12540
ggacagggca ttcagtgaaa acctagcaca gccttctgag aaggcttatt gatgactctt   12600
ctgcatgttg gctgcatcac cagcacctgg cccgaggtga ggtgccttcc tgcccttgcc   12660
aaagccattt ccacattcct tggggacgct ggtgatgatt gtgtcttaaa caaatttgtg   12720
ctcctttttt ttttttttct aattcctaca ccagtccata ctcagtgagg aaagagggac   12780
aaacgaaaag aagaaatgcc agttccctgt tagcgccaac ctggaggagc cccttagatc   12840
ctctaagtca cagtcaacac cccctttccc ccactccccg ctttcaggaa agggggccgc   12900
acggcagcag gatacacagg tggttttttac aacttaacac tatgtgagga ccgtgttttt   12960
atattattat attgtcttct gctccattat ttccaatttc tgcataatca tcccattgcg   13020
tgaacagggc aaatgcactt aattaatacc ataatattgg ctagaactaa tgaaaaatcc   13080
attgtttggg ctatttccct atcataacta ggcctgtgag tcaaatcctc atagtgccct   13140
tttaaacaca cccacaatca cacctgaagg acacatttcc cgatatgcaa tctcttagga   13200
ggcgcggtgc aaaggcttgt gatacttgtt tgatacaatt ttgctttcat aaatattgca   13260
tcagtttcta gcccgcaaag agggtgtcag atgctttctc acccactgtg ttaacaccgg   13320
gattatccat gcttttagtc cttgccaatt caataggtgg aaaaaaagt  catctcgtta   13380
ttataattgg tactgttctg ggccagctaa tggagatcgg gcgtatgatg gtgattatct   13440
tttgaagtca ccatttaaga tgtccttggt ctaaatgttt tatgctgtaa tttgtaactg   13500
gaagatttat aataagctaa tagaaaagac tgaagtcatg caaccaactt cagccggaag   13560
gctgctctct aagacctctt cctttttaact gccattaggg tgaggtgctc caattttgca   13620
tcctgtccaa tgcaatatta tttaaaaaaa cattgtccag gccaacaagg tgggcaccag   13680
agtgacccca aagcaataag tgagagaggc atttgttaat aaaataagac tctcctccaa   13740
caaatatggc agtgtgctat ttctccaaca acgtcgttgc aggcaactcc gtacttgctg   13800
gtttctaaaa gttgataagt gtatttatcc tattgttttg actttgctgt actgtgagta   13860
attttacaga tcactaattt caatgccaca gtctctaagc cgaatgaagt tgctacattc   13920
```

```
ttccaattaa ttaaccaaca gatttaattt cacactacag agctttggaa tagcaactgt    13980
ttaccaaaat taccattgca aataatgaaa ctgactgttt aaagaaccaa catttagtat    14040
tgtcaattaa gtctgggcga aatgttaata aatataacac agtgtgggga accatctgct    14100
ggagcgttag tttgctgaga gccttcgccc cgagcagcct ggtccccaca gcttgggaac    14160
gtgtcctcca agaaagggaa gggtggttgg caacttgtta tacagccact tccatcaggg    14220
gatccgatcg ctgaactaat aacaacaaca acaagtcagc taggttattt cagctttcaa    14280
aatcttcatt gactgcgtag tcggcaatgt gacaagcacc tgatttaata aacttcatgg    14340
ataatcttgc cacatgttcc caagcttctt tcagccttta cccctggcca tgcacaggtc    14400
tgaaacatgt gccaatagca cacagagtca ccccttggtt tccatgagtg attggttcca    14460
ggactcccac agataccaaa gtctgtgaag gctcaagtcc cttaaaatga tgtggagttc    14520
cctggtggct tagcggttaa ggacttggca ttgtcactgc tgtggcttgc atttgatctc    14580
tggcctggga acttctgtat gctgagagcg tagccaaaat aaacccatca aaactcaaaa    14640
caaacaaaca aagctgaaaa aaaggggttc ccattgtggc tcagcaggtt aagaacccaa    14700
catggtgtcc gagaggattc tggttcaatc cctgcccttg ctcagtggct taaggatccg    14760
gcattgccac aagctctggt gtaggtcata gactcagctc ggatcccacg ttgccgtggc    14820
tgtggtgtag gctgggagtt acagctccaa tttgacctct ggcctggaaa ctgacatatg    14880
ccgcaggtgc agctgtgaaa aggaaaaaaa aaaatggtag actatttgca tataacctgc    14940
agcatcctcc tcctatactt caaataattt ctagatttct tataatagct gatagactat    15000
taaggctatg taaacagttg ccagagcttg ccaagatcat gttttgcttt ttgtaatgtt    15060
ctggattttt tttttcccct gagtattttt gatctgtagt tggtcgaatc tgcagatgca    15120
gaacctgctg acatgaaggg ttgggggcat actgtgtcct gtaattgcat cacagaggtc    15180
ttggttgtca acacaaggtc ttttagttgt caccctgcac cacgtgggtg ggctgggatt    15240
tgcttcaatt ttctcctgct gttatcgctt caattgattc ctagtgctgc tgtttattag    15300
ctatgaagca tggagtttgg tataattttc ttagaatgaa ttcccagcag ttggaacacc    15360
gagttccaat gggaattgaa cgtcttagtg cgttgtgctt ctcgccacca cattgtaacc    15420
ctgcttattc ccttgtctgc aacgcccttg ccgttcattt ctttggatgg tgaagttctc    15480
caggatagag aggctttgtt ccatcccagc ccctgcagca catttatctc ctctagggag    15540
gttaggttcc catggaagcc tgagtgatca gagttggtgg gaaagtctgg cttcacttga    15600
gggagatggg ccaatgggtg gttcttcctc cggacaccat ccagaatcct tatctttgag    15660
gacattggtt ctcagaaagg ctatattccc aggttgccct gcctcgctgg agttcaggca    15720
gctggtgagg gtgtggacct ctgtcccctt ggaggatgtg cagacagtgc ttggcagtcc    15780
tcacctgccc ctggtcccac ccttcctgct atcctgcctc tcgtgctaca gacctggatc    15840
ctctctgcct tcgttcctct ggagaggaga ccctctgtct cctggtgaga ggtgggggga    15900
tgataagcca gtgctaggga tgaagaaggg actggcaacc tattcagcct gggacctgtc    15960
ctctctgggg ctccttggag catcaacctg ctctttctgg gcagcccctc tgaaggcact    16020
tggtgctggt gtcctgccct tgctaggtc acctcctggt cctttgccca ggtagatcca    16080
gctaatgaga aaggagccga tgacttcaac ccacgaggat tttccaccaa agccccagag    16140
ctctgcctgg taggaagctc cctcattcct gccctgggct tggtgagggg gaggtgggct    16200
ctgatctggc gccagcctgc gggctctgag cctgaccctg tattgcgatc cctgatatgt    16260
```

```
tctttccctg aactgcttca gtcttcctcc gaaagcctga ccactcctgc cagaagtgac   16320 agcaggggggt gggtggggag gggaggggag tttgccccccc acctcatcag ggcaatgtca   16380
gaaaagcgta gtgacatgcc ctgctctgag gaagggtggc tatgggcgca gaagcagggg   16440
gcgggacctg agatccacag agacggcagg tgggtctttg aaggcatcct ctgcctacgg   16500
gtgggaatac tgctttgaga gatctcagaa taacgaagcg attgttcaga atgatgaagg   16560
gatagttcag aatagaaagc acccgtgtcc actttcctct tacccacagg ggcaaagctt   16620
gcccttctcc tagggtgccc ctccctcctc tcagcaggac agcagccaag cttgggttca   16680
tgggagactc tttcagtggc catcaggtgg ctggggccag tggtgcgggg gatggtgggc   16740
tgccatattt aggaggctta aggggagaga aaccaaaggt gatagatctt gccacaggg   16800 atgcgcccag cccagcggga tggacaagtg tgacgcggag ggcggagttt ctgttgtggt   16860
tcagcggtaa tgaccctgac gagtatccat gacgttttgg gtccgaaccc tggccttgtt   16920
cagagggttg aggatccagc gttgctgtgg gcagtggtgt aggcagcaga ggcagcttgg   16980
atccagggct gctctggcgg tggtataggc tggcagctgc agctctgatt cgaaccctag   17040
cctgggaact tccatatacg gcgagtgtgg ccctaaaaag gaatgtttcc atttttaatt   17100
ctttgccttg aatcagctgg acgttgctaa ttccttcccc tcccagagac cctttctaca   17160
ggtgactccc tgaaaggcct ccctggaagt ggggacacac gtggtgagaa cttgctcgtg   17220
ggccaccatt tcacggggac tcccagcccc cagggagtct atggcatctc tcggtgtggg   17280
cctggcatcg cccctcctgg tctagatgcc cctcgtggaa agctacctca acaccgtgaa   17340
ggcaaaggga catctcccca cctcctcttc catctgctca cccacaggac acgcacacaa   17400
tccatgcctg ccgaggggca ggacagcgcc tggtgggaga cagcaattag caaaataagg   17460
gaacctctgc tccatagact tgacgtcccg atggggacag ccagacacta aacagatcaa   17520
aaaccccagg tagaatgtca ggcactccac gggctgtgag gcaagatgac gcagggtaag   17580
ccgacaaagc gcggtgggca atgcactatc ttatcttagt cttcgctggt agggccaggt   17640
ggaacctgga gaagaagggg agaagtggtc ctggcttcca gaacaaacag gaaagcaacg   17700
tctcagaagc agaagcccgt ctggcacgct gggagggtga gaggctgggg ctgagtgtct   17760
tcatccaacg atggcaggag cagggccacc cgaggacaga gaggggggcgt gctcagatcc   17820 ggctgggtcc tcgtacagac tttgaatctg accctcatga gttgggaagt gattgaagga   17880
tgctgagcag agcagtgatg ggatcttagg tctgtttaga aggaggactc tggcttctgt   17940
gtggacgtga gagcaggagc aggagcaggg gagttcgagg ccatcactgt ggtccaggag   18000
gactggcgga gacttgggac gccggtgaag cctaggcaca gggtgctgcg cgtaaataaa   18060
ggtggtgcca ggcttctgtc tccagggaca aagatcagaa tcacagtctc cagtgagact   18120
cactggaggc agcaggactg gggggctaaa acccaagact ggtgaacgct tatgcttgcc   18180
atgcgtcctg aaacgtccaa gtgcagacca agcaggggtg tccagtctgg tgctgagaaa   18240
gttcaggtga gtggcacact catggcattg gcctcgaaac tgctggtgtt caaggccact   18300
ggactgcagg agggcacctc ggattggaca ctgcaggcag gaggtctgag gacagccagg   18360
ggcactcaat tcccccagag ggtaggaggg atgtgagatg agaatgatga cagtgcacgg   18420
ggcaaccacg tgtggagtcg gcactggtgc tgcacggaca cggacacggt caccctggtg   18480
tcatgttaag gagccgtgac tgtgatgctg tggggggccag tgctgttcta ggccacggtt   18540
atgatgtttc tggactctgc tgttcttggc ggggagttga ctctcaaact gattcatcat   18600 tttatttttgt tttatttttt ttagggctgc acccatggca catggaagtt cccaggctag   18660
```

```
gggttgaact ggagctgtcg ccactggcct atgccacagc cccacagcaa cggcagatca   18720
gagccgcacg tgcgacctat accacagctc atgacaacgc tggatcctta acccattgag   18780
cgaggtcagg gatcccaacc ctcgacctcg tggctgctag ttgggtttgt taccgctgag   18840
ccataacagg aactcctggt tcattatctt ggagctgctt tattatactc ttgttaggtc   18900
ctgtagcatg tgacgaaccc ctcaaattgt tttctaacca ttgtttagtc cgcacttgaa   18960
tgagtcttca gatacgtgga ataagatgca gcggctcgct gccagacact gggagatgag   19020
agttacatcg tggggcactg gaggctctca ctgcggaaca tgagcgttca tcctgcctcc   19080
agacaccaga caccttccc tccaccccgt ggcacgcggc taattcccta aattacatcc    19140
gttaaagcta agagggtatc catcacagtt gcttagaatg atgaggagtt aacctaatga   19200
aaagaaatac cttgccaagc gtggcttgct ctctttggat gccgtgctgg attttttccca  19260
gcttggagtt cctggcaagg cctggctggt tctccagttc cgcatagcag gggagacaac   19320
tgactggggc caagcagcgg ccagcttctt cacagctctg tccagctggg aactgttccc   19380
aggaatgccc gtgctggcct tggtaactca aagactggca tggatacgcg cttctagaag   19440
cagcccagag ggcaagttca cgcctgggg tttgtttggg gtggttcagg ggagctggtc    19500
attcccacgc ccatccccca tactgagccc cacctgctga ccacgtggga acttgcgctt   19560
tcctgttcca tgagtccccc cagccttggc cttcgtagtc acggggtgct agttcactca   19620
cttctgcgcc tggtgaaatg tccctgctga agagccctgg gccctgggca aggtcaagcc   19680
tccttgctcc caggacccca ccatgtgagg tgtctgttgg tgggaccaca gcccctccac   19740
actgagccac gtggggatca gtttggcggt ggagccggca ggccacgact ggccacggtg   19800
atgtttgtaa gcagcagctg tcattgccat cactgttgtc atggtttgaa ggctgcgctg   19860
ggagcgctct cgtgcccatg cctgcagccc acagaccgtc cggggtgggg ccgagagggg   19920
cagaaatgca aaggacgagc cggtctggtt tgttctccat gaggctccat cgccagcaca   19980
gagcagggcg gcggggcagc cttccccaca gatgagaatc tgcagtgaat atattttact   20040
ttgaaaagcg cagactattt ccagaccgga cattctggcc taattggaaa gtgtttcaat   20100
tacttcctgg ctgggagcag tctcttgggt tcttctggat ctgagaaatt ggcttccatc   20160
ttcatttcaa aacccaggca acagggaaga cccagcactt ctgctgctga ggctgagaag   20220
gtcccttact ccattcttct agcagcaagc atggcatgct ggggtccctg agctgtgctg   20280
ctacctctca gctgagcagc atcctcgtcg gagcggacag ctctatgttg ggtgctatcc   20340
ctacttgggt ttaatgggag acattgagat gtgatattta acttgtgggt gtcggacgcc   20400
tgcgcacata gcgtaatac atggatgccc gacaccactt gggggcgctc agaggcgtgg    20460
aggatttctg tcttaagggt gaatggaagg aggagaggag ccttggagct ggaccatgga   20520
ggagccaacg tgaagggagg gacattgggt gaagcatcag gaccagagac gtggccccac   20580
agacctcagc cgcaggccgt gggctggtct gtaaggctgg tcctgaccgg gggtacgtgg   20640
tgcctgatga cccccccatt cccttctgct caccagccac agcaggcagg acctgccag    20700
aaatcagcca gacacgacgc tagaggcccc accggctttg cggagtgggg gaaccgccca   20760
cccagcctgg gcgtggccga gatgctgcct ctgcccgcc cacccacag ccccccccct    20820
ccctccgctt tccctccagc caacgaagcc acctagaacc gggaagtggc ggcccctgc    20880
aggcctgtgg ttccctgtgc ccagtgcccc gcctgcccat cctgtgggaa gctcgttgag   20940
gctcgggtgg agtcgaggga gggactgtcc ctgctctgcc cacaccagct acctgccagc   21000
```

```
actgcctcct ttccccgggt ctagaggaga cagcttctga gagcgcagag atccctgctg   21060
agctgaaatc tgtggtttag gagcttcctt gtggctctgc tgattaagag cctgactagt   21120
atcctagagg acagggttca atccctggcc tctctcagtg ggctaaggat ccggccttgc   21180
ccttgagcca cagagtaggt tacagatgcg gcttggatcc tgcgttgctg tggctgtggt   21240
gtaggccagc ggctatggct ctgatttgac ccctagcctg ggaccttcca tatgctgtgg   21300
tggtccctga aaaaaaaaaa agaaaaaaaa ccccaaatcc ccggggacaa gctctcaaag   21360
agccgactcc atcctgtggt gcccaaggcc cagctcctgc acgggaagaa ggaggacacc   21420
gctccatggc aagaggtcat tgatggtcct taagtgggtt ctactgacct tttttttcatg   21480 gaagactgga agatggaaat gaggtcacct gattttaaac taaggccatg ttggagttcc   21540
ctgtggtgag gtgggctaaa gatccagcac tgccactgta ggggcttggg tcgctgcggc   21600
ggcctgggat ttgctttctg gcctgggaat ttccacatgc tgctgacgtg gccaaaaaac   21660
aaaagcaaaa aatgaagact atatgacagt taaggccccc tccctctctc tctcactcac   21720
acacacacac aggctatttc cagttactga gtgttactaa aatgatgatt cacggcttga   21780
aaacatgtgt ttttttttt tttttaaat cttttagggc tgcacccgcg gcatatggag   21840
gttcccaggc tagggcttta atcggagctg tggccgccgg cctacaccac agccacagca   21900
acgctagatt ctagctaagt ctgtgaccta caccacagct tacagcaatg ctggatcctt   21960
aacccactga gcaaggccag agattgaact cgcaacctca tggttcctgg tcagattcgt   22020
taaccactga gccacgacgg gaactccccg aaaacatgga tatttgaatt gtaatcgata   22080
tatgctaaaa acacagtcat cctggtacgt ttggtacaca gcctcacggg gaaaataaac   22140
acagccgcct cttccacaag gcgcagtgtg tctggagaaa cagaaggttg tctgtgtccg   22200
aaaccgctca tggagggagt gctaaggatt ctcccctctc accctcact tcgccccgag   22260 gagccaggtc accacagtag gtgcccagcc aattcgaggt gggagcagga acctcccttg   22320
gctcctcccg cctgcctggg tgaacctggt ctgagtctgc acctgtgcca gtgacaggat   22380
gctctccaag ttgtgtgcag ctggctcagg gctcacgccc tgcagggagg tgccaggggc   22440
tggggacaac ggggctccag gaggctggga gagggccagg gtgccgtcct gcagggctgc   22500
ccctgaactg gcggggaggc ctctgcctct ggaggatgta gggtcccttt cagcggctgg   22560
aaggtgacaa ggcccaaatg tcacagacag gggccttctg gcccactgct accctctggt   22620
ttcggaacat cggtgtagcc taccccctgg aagagctgga tgagcggggc ttccacgtta   22680
agtgttgaca gtttaatgac tggcagctac ttcgtgaaag cagaggcgag aggagacggt   22740
gacacaaggg cagtgatttg gatccctaac cggatgagat gtggacgggg actcagagac   22800
cctcatgggc tgacctagag ccgggggttt cagtggcagc tgggccagca gactcggggc   22860
tcagctagtg gccccctgctt cactactgtg gcggataagg aactccctgc cccacctctg   22920
tttccttgtc gggaaaatgg gccccctgcct cccagtgatg acgggagcga cgctgtaaaa   22980
ggcattggtg cgactgtgcc acgtcgctcg tcttagcact gaggtgggtc actaaatgac   23040
ttggctgcac acgaaacgga aactttgggc ccgtccttgc ggttccattc gagtcctttc   23100
caagtggagc ataactaaga accaggatgt gtccttggcg ctgatgtcag tttcccaagg   23160
tgacccacac cagctcctgg cactgcctgg cgggatttcc ctaggccctg accgccaggt   23220
ggagagaccc accacctacg tggtgggtgg ggtgagactt gttctcccaa aacaggtgcc   23280
cagaagaagc tacaccccaa ggaatttcgt atggggagtt aggtcactgc ctctctgttc   23340 tgttttagg acaaaagtgc ctacctaaaa aataggccca gtcatggcag gggtcggtgg   23400
```

```
ggggagcggt tgggtgggca ggcaagtttc ttagcagtct cattattttt ttcagataaa   23460
ttttagaatc tgtggtttgc attgatctct atattggttt ggattgaatg ggtatctttc   23520
tgggagtttt ctcatccaga aacataaccc cttgatgcag ctggctgcat taaaacaggg   23580
tatttggggg gatctttgag acgctgatga tttgaaagtg agaggctgct gttacatcac   23640
agaaagcaac attcccctgt attttatttt taatcaaaac ggaatttaaa cttctcacat   23700
cattcgttgg gagtttttag cttgctcttg cttttgtcac ttatttaaag ctttttttaaa  23760 aaagcatttt tgagcctgcc atttcttgga agcaagtgtc aactccattt tggtggctcc   23820
tctgtttcat gagggctgca tgtgagacgg gattgagagg acagctatca gactctgctt   23880
tggggtcaaa ctgcaacaat gcacaagggt ggggttgggg gtgcagtggt agctccaggc   23940
ctgggaggga cacagggtgc catggtgagt cggggcgggg ggaggcaggc atcggcattc   24000
agcaccttga cggcgcgtgc ggccagcgca ccggggaggcc agggtatgtt gaagaaatgc   24060
tgacgtgggc gccacctgtg tttacgagcg gctgccatgg tgaggggcat gcgaggcgac   24120
ttggacgggc tgaaagacag agcagcattg cctgtttcca tctaaagagt aaaattcctc   24180
ccactgagcg gggaggaaga gtgagcaccc ctcccacagg gacactgtag tctctgccca   24240
ctggggatgc tgggacgctg ggctcagctc caggtggctt ggctgatggc tgcaccagga   24300
cacctggcag gagtggacaa atgctggtta ccctcccatt gtccacatct gcttcccgcc   24360
ccctctcctc ctgccccttc agcaccttct cttccacggc tctggggaca ccctgctgcc   24420
ttctgcagct cggggcccag aatagttgcc gctccagatg gctggtgtgt ttggctcggc   24480
gtccctccat ccgcttctgc aaacttgcct tccttcccag ctcgctgaga tgccgcctgg   24540
tgcggggcag ccagcaggct gggagataac cccaccttgg tggccctcct tcccagcccg   24600
ggctctgccc tcagcagtcc aacctgtctt aacatctctg tccgccagcc cttcttgctg   24660
cagcccgagg ggctgcctgg accccggggc tgaccatgcc cctcccggtc ctatttattt   24720
tgtttcctct ctgatcctta cggagggccc tcccatcacc atttctgtcc agtgtgggtg   24780
agaggagatg agggagccat ctcataccta aaaatgataa aaaccaggaa taggggagcc   24840
tttgggcaaa tgtgcatggt tcacaattct ttcagtttat caaaacaggc accattagcc   24900
ctattgcttg cttttttttt tttttttttt tttttttttag ggtcacatcc ccagcatttg   24960
gaagttccta ggctaggggt caattcggag ctgtagctac accacagtca cagcaatgcc   25020
agatctgagc tgcatctgca acctacacca cagctcacag caacgctgga tccttaatcc   25080
actgagcgag gccagggatc gaacctgcat cctcgcagac actatgtcga gttcttaacc   25140
cactgagcca cagtgggctc tctggaatta gtatctttcc aggagggaga ggccggagct   25200
cagtctctgc cagatgagga cacagggaga aggcagccgt ctgccctcag gaagagagcc   25260
catgctgggc actgaccatg ctggagccag catcttggac atccagcccc aggactgtga   25320
gagaacgcat gtttcagcct cccagcctgt ggtgttgtga tggagccaca ggctaagaca   25380
cccctctcag tcctgagtca ctgcaggagg ggctcacaca gaggcacagc cagacgctgg   25440
gacccactgg gggccaaaat agcagtcctg cctcccttag cttaagcaac acggatttaa   25500
gctgggagta tgcacacat gtacacgcct tctcggggtt ttaggagaa ttgggtgagg    25560 tgatggctgc tgtggtcaca gggtcccctt ctacccattc cccctgcccc agcccctccc   25620 caggggctc agaggagcag cctcagctcc agggcggagt cacgatagcc tacctatcat    25680
ggtcatccca ccccgtgggg tgccactcag gagcccaggc ccaggactgt cagccctctg   25740
```

-continued

| | | | | | |
|---|---|---|---|---|---|
| cctcccaggc | acagggatca | gtcagcaatg | gcctcacgac | cccatcgggg | ccaaagagca | 25800 |
| tgagaggtga | ggacatttcc | ttgttttgaa | gggtcggcag | cccaaatagc | ctgtgtgtcc | 25860 |
| ccctgtcctt | gtccttagcg | tttcagcctg | ttggggtagg | ttgtgtccca | ttgcagctgc | 25920 |
| aatggtcctg | ccctgccccc | gacagtgggg | gtgctgagaa | ggccagtggg | gcaggtggag | 25980 |
| acagcattca | gggctgggaa | ctggaccggg | ctccgagagc | cctgtgggca | gaggccactt | 26040 |
| ggcgggggga | tgctgagagg | ggaggattgg | gtgtggggac | gagcaagccc | ggccagatgc | 26100 |
| gtgacatccc | cgacactggt | gcacgtggga | gccgagcacc | gcgtgacggc | tcacgctcgt | 26160 |
| tttctgacgt | tgagtccggc | cagcatttgc | caggcctgag | agtagatgca | ataaagaagc | 26220 |
| agcagcagca | atcaaggcat | tgagtccgtc | cctctttttt | cagatcttgg | agacgctcgc | 26280 |
| ccgttaggaa | cgcgtgctcc | gtggaggctg | gggtctgcgg | gctggatgga | cgccctggcg | 26340 |
| cccctcctgc | gtttccgggc | ccccgaggag | tgagggagcg | agtgtctctg | atgttcagac | 26400 |
| gtcttccggc | tcagtctttc | ccttcctctc | ctcatccagc | tccccactgg | gaaagaaagg | 26460 |
| gtcctttcgt | ttcaggttgt | gggattcact | gaaaaggag | aagagggccc | tgggtctcag | 26520 |
| agcagagacc | gccggagcaa | aagcttgtcc | tggcgtgtgg | ccgtgagtga | tgctgtggcg | 26580 |
| gcgagtggga | gcgtcgcacc | ttgtccccgc | gtgcgcatgc | agttgtacac | acgggcaccc | 26640 |
| ac | | | | | | 26642 |

<210> SEQ ID NO 3
<211> LENGTH: 13370
<212> TYPE: DNA
<213> ORGANISM: Pig
<220> FEATURE:
<221> NAME/KEY: misc_feature
<222> LOCATION: (13303)
<223> OTHER INFORMATION: n means a, t, c, or g

<400> SEQUENCE: 3

| | | | | | |
|---|---|---|---|---|---|
| actgcggcgg | ccgactagtg | attctggaag | ctcggatgat | ggttagcatt | ttaaagcaac | 60 |
| aaagtatttt | aaaattaaag | tgtgacatca | cttataagtg | aactctaaaa | aaggatatag | 120 |
| tgtgttcctg | tcgtggctca | gcagttaacg | aacccaacta | gcatccatga | gcacgagggt | 180 |
| ttgatccctg | gcctcgctca | gtggcttaag | gatctggcgt | tgccatgagc | tgtgctgtag | 240 |
| gtcaaagatg | tggcttgaat | cccatgtcac | tgtggctgtg | gccttggctc | cagctgaagt | 300 |
| tccaattcga | tctctagcct | gggaacttcc | atatgcttcg | agtgtggccc | taaaagaca | 360 |
| agaaattaga | aaaaggatat | aaatgaagtt | atttacagag | tggaaacaga | cccacagact | 420 |
| ttgaaaacaa | acttctggtt | aacaaagggg | acaggttgtg | ggagggaggg | actgggggtt | 480 |
| tgggactggc | atgtgtacac | tgaggtatac | ggaaggactg | gccaatgggc | acctgctgtg | 540 |
| tagcacagag | aactccaccc | aacagtccgt | gatcatctgt | gtgggaaaag | aatctgaaag | 600 |
| agagtggaag | cgtgtgtgtg | tgtctaactg | actcactttg | ttgcacagca | gaaatgacca | 660 |
| taccttgtaa | actgagagcg | gccaagggtt | gaacccgcat | cctcatggat | actagttggg | 720 |
| tttgtaactc | actgagccac | gacaaggatt | cctcattttg | taaataacat | catcagctgg | 780 |
| gtaccacgtc | tctagtagaa | acacactaag | acatccctga | gtgtggctgc | acatgacggg | 840 |
| gatctgacta | cccacttacag | tgactcaagg | gaaaaggata | cgctaactgg | tgccctcaat | 900 |
| ttgctaccag | gagggggtca | gttcatgaga | gtctttctga | gaccaatgct | cttgttttcc | 960 |
| caacaaggta | ttgtgtttcc | cacaacatca | cacatgggac | tcagctgtga | cggaggtgag | 1020 |
| gacttcagct | gtggccccaa | ggcatttagt | gacaaaccca | gtgacataca | gtagccttac | 1080 |

```
attcatgccc tctgagttgc aagcatcatt ctgaggtgag cagaagggaa cccgcggctt    1140
gaactccctc catcacatca gactgactct gcaccagatt gtgtcctggt cttcagctct    1200
tcctttgtac gttcattcat ctgttcaaca aacaaagcac agcctctcct gcctcccagg    1260
cactggctgt ggccacgcag ggtacggaga gcagaggggt attggtgggc aagtgcatgc    1320
ttgagcaatc aaaccaggct aggagggagg gtctgcagag ggagatttgc tgtgagcatc    1380
ctggacacac cccggaccca gcaccccac ctctgcatcc tggatggagc attctggagg    1440
gagcctcttg gacacagcct ggggccatgc attgtgccct ggcctctgct gcccctgct    1500 ggtgacacac tgctctgtgg tgactgagct cctttctcac ctgttcctgg agaatggaaa    1560
cgccataccc ctctctgctg cctttcaagc ccccaagggc agtctcatca gtgacacaca    1620
gcctgtcctc tttaactgtg tagaaaaaaa aaagtgtctt tcctgttaag atggagcata    1680
ttttctccag atctgcctac atttgtttgc tcccaaacat ctgagtgccc ctccctccta    1740
agagtctcgg tgaaacacct cattacagag actagagctg gaggggctc gaggatgtgt    1800 gggcccaagc ccccaccctc acaggctttg cagatgaagg gcgaggctcc cagagaggga    1860
agtgcacttc ggatagccag gggcagagcc aggcgtggga atttcgcctc aggcatttta    1920
acccaggctc ctccaataac cccagtgtct gagtctcccc ttggaaatcc tggggagggg    1980
cccatggctg gagaacgtgg gcttttgtgg gagaatatgt ctacatccct cagcctaatt    2040
ttctgttttg ctgggtttgg gtaccgtttt ccttgcattg ccccttaacc gatattatag    2100
ctttaaaaaa attttttct agtttcattt gtcatcctaa attagaaagg aaatcccaaa    2160
cccaaaagaa aacaaaaaga caacttacag aatgggagaa aatagtttca atgatgcaa    2220 ccgacaaggg cttaatctct agaatatata agcaacttat acaacccaac agtaaaaaag    2280
ccaatcaatc aatggaaaaa tgggcaaaag acctgaatag actgttctcc aaggaagata    2340
tacagatggc cagcaaacac atgagaaaat gctcaacatc gctgatcata agagaaatgc    2400
aaatcaaaac taccatgaga taccacctca caccagtcag aatggccctc attaataagt    2460
ccacaaataa caagggctgg aggggctgtg agaaaaggg aaccctcctg cactgctggt    2520
gggaatgtaa gctggtacag ccactatgga gaacagtttg gagataccttt agaaatctat    2580 acatagaact tccatatgac cccaccatcc cactcttggg catctatccg gacaacactc    2640
tccttaaaag agacacatgc acccgcatgt tcattgcagc actattcaca atagccagga    2700
catggaaaca acccaaatgt ccatcaacag atgactggat tcggaagacg tcgtgtatat    2760
acacaatgga atactactca gccataaaaa agaatgacat aatgccattt gcagcaacat    2820
ggatggaact agagaatctc atcctgagtg acatgagcca gaaagacaaa gacaaatacc    2880
acatgatatc acttataact ggaatctaat atccagcaca aatgaacatc tcctcagaaa    2940
agaaaatcat ggacttggag aaaagacttg tggctgcctg aagggagagg gagggagtgg    3000
gagggatcgg gagcttgggc tcatcagaca caacttggaa tagatgtaca aggagatcct    3060
ctgagtagca ttgagaacta tgtctagata ctcatgttgc aacagaacaa agggtgggga    3120
aaaaatgtaa ttgtaatgta tacatgtaag gataacttga tccccttgct gaacagtggg    3180
aaaataaaat aaaaaaagaa agaaaatccc agaaaaagag tcaagattag cttaaagcaa    3240
aagaataact ttgttttca tgaagtttgc aaactggggt tgaaatatct tctgcttgcc    3300 ttttttttg cttcttaggg ccgcatctgt ggcatacaga ggttcccagg ttaggggtca    3360
aatcagagct acagctgctg acctacgcca cagccacagc aatgcaggat ctgagccatg    3420
```

```
tcttcgacct acatcacagc tcatgacaat gccagatcct taacccactg agtgagtcca    3480
gggatagaac ctgcaacctc aaggttccta gtcggatttg tttccgctgc gccacgacag    3540
gaacacccca tctcttgctt gctttctaat tagattgttt gttttacctt ttagttttga    3600
gagttctcat atattctttt tttttggcca cacctgaagc atgcggaatt catcaggcca    3660
gggacagaac ccatggcata gcagtgacct gagccactgc agtgacaatg ccggatcctt    3720
aacctttgtg ccaccaaggg aatgcctcgt atagtcttaa aaattttttt tattatagtt    3780
gatttaaaat attgtgccaa ttttttgccat acagcaaaat gacccagtca tacatatatt    3840 cttttttaaaa tatcttccat catggtttat ctcaagagac tggatagagt tccctgtgct    3900
atgcagcagg acttcattgc ttttcattct aaatgtaata gtttgcacct acgaacccca    3960
gactcctggt ccattcctct cccatcctca tatattcttt acatgtgagt ttaaaatata    4020
ttctaaatac atgtcctgaa aatgtgcttg caaacatttt cttccaatca gtagttcatt    4080
ttttttatca tcttaacaga cttaatggac ttttacagag caaaagtttt aaacttgatt    4140
aaatccaatt tattcagttt ctgtttcaga gttcccattg tggtgcagca gaaacgaacc    4200
cgactagtat ccatgagaat gtgggttcca tccctggtct tgctcagtga gttaaggatc    4260
tggtgttgcc ttgagctgtg gtgtaggtta caggagcggc tcagatccca agttgctgta    4320
gctccagttt gagacccttt gcctgggaac ttccatatgc cacaggttca gccctaaaaa    4380
gaaaaaaaat ttcgttcatg aatcaggtgt tagttttgca tggaagaact ttttgcgtag    4440
tgctaggtct cgaagattct gtttggttgt agagaagcta agtcagcaaa cacagcagac    4500
acacatcttt tcccgtgggg tttacttccc gggagcagcg gggaggggc ggtaaacacg    4560 agaaataggc agacgtgcag cacatgctag ttggtgagac cttgtaggga aaacaaacag    4620
ggaagtggtg ggggtgtcgg ggagacgctt tcaagcgaag gctgaagaag gcaggcgact    4680
gggctcaggg gaacctgggg agggcatttc aggaggccca cgggacatga aggagatgag    4740
aacacaaagg gaaagagtgt gccatgcaga tgcctcctcc agggtgcctg cgtgctggct    4800
ggcggccggg cggtggaacc ccctccagga ttctcaccca tcgccctgga gaaggccttt    4860
gtgccgggtg cagtggggag ggctccggct ggctgcctcg gtgctggcca tggcccggcc    4920
tgcagggtgg gcacatcggg gttggaagtc gggatccgga ggaactgtgc ctggggtgaa    4980
cagggttgtt ccggggaacc tcaccccctga aggtcaccgt gatgcctctt tcactacccg    5040
ggaggctgac cagcattctc ttggctcctc ggaaaaatgc aaatagtacc aataccattt    5100
tcatccagtt ttaggagaat taattcagtg actgctctca gagaggcttc cccagagcct    5160
ggcaggcggg aatacgcctt aaaagacgtg tgttctcata ggcgtgtggt cgaggggcgc    5220
gggttgaggg tctctgctgg ggtttgttca caggttcctc ttttggtggg agacaggagt    5280
tggccagctc tgtttgtttg tttcttttc ttttcttctt ttttttttt agggctgcag    5340 ggtttgaatc ggagctgcag ctgctggcct gcaccacagc cacagcaact cgggatccaa    5400
gccacatctg tgacctacag cacagcttgt ggcaatgcca gatccttaac ccatgggacg    5460
aggccaggga tcgaatctgc atcctcatgg agactatgtc aggttcttaa cctgctgagc    5520
cgcgatggga actctagtat tagtttctag gtgctaacat tttgtaaaga atttttacac    5580
ttatgtttat gaaagatact atatttttt tggaatatct tcatctggtt ttgataaatc    5640
acagtacttc tggcttctcg taatgactcg ggaagtattc tctccttttc actcttgata    5700
tagtttgtgt agagttggtt tgattcttt taaaaaaatt tggtagcatt tcccagtgaa    5760
gctgtctggg cctagagatt tctttgtagg tttgttttta actacaaatt caattttta    5820
```

```
atagatatag tgctgtttat tttttcttga gtgggctttg gtagtttgtg tcatccatga    5880
atttgtccag tttgtctaaa ctgttaaaat tattgccata aatttgttca taacattccc    5940
tgattatatt caatatctat attaccggaa gtgatgtcac ctttctaatt tctaatgtct    6000
tttttttttt ttttttttgg cttttgcct tttcgccttt tctagggccg ctcctgcggc    6060
atatggaagt tcccaaggta ggggtccaat tggagccgca gccgccagcc tacaccacag    6120
ccacagcaac atgggatctg agcttcgtct gcaacctaca ccacagctca cggcaacgcc    6180
ggatcctcaa cccactgagc aaggccacgg atcgaacctg caacctcatg gttcctagtt    6240
ggattcgtta accactgagc cacaacggga acgccctcta atttctaatg tcagtgtctt    6300
gtttcttccc tctctctttt tctgatcagt ctggttggag cactaatca tattgatttt    6360 ctcaaagaag cagcttttgg cttcatagat tttctgtgt tattttgttt tctatttcac    6420
taattttcac gctgatctgt atgatttttt ccttgtactc actttggttt ttatttactc    6480
ttcttttttt ccagtttctt aaaatggaag ctgaaatcat tgattaaaat cattgattaa    6540
aaataattct tttcaggagt tcccatcatg gctcagcggt taatgaatat gactagaatc    6600
catgagggtg caagttcgat ccctgacttg ttccgtgggt taaggatcca gcattgccat    6660
gagctgtggt gaaggttgca gactcggctc ggatccaagc tgctgtggct gtggctgtgg    6720
ctgtggtcag cagcgcagct ccagttcgac ccctagcctg gaaacctcca tatgctgagg    6780
gtgcagccct aaggaaaaaa aaaattcttt tgagttccac cttggctcag tgataacaaa    6840
cctgactaat atccatgaag atgtgggttt ggttcctgga cccactcagt gggttaagga    6900
tctggcgtgg ccttgagctg cacagaggct tggatctgag gttgctgtgg ctgtagtgta    6960
ggctggcagc tacagctcca attcgacccc tagccaggga tcttccatat gccacagatg    7020
tggccctaaa aaaaaagttc ttttcttaaa aaaccccccc aaacccccaat tcttttctaa    7080 tgtggaggtt cagtgctgta aatttccctc taaacactgc ttcagctgca tcccaagtgt    7140
agatatgctg catattgatt ttcactcagt taaaaatgct ttctaagaag ttctcttgtg    7200
gtgcagtgga ttaaggatcc agctttgcca ctgcagcagc ttgggtcact gctgtggcat    7260
gggtttgatc cctggacagg gaatttctat ctgccgtggg tgcagccaac aaaaaacact    7320
ttctaatttc ttaaaatgtt tctttagtaa atgcttagtt taaaaacatt ttcttcaatt    7380
gttacaagtt tcaggacttt ccagataggg ttctattatt gatttctaat ttaatttcat    7440
tttgtgatca aagaataatt ttttatgact ggaattcttt taaatttgat aagattttc    7500 tcatggccca taaatatggt tcactttggt aagtgttgca taggcatctg aaaagaatat    7560
atattctgct gtcattgagt gttgtgttca aaaaatgtaa tttaggtcaa gttaattgat    7620
agtgctgttc ctgtcctcaa tatccttact gatgatctgt ctactatatg tgctatcagt    7680
ttattaagag agttacgtca aaatccgtga ctctacctat ggatttgtta tatcttcttg    7740
tctatataat ttttacttcg tgtattttga agttatatta gtaagtatga gcatttagga    7800
ttatgttata tcctctttat tagttgacac ctgcacgatt atgacaagat tctctttatc    7860
ccttgtaata gtctttgttc tgaaatcaat ttaatcagat atcaacacgc tattattgct    7920
ttctttaaac tagtgttggc atggtatacc ttttttacata ttttacattt aacttatttg    7980
tgtctctatg tttaaagtag atttccagga agcaatgtac acttgggcct taattttttca    8040 ttctgacaat ctctgatttt taagtgggtt tttggtccat ttacatataa tgtgattatt    8100
gaaacgatta ggtttaaatc tattgtattg ctatttgtct cttctctttg tcctatttgt    8160
```

```
tctttgttct cttttcttct ttctctatct tctcttgtat ctattgaatt tttaatataa    8220
tgccacatca tttatttatg ttgtgacatt ttagtgattt ctttggaatt tatgatatat    8280
gtcttttacg aatcacagcc tgcctttgat caatatcata ccacttcttg tgtggtaaaa    8340
ggaatttgca atagtgtact cccatatcac tttttctgtt ctttgtgcta ttattgtaac    8400
acgtttttct tcagcccatg ttataaattc caccaaattc tgttattatt attgccttaa    8460
acattcaatt atcttttaag atgttttggt taatttttaa atttccttat ttctcatgta    8520
gttaccattt ctgctgcatc cttgacttca aatcctacta aactgaagta tcgaggcatg    8580
aaagaagttg aggaattcac cagaaattct gtttctggag ctagaagga aagtgagatg    8640
cagaatatgc catcagttct tcggggaatg tgtccagaag caaaaaactg tggcttgagg    8700
atgatgtgtt cacacatcat tagtgggtta atactgtgct gcagctcagc cccataagcc    8760
ttgtaccacc tccatgaagt actgcttcta ctaacaacac cgtgaaaatg aacatttgg    8820
ttgtgggagt gtaggacgat ggaaaaacta attatagtgt tctccggggg agcctggagc    8880
cctggagtca tgcttacaat tctagtcgat gtgggattta cttgagttgt ttttttttcaa   8940
aattttttaca cttgatgtga caatagtttt acataatgaa catttgtcaa gggtttcaag   9000
tcacagcttt tagagacttc catctcttct tgaaagaaga cagattttca gagtttttg    9060
aatctcataa cgaggtgggc tggcccacat ggacaattga aaggagcaca tttgtgtatc   9120
actgtttaga agctctgaaa taacaccagg ggctaatgat gttggaattc cttaacaatc   9180
tgaattatca agctgttatt ttgcttcaca acttgtcttt aaaattcata atagtacaaa   9240
agatgcagag ggagaaatag gttaaaatat ctgcatttaa gccgtagtct tgctacattt   9300
aaaaaaaaaa aatgagtgag atttcccacc tgggcaagat ggcccagacc tgtttcttgc   9360
tgctcctccc tgccctggat ataaagtagg ggcagctaga ggagaacttt ggaaggtgaa   9420
aggagggaga tggatggatg ggggacccaa ggactgaaga gcagttcagc agcgggtct    9480
cccaccttcc cactcagcag aagatgggaa tccagacccg aaacctagta ataggaggta   9540
gcctaggtgg gcacatttca ccctcagact gaaaagaaac ccttcccatc aaagcaggtg   9600
agtgggacac ctatgagatt tcttttcaat ctgggggacc cctccagcaa taagtagcca   9660
gtaaggaagc ttctcctgcc ttttggaccc aagtctcccc tcccactaag aaacactgag   9720
cagctggctg gcagtggagg aaagcatcct gtcacaggtg gcctggccca ggaagtccct   9780
tagttgctgc agaacctaga ctcctgtctc ctgctcagag acacgggaca ggcagcatct   9840
ctagctgtat acactgtggt attcagtaag cctcaataag ccttgagtat ataattgcag   9900
taaccaagac agtgtggtac tggggatga tagacacaga tcaatgaaca aaataaagaa    9960
cccagaaaca gacccagaga catgagccca actgatttt aacaaagatg caaaagcaac   10020
tcaacgagga agggagtctt tgcagcaaat ggtgctggag cgactgggca tccacaggca   10080
cgtgcacaca ccacacacac acacacacac acacgaacct tgacctgaac tttacatctt   10140
gtgtgcaaat taactctaaa tgggggcacg gacttaagca taaaatacaa aactacgctt   10200
ttagaaaaaa aagaaactaa tcagaatcta gggccaggca aagtgttctt agacgtgaca   10260
tgaaaatcat gatccgtaaa aggaaaatgg attaattgta cgccaccaag atgaaaaact   10320
tcccctgtga aaaactctgg gaagaggatg aaaaagacca gctgctgcct gggagaaata   10380
tgtgcaaaag ctcaaaagag gacgagtgtc tagaatacgt aaactctcaa aacttagtaa   10440
agaaaccgat gatctaatga caaaatggac aaagggcatg gacgatttac tgaggaggct   10500
gtacagatgg caaatagaca caagagctga tgttcaaatc actggctttc cggaaaatac   10560
```

```
taactaaaac cacaatgagg catcaccaca tacctactag aatggttaaa aaaaaaaaaa  10620
tatatatata tatatatata tattttttt tcttttcagg gccatacccc cagcatatgc   10680
aagttcccag gctagggtg gaattggagt tatagctgct ggtctacacc atagccacgg   10740
caaggccaga tctgagccgc atctgcgacc tacagagcaa ctcatggcaa tgccggatcc   10800
ttaacccact gagcgaggcc agggatcgaa cccacatcct atgggtacta gtcgggttca   10860
ttaccactga gccacaaggg gaactccaaa gtaaaaaata gtgataacac caaatgctgg   10920
tgaggaggaa ctggattacc cacgtgctgc tgctgagcat gtaaaatgaa acagccacac   10980
tggaaaacat tttgtcagtt tctttaaaaa ccaagcgtgc aactaccata cgatctcgta   11040
actacatctc tggacattta tcccagaaa ataaagttat attcacccaa aaccaaaaat   11100
gaatatccaa agacgttttc tttataataa ttacacactg acatagccc aggtgtcttt    11160
cagtgggaga atgcttaagc aaggtaggat gtatccacat catgaaacag ctcagccaga   11220
acaatgaata caccatcgat acacacaact ggaagaagtt ccaaagagtt acgcccagta   11280
actccattta tgtaacattc tcaaaaggat agactcttag aaatggagat tattggttgt   11340
catggttagg gatggagtag ctggtgctgg gaggtatgtg tggcgaatga aagggcaaca   11400
gatggataat ctgaaccacc atggccgtca gtacaggaac ccatacctgt gacaagttgt   11460
ataaaataaa tgcacacagg agcacaagtc aaactgggga gttctgagta agattggtgg   11520
actttgtcat tgtcaatatc ctgctggtgg gattgcactg tggctttgcg agataattcc   11580
attggaagaa actggctgct aagtaagtgg gatctgtctg tctgcgttat ttcttgcttc   11640
ttaacctgcg cattatctcc aggtttaagg aaagagatgc aaaacctgag tggcttcttc   11700
aaatccataa agacatttgg aggaactcta cgtgcttatg ataaaaccag agtttccaaa   11760
ataaaataat aaggacaaaa aacgaggaag agttgctttt cctttagcac atgggacacc   11820
ccaggcgctg tgctaaacac tctccatgcg ttatcttgtt tcatcttcat cactcttttc   11880
aagatttttg cctccttata gaaactgtgt ctccatttat gcaacagtat aggatgctca   11940
tatttgtctt aacgggtggc tctgaggtgt ccaaggaatt gtcacatgtg aggtgcgtag   12000
aacaggtcct gacacacaga tgttgcgcag gtaaaattca gtatcagtac aggaaccttt   12060
tccttgtcca ggtgataatc tctccttctt ctggatgttc atagacaggc cgtcgggcaa   12120
attgttccag aataaggagc ggtttagtga aaaacaaaac ccaaatgtga taagggggag   12180
ctttgtcttc aaataaatgc aaataaagcg tctaaaagaa gccacgaaat atattaaagt   12240
ttcggctaag atcattcagt atggatgagc tgttcctaag ggaatattat ttattttata   12300
agataatttt gaaaataaac tttaaatttt tgatttactg aaaggtcgtg aaggtaatgc   12360
agaggccccc atggcctgcc cctaatttcc tctggtgtta acattgtatg ttattgcagt   12420
aaatttgtat caaccaacgg accagttttg tacatcatt attaatcaaa agcccatact    12480
ttatttttca tcttttattt tttgacggag cctgtagcat gtggaagttt ccaggccagg   12540
gattgaactt gagccacagc tgtgacaatg ctgagtcctt gacctgctgt gccacaagag   12600
aactccaaag gccattcttt aattcttcgt atcaccctga aagcaggaaa taaatctctc   12660
ttgtgataag tagtctccct gtaccaggcg agaaagcaac aggcttatca ccagagaaa   12720
ggaatttaaa gccaacaagg atgtacagac agaacttctc actttactaa tttcctacct   12780
caagtctaaa gttttggct tgtcaattct tcacaaatgt attgtttctt tgtctaaaag    12840
gtataaaaat gcctgctttt gttacttctt tgaacctcat attttaatag accctgtac   12900
```

-continued

```
acatgaaatt aaatttatgt tttgtttatc tcttgtcttt tttttttttt tttttttta    12960
aatttcttgg gctgctcccg aggcatgtgg aggttcccag gctaggggtc caatcggtgc    13020
tctagccact ggcctacgcc agagccacag caactcggga tctgagccgc gtctgcgacc    13080
tacaccacag ctcaggatcc ttaacccact gagcaagggc agggtactaa ccggcaacct    13140
gagggttccg agacaaattc gttaagtgct gctgccacga agggaactcc tcgttgatcc    13200
ctaatggcag agttagctta taagcaccca accgaacgag cgcaacgtgg aaaagactcc    13260
gtcatctacg taaactggcg cgggcattga cccgagcgta cgnccacccc gctagagatc    13320
gtgagggcgt gttggggtcg gggggcgctg agtgcgtcgg cggcgctcca               13370
```

<210> SEQ ID NO 4
<211> LENGTH: 27750
<212> TYPE: DNA
<213> ORGANISM: Pig
<220> FEATURE:
<221> NAME/KEY: misc_feature
<222> LOCATION: (27682)
<223> OTHER INFORMATION: n means a, t, c or g
<220> FEATURE:
<221> NAME/KEY: misc_feature
<222> LOCATION: (27714)
<223> OTHER INFORMATION: n means a, t, c or g

<400> SEQUENCE: 4

```
ctgaggcggc cgactagtga ttcataccag atccttaccc attgagtgag gccagggatc      60
gaacccgaaa ccttatggtt cctagttgga tttgtttcta ctgtgccact acgggaactc     120
ctaggagatt ttcttgagta aatatttttc catatgcttt acgctcttag gataattcta     180
gaagctttaa atgattgctt taaacaatca gcttcccagg agttcctgtt gcggcacagt     240
ggaaacgaat ccaactagca cccatgagga ctaggctttg gtccctggcc ttgctcagtg     300
ggtcagagat ctggtgttgc cgtgagctgt ggtgtaggtt gcagacccgg ctcggatcct     360
gcattgctat ggctgtggtg taggctggca gctgtagctc caattcgacc cctagcctgg     420
gaagctccat aggctgtggg tgcagcccta caagacaaa agacaaaaga caaaataaat      480
aaataactaa acacacacac acacacacac acacacacac aaaagtgcca tcattcctca     540
ctgatcaaca aatccaaagt tgacattgca ctgcgcagga gaggaagtga gggcaaagct     600
ctcacttgtt gctggtgggg gcgtgaactg gcacagtcat tgtgggtgtg cttccgcgat     660
gtctgcattt ccaaatggaa atgggtttgc ctttgaccta caatttcacc tcaccaaata     720
ttcatcttac taacatactt gcacaggtta taagtgatgc cagaaagatg ttaccggtat     780
ccgggttctt gatcacgcag ttgaagaatg accttcgaga acacacaggc agcaagcaag     840
caaagtgttt attacaggaa agcaaatacc tcccagggct gctgggagcg gggagaagag     900
cccctcccac ccccgatctc tattgtcctg tggggttttt ctcccttaa agatggggg      960
taccaacgtg gggtccagaa agatgttttc ctcccgttgg ccttgcccag tttcctatat    1020
cagtgcttgt ccaataggct tttaggggtg gacgtgcccc ataagttta tggtttcttt     1080
gtccttctct ttccttagac tgagtcacct ttcctctcat tccttttctc tcagttgagg    1140
agtgggctag agattaaggt gggggggggca ggaaaggcac atttcgtata gtaaacaaag    1200
cctgtagggg aggcacactt cctatagtaa aacaaggcct gtggggaatg actctctgga    1260
gcccttaagc cacacgtgtc catcagtagc cgtatcagag catgcatcga agcccaggct    1320
cctccacgga cccctggagg tcgtattctg cctcataaag acactcacgg cagcagaatt    1380
ttgggaccag cttgaatgct caggagcaga acactcatta aatgcaaggc ggcacctttg    1440
```

-continued

```
atgtgtgttg aggcaggtga gccccatggt gtgttgtcag gttcagagca ctgtgtattt    1500
catggcctct gttgggccca gtccaggatg gacgtgagaa agacagatgg actttttttt    1560
ttcctgtctt tttaggggtg caccggcggc ctatggaggt tcccaggctc ggggtcgaat    1620
cggagttgca gccattggcc tacgccgcag ccacagcaac gagggatccg agctgtgtct    1680
gcgacctaca ccacagctca aggcaacacc agatccttaa cccaacgagc aaggccaggg    1740
attgaaccca cgttctcatg gatgccagcc gggtttatta acagccacga tgggaactct    1800
gagactgact tttcattatg tacctttttg tagctttaaa atattgaacc tgtacaagta    1860
ttatcatttc cagaaataat atttaaacat gtgttactgg atatgcctga attcctctct    1920
atacctgaac tgccctgctg tatctgttca aattcctggc cctgttgctt ctactcggta    1980
tagttttctc acatctgttt tcatttccat ccatcccttt cccatgtctg cctctggctc    2040
tcctatgagg cccaatttaa aggccttctc acccaccccg atctcctcct ggtatgagtt    2100
cagttctaga cacatgccga ttttggtggc tggggtccat gtctgaatct ggagcttggg    2160
agggatttaa ctaaagatga aggtttggga gtcattagga gctcccgtgg ctgtgttctt    2220
gggccatgag tggactagtg gggaccagaa atgctaggat ttttgtctag gactgagact    2280
cggaactgct gcttctggaa tggaatcggt tgtcaagcgc cgctcctccc agcctccaat    2340
ttcatagaac ttccaaataa ctgcaggagc tgtaaaaaca gggtgaactg catctagcag    2400
gatttcctct gcctgcccat gggaccacag acatgtagtt ccctgaagt taggcgtcat    2460 ccagaaagcc cctcccaggc ccagcactgg gcaggacttg gcagacgaa ggcacttccc    2520 tcgcctcctg agacacccat gagagcttcc acctgaaaaa cacatccatt cctgacacaa    2580
tggctgcgtg atgctccctg aggtcagtgt gggcgccagc ctggaggaaa aagtgaggtg    2640
atgggtctga ccccagtgcc tttgctcggt acggcaaggc tctgacgttt cccagcctgg    2700
atgtgggaag aaggcctggt gcggctgggg gccgaaggtc ctgagggtcg ggacggagcc    2760
actctgagca tggacttcaa aacaggaaat ctgcaggttt gtcctggaag cctattggcc    2820
cctggccgag gggccagaat tccacccctc cccacgagca gaagccctga atctgaaaca    2880
tcagaacaga aggcagtaag gaaagggctg gtgcagcggg gccactggca catctgttcc    2940
cctcggctct attaacacct gctgttcttc agtctgagcc cctcacctcc ccagaagaca    3000
agaaggggtc ggagtccccg gttacgcatg cccattggac cgtgaaggat tgtggtgcct    3060
gttcaaacat caaaccaagg tatttctata tccccataac tcagctgctc ccgtgggctc    3120
cctcgcactg atacaattcc actcagacaa tgcgtgggac aagacagtcg ctacctggtt    3180
ttgggtttca agactgactt ggagttctgc cgaggccaca gtctggaacg cagggctcca    3240
cggtgccaga gaagggacgt ctaagcgcca cacctccccg ctcaggcaga ctccgcttcc    3300
tgggacgcag gtgctcccgt aagagcgctg ctcccagcaa aggggtggga agaggaactc    3360
gagggcgagg aggcagaccg gccctcgggg gatcgtccgg agggaacaca ggccttctct    3420
gttccttcct cggtccggag agaatcctgg gtggggctga aaacttgggg acaggacttt    3480
gggttaaatg cggcggagta atgctcactt ccctgaaccc cctaaaccca cacagaggga    3540
gctgcaggac aaggaggaaa caggaaacac gtctgaagac actcagaggc acctactgaa    3600
gccggaagca ggtgcacttt gcaaagtgga gaaggagaga cctcagggc acctggggg     3660 ccaggctgac aggagacaag gaccccaggg agcagggcg ccaggctca gcaggtgggc      3720 tgtggactgg ccacgcccat gaggggagcg ggggggtcag gggggacctc tagaccgcct    3780
```

```
ggcccctct  cccccaaag   gagacccggg  tgactctgga  gaggctgaag  ggtgaccat     3840
gtggggaggt  gaggcccggc  cactttccct  gccccttcct  ggagtgttcc  ctcctgcagg    3900
aggccggaca  atcccctg    aggaagctgc  caagctagga  ggcaggagca  atggatgctg    3960
acctctgggg  ctccctagc   gaggctatgg  ggccacggcg  ggggcgggg   ggtcaccta     4020
cttgagccac  atctgtagag  ccagactctg  ccttcttgcc  ggagcctcca  gccagtgttt    4080
taatgttctc  cttttaagga  gtcacatgtg  gtccagggtc  agctgacttt  cccagagatc    4140
ctctgtgata  ttgtgattta  taataagaaa  tatatatta   ggagttccca  ctgtggctca    4200
gcaggttaag  agcctgacta  ggaggatgca  gcttcaatcc  ctggcctcac  tcagggagga    4260
tccagcattg  ccatgagctg  tggtgtaagt  tccagacgtg  gttcagatcc  catgttgctg    4320
tggctatggt  gtaggctgga  ggttgcagct  ccaattcagg  tctcctagcc  tggaaacttc    4380
catatgctgc  gggtgcagcc  ctaaataaat  aaataaataa  ataaataaat  aaataatata    4440
ttatattata  tctatatagg  tctttgggaa  ttcccattgt  ggctaagcgg  ttaacgaatc    4500
cgactaacat  ccatgaggct  gtgggttcga  tccttggcct  cgaccagtgg  gttaaggatc    4560
cagcgttgct  gtgagctgtg  gtgtgggtcg  cagacgtggc  tcagatcctg  cattgccgtg    4620
gctctggcgt  aggccggtgg  ccacagctcc  gattcgaccc  ccagcctggg  aacctccata    4680
tgccatgggt  gtggccctaa  aaaatatat   acgtatatat  gtcttcatcc  tgtttatggc    4740
acagagctcc  taaaacccctt  ggaatttctt  aagtgacaag  tgtgatagat  gtgtctcttg    4800
ctataataac  aaagtaaatt  tggaaaagca  tctacagatg  ggggctgttc  gccaggagac    4860
tcagccttgc  aactgagtgg  ttagcgggtt  ggaactctcg  gtccccgtgt  cccccaaacg    4920
gctcaacctc  tgggaatggg  agaggggtta  gaggctgaat  ctgtctctag  tggccaatga    4980
tctaatcaat  catgtctgta  tagtgaagcc  tctaccaagg  ccgccaagga  cagggtttgg    5040
aggccttcca  ggctggtgaa  cgaggggaga  cccggggaga  atggtgctct  gggagaggca    5100
cgcaagctcc  gtgtccgtcc  ccatacccgg  gcccgtgcgt  ctctttcatc  tggaagttcc    5160
agagttatat  ccagtaataa  taagtcaggg  atctatttaa  ttaattaagt  agttaattac    5220
ttttttttgt  ctttctaggg  ccgcatccac  aacctatgga  agttcccagc  ctaggagttg    5280
aattggagct  gcagctgccg  acctacgcca  cagccacggc  aatgcgccag  atccgagccg    5340
catctgcgac  tgtgtccact  gcaggtggca  ctgccacaac  gggagctcca  tccagtaatt    5400
tattaagtaa  atgggtttcc  taagttctgg  gagccgctct  agcaagttga  tgtcaaaccc    5460
aaggaagcag  ggcatcacag  aacctccaat  ttagagccag  ctggtcagag  cccaggtgac    5520
agcctggctt  tcaactggca  tctgaaagag  tgtcgtgaag  agagtcagtc  tcgtggcatc    5580
tgcctctgtc  tccaggagag  agtgtcagag  ttgggtggaa  gtgtaggacc  cccagctggt    5640
gtcagagggt  tatctgaagg  ggtgcctggg  tccccacccc  taaacctgac  acacgccctg    5700
gaagctgggg  atgggaattt  tagcctctga  acggaagaga  cggaacaaa   gtaaaccaac    5760
gacctggagg  accttgagac  agcgggaagg  gtggggcagg  acacagacag  caccagccct    5820
agaattcctg  tgttcagaga  gccagggggc  cttgcgtcca  cgctactggc  tgccttcgaa    5880
ggccagttca  gaaggcaaga  gagatgagag  acacaaacaa  ggcatccagt  gggagggtgg    5940
gggggaagcg  cccctgttca  cggctctggc  ggctgcccct  gcacctgctg  tgtcgcctgc    6000
tgctctgtct  ctgctcttcc  tggcgtgctg  aacacatcct  cagcggactc  tcgcttctct    6060
ctcactgcca  accacctccg  tcggcgtggg  cctctggaac  gcataatatt  tctgttctcc    6120
gcgctgcaaa  gtggaggtag  ataaggggtg  gggactgagt  gttgggtcag  ccaggcacct    6180
```

```
ggcacattga cctggccatt ctcctcccga ggacgcccgg cttgtctgcc accccggatc   6240
ccgtgatggg caccctcttt ttggagcccc aggagggtct ccgggatgcc ttccctggag   6300
cagagttcct ggatggttgg cgggtacctg cctcatttca tgagtgcgcc agattgcttt   6360
ccccgatggc tgaatccagt ttattctcct cctggtggag caggaggggt ctcttttctt   6420
cacatcttag cgagcactgg gcatcatacc cctttctaat gtgtgtgtgt gactctattg   6480
ggttcaacgc gggctctcct ttaaaagctg tgctttatcc tgttaccagt gagggcgagc   6540
atgtctcata gactcactcg ccagctgggc ttcctttcct acaattccca ttcatccgcg   6600
tctgtctgtg agggtttccg acttgcatca gtcgttcctt ggaattcccc gcactctctt   6660
tagagtttta ggtgtggctt catcacttca tgtgcaggtg gtatctgtcg ctgaacaggg   6720
tccttaatat ttttatcatc aaatctaaca tgtcttcacc ttgtggtttg tgcttttatt   6780
taagaagact ttacttactg taaactaaaa actgaaaata gaattaccgt ttgatccagc   6840
aatcccactc ctgggcatct atccagagaa aaccatgact cgcagagaca catgtattct   6900
gatgttcact gcagcactat ttgcaatagc caagacctgg aaacaaccta atgtccatc    6960 gacagaggag tggatcaaga agatgtggtc catatacaca atggaatacg actcagccac   7020
taaagggaac gaaataccgg cattttccta gaaactctca tgctaagtga agtcagccat   7080
acaatgagac accaacatca aatgctttca ccaacatgtg gaatctgaaa aaggacaga   7140 cggaactgct ttgcagaaca gatactaact cacagacttt gaaaaactta tggtttccaa   7200
aggagacagt tggggggggg ggatgcgctg gggttgtggg atggaaatcc tataaaattg   7260
gattgtgatg atcattgtac aaccataaat gtaataaatt cattgagtaa caaaaattaa   7320
aaaagacttt acttattgtt ttaattttaa tttaattttt aattttattt tttttgtctt   7380
tttagggcca cacccatggc atatggaggt tcccaggcta ggggtctaat cggagctaca   7440
gctgcgacct acaccacagc tcacagcaat gccggatcct taacctactg agtgacgcaa   7500
cctcacggtt cctagttgga ttcgtctgca ctgcgccacg tcgggaacgc ctattgtttt   7560
cctgttattt aaggagactt tcttcacccc agtcatgaca acgttctctg ttctcttctc   7620
acaggtttat aattatacct ttttcccatc gaagtttttt ttttgggtgg ccacacttg    7680 tggcgtatgg aagttcctgg ccagggatt gaatctaagc cacagctatg acctactctg    7740
cagctacagc agcgccaaat ccttaaccta ctgagccaca gtgggaactc cccatttaag   7800
actttaatct gcgtgacgtc cacctttgta gatggtgtga cttggggtct ggcttttgt    7860 gtccccatat taggaacaat actgcccatg aagctgtatt tcctgtctcc tctgctttct   7920
ggtggcgctg cctctcctat tgaatcccct acagggccc tttgtctgtc ggttctggag    7980
cagggttggc tgctgtcgct gaggctctga agcaggtctg agtgcttggg aaacggagtc   8040
ctctgtctgc tcctttttt ccaaaatgca cagagctatc tgcagatctc tcctgtcctg    8100
tacgaattct agaacgtgct tgttagcgtc tttccagctg gagttttgaa tgagatggca   8160
gtgaatgtgt agtttgtaca cctgcagctt tacctgtgct tgtgcaggaa tagttcgacg   8220
gcttctcgct ttctctacgg ggccccgggg agccagtggt gtgtctgcct cctgtgtcct   8280
tggccgtcca ggactcatgc acactgcatg ggctgcagaa gggctcacta gcgccttcgt   8340
gggtgaatca cttgaatggt tatgttaggt aacggtgcct gtgaaagtac tctgcaagcc   8400
tggaggcagc acgctgcggg gtaccaagca caggccagta cccgcacggg gttcacgtct   8460 gtccccctt ccctgggca ggtgggggtt ggcttcctgc ccgtatcatg agcgatggct     8520
```

```
ccagtccagg atcccttcga ggacccaagt gaaccctgac acaaacgaag caccacgtgt   8580
gcccagctat gagcgtgtta ttactgaagc tgccgtgaag gtaaaaggtg aggcgaattc   8640
tacctaaaaa acgatcaccg gagggctgat gggaatctga tggcaggtca cttgggcaca   8700
cttcatgtgt tctgccatct gtcttagctc tgttgccatg acaacatcct gctcaaacca   8760
cattgatttc tcacagttct ggaggctgga atctgcaat cggggtgcca gcaggggtgg    8820
gttctggtga gggtcgacag ccaccttcct gctgtgtcct cacatgtcag acagggagag   8880
accgagagag gcggagagag acagagttct ggcgtctctt tttttaataa ggccgccagt   8940
cccttgagat tagggcctca ggcttacgac cttatttaac ctcaatcacc ttcctaaaag   9000
ccgcatatct aaatataggc aattggggtt tcagcttcga cacatgaatt ttgggagaca   9060
cggttcagtc cttagcccca tcctacagca cacggtacag ggagagtaag ggttcccggt   9120
ctgcttgggc caaggcccca ggaccacagg gtccactgcc tcccttgcct ggggaggtga   9180
gaggctggga cttagggcag cagggccctg gcaggtagaa ggaggcttct tcttcttctt   9240
ctttttcttt taattttttt tgccttttag ggctgcacct atggcatatg gaggttccca   9300
ggctaggggt tgaattgcag ctgcagctgc agcctacac cacagccagg gcaacaccag    9360
gtctgagcct catctgtgac ctacagcaca gctcacagcg atgtcggatt cctaacccac   9420
tgagcaaggc cagggatcga acctgagtcc ccatgggtac tagttgggct tgttaccact   9480
gagccacaat gggaactccc aagagaggct tcttgagaga caggcttctt ctctcctgac   9540
cttgagtctg ccggcaggag cttcacagga ggcctctcag agggtctgat ggtgtgtctc   9600
ctgctatttg gaggtggaga ggctgtgggg ggagggcctg ggcaccctgg agccctggcc   9660
cagccagggg agggcaatgc caggggacgc tcctgcacct tccaccctgt ggcctggagg   9720
agcctgaggt gggcgcagga agtggggaga gtaaggcctt ccccagacag ggccgcatag   9780
ggtgagctct gttttgtgtg gggggttggc tggtttaact gccacccgtg gaccaagtga   9840
ttttgtcatc tgagagtgac cagaaaaggc tgggcacaga tgtgctcagg gtagtgacct   9900
gggggaggtg acagtgactg ggtgatggca gcaggacgac atgggccgga gctctaaaat   9960
aactcttctg agagtggggg tggcgggagg ggagctgcat gctgagactt ggggtggggg  10020
ggaggtgcag agcctggcca ggatctctag aaaagctggc agagaggagt gttctggaaa  10080
tagcccaggc caccagttcc cgaggcggag ggatgtggga tctacggtcg cgggagcggg  10140
ggttgtgata ggcccagaag caggatgctc ttccagttcc aggtggatca gagatccagt  10200
gagtcccaga gtagggtgct gtgcggacag agcttgtgga caaatgcgct gtgtttattt  10260
gacacaagtt tgggtcatct ttccaggaaa cccaaacccct gcttcacaca tactgttttt  10320
gtgtgtgtgt gtgtatgtgg gttttttttt ttttttttt ttggatttt aggactgcat    10380 ttgtggcata tggaagctcc caagctaagg ggagctgccg ctgccacagc aacttgcgat  10440
ccgagccgtg tctgtgacct acaccacagc tcacggtgac accacatcct aacccactg   10500 agcgaggcca gggatcaaac ccatatcctc acagatactc gtccggttct taagcggatg  10560
aaccagacgg gaactctgaa atatggatgt tagtggtgat tctagtcggg ctcctagaga  10620
aaagaggatg gagagaaaaa cctctgtctt ctaagagaat agatgccaac aatccggagc  10680
acaggcgggt ggaagacgga ctgtgaggcc tccgatgcaa acgaagaatg tgggttgttg  10740
gaaaccggag ggaggtggtc cctgatacac ggcggccaag accttggcag aatggccaac  10800
gagcgcgctg tggaaagta gaactttggc gtgatggagc tggatgttga gctgaagaga   10860
attctaagcc aggtgtgcat gtgaaggtgt ggccggctct ctcctcactg cttctagtaa  10920
```

```
aaagctagag gaggaagacg aatgaagaag gaattattat tattttttgt cttttttct    10980
ggccatttct agggccactc ccagggcatg tggaggttcc caggctaggg gtccaatcag   11040
attgacagct gccggcctac accagagcca cagcaacacc acatctgagc cgcgtctgcg   11100
acctacacca cagctcatgg caacgccaga tctctgaccc actgagcaag gccagggatt   11160
gaacccgcaa cctcatggtt cttagttgga ttcgttaacc actgagccaa cgacgggaac   11220
tcctgaagaa ggaattattc ggcaaaaaat aaatgaggac ttgaagattt ggaaaattct   11280
cagcctactc gtattgcaaa aagtgagaaa gaatgttctg gagagaccct cagaatgtgg   11340
ctggattatc acttggtaaa gagatcatga aatgatggag gggaagcagt gctgcctgga   11400
tggaagggga cagagctgga caagggagg atgctgaact ttctggattc acaggacgca   11460
cagcaaggcc acgcagacgc agggctgtct cctcttcaag gcctcaaggc aggtggcctt   11520
ggctcagtgc ctcaggggca aggttgtccc catgacaaga aggtgacacc caggatcaag   11580
cctacacatc caggtcacac ccacaccagg ggtcacacca aacccacaca caccaaggtc   11640
accctcgcgc tggactgtcc ggttccccgg ctggcctgtt ttggtccctc ttgagttaag   11700
ggccaaggct ctggcctctc tgggggctgc aggagggtca tgacttgggg gccgcctaag   11760
cactgccagg aaatgtctgg tttcctggaa aagtcccctg tgttctcagg ctgccctctg   11820
gctcttttggc ctcaggaaat ccctgggcc ccagaacagg catcacttga caccaaggcc   11880
ctgagtcacc ctgggtgccc gctcctcccc tcctgggcac ccctttcct ccctcctgt    11940
tcgccaacac tgctgccatc ctctgagctt gtttagaggc gcaaggtggg atccacccta   12000
aaccaggctg gttccagctg gtacctggcg ttcgggtggg ctgttgggag gggttctggg   12060
aaagtgggga cagggaggtg gtgatgtggc cactctggtg tttgctcggt gctctctggg   12120
tgtgcatgga aaccttagcc cccctgccag cccctctgcg cgtctgctct tagatgggaa   12180
caaaccccag actccctggg gaagtggggg atgggacacc agtccctctg ggccgcctcc   12240
ccctgggcag ggtccgccaa ccgaccccac ccactcccct tccccttgag ggggagagca   12300
aaggcatctg gcagggcctg gtgctgaagt ccagccggtt tttccaggac aggggttgagg  12360
gcccccactgg ctgcctaatc ctcagctcag aggaccaggt ggtcatttgc cactcagaaa  12420
actcccatca ctcagcaagc acccgaggggc catggccctg cagcaggtgc acctggatgg  12480
cacccccacc ccccacccc tcccaccccta cctgtctttc tttccctcag cctgtggagg   12540
ttcccgggct aggagtcgaa tcgaatcgga gctgcagctg ccggcctata ccacagccac   12600
cgcaatgtgg gatctgagct ttgtttgtgt cctacaccac agctcatggc aacaccagat   12660
ccttaaccca ctgtgcgagg ccggggatcg aacctgagtc ctcatggata caagtcaggt   12720
tcgttattgc cgagccacaa aggaaactcc ctggaatgtg tctcttagtc aatcactttc   12780
tacaatggaa attagacacg ggtttaactt gggccgcaca ttctctgtca cgatcatctg   12840
cacactgatt tgaatcctcc acgctgcttt ccttctccaa ggaagatttc ccaacactgc   12900
cctggcccat ttttttgtt tgtttttttg tttttgtcttt ttgcctttc tagggccgct    12960
ccctcggcat atgaagattc ccaggctagg gatcgaatcg gagctgtagc cactggccta   13020
caccacagct cacagcaact ccagatcctt aagccactga gcaaggccag ggatcgaacc   13080
cgcaacctca tggttcctag tcggattcgt taaccattgc gccacgaccg gaactcctgc   13140
cctggtcact ctttacctgg gccttttcaca gcaactgtga tctgggccca tctgggccct   13200
gggatctcct tgggcggcgg gcgggagctg attcacagtc tgccttgccc tttggtcagt   13260
```

```
caacctctta aagttgtaca aattcccatc tggaggttcc tcaaggaccc agaaaacttg    13320
tttccatttt aacggattaa ctccccttca ccacgtccag attatttgtc tctacctgtt    13380
ggtccccaga tctgcgaagg ggtggggcct gtctctgtct gcagagaggg accatccctg    13440
cctcctgtga tgacggcccc aaagcctcgg aacacgggcc attggcctcc agagactttg    13500
ggggcctgga tgccaccggg agcccagccc catttctgaa cactgggtaa taagggctgg    13560
attgtgtcct cccaagtctt atgtttgaag ccctaaagcc cagcacctca gcgtgtgacc    13620
tcacttggag acgggtcct tgtaaatgca ggcaatatga ggtcccctg gctcctaagc     13680 caatggctgc tgtccttcag cgggaaattt ggatacagag acacccaggg agaggctaca    13740
tctgggcaga cccctggtga tgcttttaca agatgacgcg tgccaggacg gccagccagc    13800
accagctggg ggacagcggg gatcagattc tcccccacag cctcagaaag aaccagccct    13860
gccaacacct tgatcttggc cttccagtct gggagaggct aaatctctgt tgttcaagcc    13920
acctggtggc tttgttggtg ctttgttatg gaagtcctag caaactaagg caacatctgt    13980
ttagctttat aattttatt tttttctt aatgtacctg tggcctatgg aggttctggg       14040
ttataggctg agttggagct acagctgcca gcctacagcc caggcaccac aacactcatc    14100
cgagccacat ctgagacata ggctgcagcc tgtgaccacg tgggatactt aactggctga    14160
gggaggccag ggatcacacc tgcatcctca cagagactat gtgggattct aacccactg     14220 aaccacaacg ggaactccgt gtttgttcat tctctctttt tctttttcc cttcatttt      14280 ggccactgga cagcacatgg agttcccagc ggtaaggtcc gagctgcaat tgagacccctt   14340 tgtgacccat attgaagctg tggcaatgcc agatcctta atccactggg ctggggcagg     14400
gatcaaaccc gtgtcccggt gctccagagg agccgctgat cgcgttgcgc cacagtggga    14460
actctggcag ctccatattc ttaagctcat ctgcccatga cgatttctat gtactgttac    14520
tgtcacaata gaaactcgaa atcaagagca gatctgcgtt tgggtagagg agtgtgtatc    14580
agtgacgact cagttcccag gattttccct ctcgctgtct ttatggaaat taattaattc    14640
atatatttca ggtccaacta taggtctttt aaaactcaga gttgatttac cacgttgtgc    14700 caattctgc tgtatggaac tttaatttga tcgaaaaatt ccaataatc aaagatcatt      14760 tactaatcaa ggacccatca ggcgccttgg aaattacatt tcagccgact atagccacag    14820
gcttactgca gacgccgcag atctgtcggt gtgactatac tgcttgcagc ctggtttgac    14880
agtacaaacc gattttttta aaagtaaag ccattagtta tgataattca atttggttga     14940
acacatgatt acattctcac agcactaaac gtttagtgga aatgatagtg acgcataaaa    15000
ccaggatagg aaatttaaga tgttcaaatt aatttgattt attaagagga ataaacaca     15060 acttgcttca ccgctgtgtt acaagaaggt caacggcaat attttatatc aaattactgg    15120
ccccgctaaa tttgtatcag gatgaacgga gacatggaac attaaatgaa ttattatttt    15180
tttggtaatc gccccccaaa aaatccttgt ataattcctc aatatttca gagcacgctg     15240 acatttaaaa aatcttgttt aaatcaagaa aaactaatgt ggaaataaaa taaggacttg    15300
aattaaaaaa aaagatcttg ttcaaacatc ttgatatttt aggggttttg gagattttc    15360 cttttcatcc ttaactaatc gcatttcttt gctcctcgtc ctgtagctaa gcaacagcat    15420
ctcaagtcag ggttggtgga ggcttcagtt ccggttgccc ctctgagatg gagtcccgcc    15480
ttccagagtc cgtgggattt tccttaaaga gtcagcatat gtgaacccaa agcactacaa    15540
ggttttaatt tccttcttcg aggccttctg taagagccca tcaggatcta ttaaccaata    15600
caaacagatt ggctttcaaa acgtgaggtt cgttgattct cttgggcagg ggacacatcc    15660
```

```
tttaatcgat tttctcctat gttcccaaga ctggctaaca gccaagggca gggacctaag   15720
ggacacactt ttctcccccc tcccccccca tttttttttt ttttagggcc acacctgtgg   15780
cttatggcaa ttcccaggct aggggttgaa ctggagctgc agctgctggc ctacaccaca   15840
gccacagcag tggcagatgt gagctgtgtc tatgacctac actatagctc atggcaaagc   15900
cagatcctta acccactgag caaggccagg gatcgaggct gtgtccttaa ctggctgagc   15960
cacagtggga actcccagag tgtgcacgtt tgaaacgtgt ctgtgctgca ccattttcaa   16020
acatttactt tggttcttaa ccaaacaatg gcttgggaac ggatgccacc atcccggggc   16080
cccagataaa cacccacggt tgttgcctg aggccccact gctgaggctc cttggcagct    16140
cacaccgcag agctgcggaa tgagaatttt gcacagtcct tttcatcttg acagtatcat   16200
tcatttactt ctataaacat catttgttca cttatgttct tgtttcctcc accagcgcag   16260
aaaggaagag aaggagtcac agtgtctagt gggttcatag ctgccactcc catattctga   16320
gaatttcctc tgagaacaaa tctattgttt attgagaaaa ccaactggaa agacttcctg   16380
gtaaaacatg gtacaatgaa cccagatctg agactctccc ttccccaatt cctgatgaga   16440
ttaataaaca gaaaattggc aaaaaaaaaa aaaatctca ctatctaaga gagaaaatgg    16500
tacaaatttg tgctgcagca tttgaaaata ggagtcaagg aaaacaggag aagattctcg   16560
tgctgcatct caggcctcca caacgcccca gagactatac tgggaaaagg agagaaaaca   16620
caattctgat agttttcaaa taaattccct aatttgggga gacgtggaca gagggtgggt   16680
gtacagcctg gagagaagtt tcaagaagcc ctcaagcttg ggaacgctta cctaccgctg   16740
tggaatagca agatctcagc agaggcagga atgattacca gggtctgaca ttttcgagaa   16800
ttccatgctg agttaaagga aatgcccaaa caagtgccct gctgagggta cacatgctcc   16860
cccgagtaaa agcgtgacat ttagtgcaat ctcaggaaag acagcagaat ttagaaaatc   16920
caataaagtc tggtagagca agatgaaagg gaaactttag agcacgtaat atcatgtttt   16980
atataacaac aaaaaaaact aggaagtaga atatacacag ctaaatttca gctaattctt   17040
ccttggggtt tcctgctcag gccctgtgg gggcttctcc ctgtggctgg aggaagacct    17100
gcactacacg tgctctgcgc cttgtcctct gcctggtttc tcagatcctt cctcccccag   17160
gaacacccct cttccctctg cttcccagcg tccccgccgt tttgtttcta aaggccaccc   17220
ttggcctctg tgccttctct gttgctcctg gccactgtca cctcattgag ggagcaggat   17280
ttcctgtctc tggttgtact ccagtgacat ggaaagaatt ttactttctt ggtccttgtg   17340
agggagatgg ttataaggga cacagatggg tcctggtgac ctctggtcgt gggtgaccag   17400
tggccaagcc tttggagaaa cggaagaagc tgctggaaga caggagaggg tgggaaggaa   17460
ttgggggtct tcagaaaata tcagcaggtg atgggagacc ctgagatgcc tggaggttcg   17520
agggaaccag gcgtggaggt ccctgcaaac tggggtgggg agggtggggg gcggggtttt   17580
ggggatgagc agggatggtg gaaagacctg gaaacctccc tgtccattga gaggcctcga   17640
gtcaccatgg agacggaagt gaacggctcc ctggagctcc ggttccgacc aggctggcgg   17700
gagtctgccg cagcctctcc cgcagagtgc aacagaaacc accgggcaaa acaaaataca   17760
gtcgcctgag gactcagaag agtcacaaag gctgtaaact gtgaagtcaa atcggagaa    17820 gcacccctca ggaggtgggg gcgggagggg agggggggtta cttcctagct tttctctttt   17880
ctctcacagt ttttacctaa agacaggcct cagctgccga aatggagggg ggcagcaagg   17940
gaggcccgaa tcccaacaaa aaccccgtcc tcctgggcag aggaagcccg aaaggtggag   18000
```

```
ggtttcctttt tctttcttct cgctctttgg acagtgttac ggagcttctc agcagcctgg   18060
tgtagacaac cgcagctccg agagaactcg gcccttctgc tcagggagac caggagaagg   18120
agtcgctgca gggccagggg acgccccgac gggcggtcc  cctccttctg ccgccagccc   18180
ggcaggtgcc ggctgcatcc ccgagctgcg catgcgccgc aaagcccagg ggcccgggcc   18240
cgccccctgc ccggctcggc gggaggcgac gctgcgaccc accgggccgc tcgctcggtt   18300
gactgcttgc aaaataaatc aaagggcatt ctttgggggg gcccgagcct ccgtagtgtt   18360
ccccgcggga tacccacgt  gtccaggatt ctatcccgag cgtgacgctg acacaaagac   18420
ctccgcccgg cgagggggcg gacgcgcggg aggggcgcag cctggggcag accccgggag   18480
ctggcgggtc accgtgcgca ggcctctgga attcgggaac ccggatgagt cccaagaggg   18540
ggccagggcc ccgctgcaca gggccgcggg ctgaggacag ggccggtgcc ccagaccccg   18600
gggcctgagg gggcggtgcc cactgctctg ctctaatctg gggcacggtt tactccccac   18660
ctctttactc taaagctcgc agaagctggg gaggagcga  ggaccacct  gtcttgcttg   18720 attctatgcc ttttacgcgt gagcccgggc caggggcctc cgcccgcccg gtaacccagg   18780
ctcaggaggg cccagctaag tgcttggatc cagagcttc  taggaagcat gtctatgtgc   18840
tgtccgtacg ctttccttgg ccttgcaggg aggcttccaa gatactgtgt gtgtgtgtgt   18900
gtgtgtgtgt gtgtgtgtgt gtgtgtgtat gtcagtgtgc atgcgagtat gtctctgtgt   18960
ggatccgtgt atggctgagt gtgtgcacct gtgtgcgtta tgcacacttg tgggcctgtg   19020
tgagcgtgcg tgtgttcatg tgtgtatcag catgtgcctg catgtgtggg catgtgtctt   19080
tgggtgtgta catgtgtata gggctgtgca tgcatattca tgtgtgtgtg tgtgcaggtg   19140
tgtctgtgtg tgagtgtgca cgtgtgtatc tgtgggtgtg tgaatctgtg tgggtgagtg   19200
tgtctgtgtg tctgtgtgta tctgcctgtg ggttagtgtg tgtgtgccaa gtaagtacat   19260
tatccttgca gtaaacctgt gccctggaat gacctcccct ccccccagct ctggtctgaa   19320
ggtcaaggcc gagcgatgct attggtgggg cagggatgag aagatgctgg ctgaatggag   19380
ctttcacaac ttgggaattt ggtcaagggt gaaaccttcc atgttttttt gaataaaccc   19440
cccagttcac attttctgtg acacctggtg cactgccttt ggtctgttct tgttgtagct   19500
ctggtgcgtg atacacatag aaaatggtaa atgctcgtag gaccagatga gtgactaggg   19560
cttgaggaac agagagcaga actaaagtgt aagaacacag gagtcagggg ggaaaaaagc   19620
atccaggaag caggggggtcc tgcctatgag gagcagaggc ctttgggaac atagggccta   19680
ttcttcctgg ttgaaaggc  agctgtaatc agaaatgcag acagtcagca gctctcgtgg   19740
gaaacaggcg ggctgggctg agaatgcatt gcgtcctggg gcttacctgc cctaagcctt   19800
ggaattcgtg tagttgcaca gatgagagca tgtttaataa accctggttg ggtctgactc   19860
taatttctcc ttggctgggt accttcagg  ttgccgttcc tcttcatctg agtttctgtg   19920
agcagtcact ggtgtatagc agcaaggggt caatggctgg tggatcttgg tcccagaggt   19980
gtgtgaattc cttgactggg ctgtcacccc ttatacagcc tcaaaagcaa tacgcgagct   20040
ttgtgggtac tgcaggcatc catcgtcttg ggtatattca gaatcaacaa tcataatgac   20100
tgagatattt gagcggcggg agcagttatc agctgtttcc agactttcgt tctattttt   20160 aaaagtctct aaaaggaagt acagattttg ctccaccagg gggttcatta aacattttgg   20220
tcagggtggc tgcctgatac aggggtgcta agattttcca tcctgttgct ttaatcagac   20280
atggtattta ccaatggttc acaattactg ctgcattggg tggcagattt cttttgttat   20340
aagcatttgc tcttgacgaa ctgaggaagt cctaagacaa aagcttcttg atgggtcttt   20400
```

```
aagggcccct tttgtgtcag gttcacagac agaatctctt gtctgcaagt gtattttatc   20460
ttgaagggta tgttgggttc tatggaaaaa ctaggacaac ttaaaacaga atagtgcggg   20520
ctaaagatac agtgtgtaag gctctattct taatgctttg gaaattctct tgaatattcc   20580
aagagtgact tatgtttttg aaggatggtt ttataaaaat cttatggttt tggttaactg   20640
atataatcac gtcatgcttt ataccggacc tgtttcctaa agagtttcaa gacagcttaa   20700
aaatagaggc tgttgaaaga gtggatctta ggaaaccgct ttcctggaaa agcaacaaag   20760
atgacaaatc aataagaacc aaccatttta cattttttt ttatggccat gtgcgtggca   20820
tatgggaatt cccaagctag gggttgattc agagctgcag ctgaggtcta caccacagct   20880
acagcaacac cagatccaag ctgtatctgg gacctacgtc gcagcttgca gcaatgaggg   20940
atgctttaac ccactgagca agaccaggga tcgaacctgc atcctcatgg agacaatgtt   21000
gggtccttaa cacactgggc cactttggaa actccaaaac ccaacaattt tagaactcta   21060
gaaatgaatc aaagacacag aacaaacgac aaagcataca ttcaaggaaa aaaaaatctt   21120
ctgaattttc acaagaacag cggggtgtgt ggcagtattc ccacggctcc attctgaggg   21180
gttcccgtgc ggctcagcag gtcgtcactg gagtggctca ggtcactgct gtggcttggg   21240
ttcattccct ggctcaggaa tttctgcatg cggtgggcat ggccaaaaaa ggctattaca   21300
tctgtccttc ctccccagat cagccaacct cggaatgacc atattgagag ctccactaaa   21360
agccccctta gcacagagtc aatagtccaa cttaactgga agtgacctgg aagaaacttc   21420
atctccatgg gacaatctct gcttgatttg actcagagtt cagctctgga aaaaaaacca   21480
aaaccaaacc atatcttatt acagaaaaca atagcaatct gctggtaata ttgtggctac   21540
actggctata atttcagctg aggtgaaaaa agcttggcta aaaattgaag aggaagactt   21600
ggagaaccgc atgaccatag ggaagttcaa aaagcgttgg cacattcctg ggcatgcaca   21660
gtgctgcgtc catgcccagg aaggacctgg gcaatgaggg ctggctgacc tcgagacccc   21720
atgcaagcag gaaatgaacg ctacacctgt cttgtgaact gcctgaagtt ccaagatgtg   21780
cctttagaaa cagatgccct tggccaaggg tggttcaagg cattgaagaa catcttagga   21840
ttgataattg gctgactgct aaatgatact gacccagggt gactcatagg aagcgaggct   21900 taaaataaa aataagagga gttcctgcta tggtgcaaag ggattggtgg tatcttggga   21960
gcgctgggac gcagggtcga tccctggcct ggtacagtgg gttaaggatc tggcattgct   22020
gcagctgtgg cttaggtcct gactgtggct tgggtctgat tcctggcccg ggcacttcat   22080
atgctatagg atggccaaaa aatggaaaaa aaacaacaac ataaagaact aaaaagaaaa   22140
aatgctagca gagagatatc cccacatatt gcagggata cagaatctac agaattaatc   22200
caggaaattc acaaaatcaa gaagcagcaa tgagaacttg aacaaaaata aaacagtagc   22260
aacaaattct atgtgtgagt gtgtgtgtgt gtgtgagaga gagagaagtt gattctctca   22320
tcccagtttc atgactggtc actcagtccc acctctgggt aagggctgca gaagtgcccc   22380
accctctgtt ccccgactcc ctcccccctgc ccctcccccca gccaaatagc aggtggacct   22440
tagtcttgtc ttcccggctc cgggtgggcc caggtgccca ggagctgctc tgcaggtctg   22500
gccagagggc tttctatttg ccttcaaggc aagagggaca cagaggccct ggtgggccca   22560
accttcttgt tccttccttt tcctttgcat tttgcccct gatttccaag gactctgtgc   22620
tttgcatttt ctctgccttg ttctgcctct tccagtctct ctgactcttt ctgcctttta   22680 tttatttta tttttattt ttttatttta ttttattttc ccactgtaca gcaaggggat   22740
```

```
caagttatcc ttacatgtat acattacaat tacatttttt ccccaccctt tgttctgttg  22800
caacatgagt atctagacat ggttctcaat gctattcagc aggatctcct tgtaaatcta  22860
ttccaagttg tgtctgatga gcccaagctc cccatccctc ccactccctc ccctcccat   22920
caggcagcca caagtctctt ctccaagtcc atgattttct tttctgtgga gatgttcatt  22980
tgtgctggat attagattcc agttataagt gatatcatgt ggtatttgtc tttgtctttc  23040
tggctcatgt cactcaggat gagattctct agttccatcc atgttgctgc aaatggcatt  23100
atgtcattct tttttatggc tgagtagtat tccattgtgt atatacacga cgtcttccga  23160
atccagtcat ctgttgatgg acatttgggt tgtttccatg tcctggctat tgtgaatagt  23220
gctgcaatga acatgcgggt gcatgtgtct cttttaagga gagttttgtc cggatagatg  23280
cccaagagtg ggattgcggg gtcctatgga agttctatgt atagatttct aaggtctctc  23340
caaactgttc tccatagtgg ctgtaccagc tttcattccc accagcagtg caggagggtt  23400
cccttttctc cacagcccct ccagcccttg ttatttgtgg acttattaat gatgccatt   23460
ctgactggtg tgaggtggta tctcatggta gttttgattt gcatttctct tatgatcagc  23520
gatgttgagc attttctcat gtgtttgctg gccatctgta tcttccctt ggagaacagt   23580
ctattcaggt cttttgccca ttttttccatt gattgattgg ctttttttgct gttgggttgt  23640
ataagttgct tatatattct agagattaag cccttgtcgg ttgcatcatt tgaaactatt  23700
ttctcccatt ctgaaagttg tcttttttgtt ttcttttggg tttcctatgc tgtgcaaaag  23760
cttttccatt tgattaggtc ccatgggttt attttttgctc ttatttctgt tgctttggga  23820
gactgacctg agaaaatatt catgaggttg atgtcagaga gtgttttgcc tatgttttct  23880
tctaggagtt tgatggtgtc ctgtcgtata tttaagtctt tcagccattt tgagtttatt  23940
tttgtgcatg gtgtgagggt gtgttctagt ttcattgctt tgcatgcagc tgtccaggtt  24000
tcccagcaat gcttgctgaa tagactttcc ttttcccatt ttatgttctt gcctcccttg  24060
tcaaagatta attgaccata ggtgtcaggg tttattcctg ggttctctat tctgttccat  24120
tgatctgtct gttttgatac cagtaccaca ctgttttgat gactgtggct ttgtagtatt  24180
tcttgaagtc tgggagagtc atgcctcctg cttggttttt gtttctcagg attgctttgg  24240
tgattctggg tcttttgttg ttccatatct ttctgccttt taatctctat ctctctttcc  24300
tcccccaatc cccatctatt ttaaggggtt ggctcatgca atcgtggggc tggcaagcct  24360
gaaatctgca gggcaggagg caggctggag tcccagggag gagctgatgc tgtatcttga  24420
ctctcgaggg gtgtggggag gcaaaaatcc ctctgtctca ggaaacctca atcttttgtc  24480
tcttatgggc ttcaccccgat tagacgaggc tcacccacac tatgcaggga gatctacttt  24540
aatcaaagtc tgcggattaa aatgttaatc gtatcttaaa aatactttccc cagcaagctc  24600
tagactgggg tctgaccaaa aactgagtat gatggtctgg ccaagttgac acacaaaatg  24660
ggccatcaca ggcatacttt gagattgaaa taagagcttt tgtttagggg acgagggggc  24720
gggacttgga gtctctgcag tgctctcttc ttgtccactc tggaaacttc tgaggacaga  24780
ggctccagag agtcacagag aagcaacagc acttttggag gagctcctgg aggcagaggc  24840
aggactgctc ttgggcactg caggccccaa gctttgggga tggccagagg gtgcacggaa  24900
ggcctccttc tctccaggac ctgtgaacca ggagactgag gacctgggat gggcacggcg  24960
agcctccagg ccttgagctg cctgacttgc cgggggcagg tggtacccca gaggtcaggg  25020
tccaccaggc cctccttct  ggaaggaggt caggaacctt cctctctctt tccttttggc  25080
ccctggggat ccttcagggt aaatgtctgc tctgtgtact tgaaactggt gtggaggacg  25140
```

```
tgacagacgg ctgtcagggt gggaaggggt ccaggaatct ataggtgtgg ctgcagcaca   25200
tgtgcccaca aattttctcc atcaatgctt tgagtggaca tttgatgacc aaggagacgt   25260
gcattgtctc aaagaaggcc ctgcaagttt tacttaactc atcacaaact gatttcagtg   25320
attttaaaat agacaaacac ggagacccgt ccttcactga gtgatcaaag tttgtgcttc   25380
tgaaaagggg cacatggaca tatgatgtct cctggcagga agtgctgggg cacagcatc    25440 gcttctgggg tcttactgcc ctaggagcat agacctaatc aaatcatgag gaaacaccag   25500
gcaatgccaa actgaatgac ttctactaag taactgggtg tagtcttcaa aggcgggcag   25560
cgtggtggcg ataggcaggg agagaaggca agctaactgg ggagattccc aggaggtgac   25620
cttgtgaaga ggtctttcct gcatgcaaca tatggtgccg ctgtcttaaa ggaatttaag   25680
aaagaataca cctggatgca tatacacatg atacgtaaca gaagcctgtt cgccttgaga   25740
agatgctgaa taaactggca accctcggca tacggaggtt cccaggctag ggtcaaatc    25800 ggagctgcag ctgccagcct atgcccacag ccacagtaat gcaggatctg acgcaggacc   25860
atataccaca gctctcagca aagctggatc tttaaccaat gagcaaggcc agggatggaa   25920
ctcacatcct catggatact agtagggttt gttaccactg agccacaaca ggaactccta   25980
tttaaagttt gcttttaac ttaaatttaa aagatgttcc ttgaatattg tgttaagtga    26040
aaaaaaaaat ccacatccag aaaaagagta cgtatcatat ttccacaaca ccaacttctt   26100
cttttttttt tttttctttt ttgccttttc tagggctgct cccgcggcat atggaggttc   26160
ccaggctagg ggtctaatcg gagctgtagc cactggccta cgccagagcc acagcaacgc   26220
gggatctgag ccgtgtctgt gactcacacc acagctcacg gcaacgccgg atccccaacc   26280
cactgagcaa gggcagggat cgaacccgca acctcatggt tcctagtcgg attcattaac   26340
cactgcgtca tgacgggaac tccccaactt ctttttttaaa acgttaaaaa acttctaaaa   26400
attaaatata ggtgatttat aatgttgtgc caatttctgc tgtacagcaa agtgacccag   26460
tcatacacat atattcatgc cctttcttac gttatctttc atcatgacat gagaccagtt   26520
tcaaaagtag caggctgatc aggggactca aggatctgtc tgggcctggc ctcactttga   26580
agtggggcag tgcccaggag gagttctagg cagccagggg gctccacagg caggtcttgg   26640
acacactgtg tgtgcacatg ttgtggaaat ccagcaagcc gtatgctggg gagctgtgca   26700
gtgccccccc cctacatgtt actttccaat aaaacatagt taataaaacc caatcctcct   26760 gggatgggt ctgcaaagct ccttgcacgg gcctggaccc taagcttggt gaggaggggc    26820
ttgttcaccc ttttacacag ctctctccaa aggagggaca cttcctgaca ttcacggagc   26880
gcgatgagct ctctacccgt gagctctccc gtttcagcac tggacagctc tgtgtgcttt   26940
ttctaaagga tgccttccat ttctttcata gcaatgtgtt cagtgcccat gatatcttta   27000
gtgcggagag atgcagagat gaatgagcca cagcctgact tggacgcatc acagatatcc   27060
agatgcagaa ggaatgactg gacctcgagg tgggaaggtc acagaagtgg aatgtgtggt   27120
ggagagaact gtgagctggc cacgagagcc gggtatgtgt gctggatctt gcggatgca    27180 ccggaggtag ggagggggtgt tccgggaaga tgagacaagg agattgatgg tctgtggtta   27240
ggaaacctgt ttactgcagc ttaggctgct ccataaagtg ttgcaggaag gcgcagcctg   27300
ttcatgggcg tggactgggg gccctttcat ccccaatcct ggggctgttt tgtggatagg   27360
aagggagggg acagacgcag ggtcagccac gggacaataa ccaggagccc ttgggctctt   27420
tcagcatttt ggggtgagcg gggcaggagc aacttctagg cagggtatcc tgatatttag   27480
```

-continued

```
agacacccac tgggacatcc cgagtgttag gctcaagtta cacacaccac acatttaact    27540
aaaaacaaaa cacttctaga attaataaga ttacaaaatc ataatgggtg gcttttatat    27600
tccttttgca gtattattc ctgcatacaa gttaaaattt gggagagcat tgatacaggg    27660
cctaccaaac tttgcagatt anatattgct ttattgggaa ttttagaaat gtgncaaaaa    27720
gaaaataaaa attgcttata tgttaccatc                                     27750
```

<210> SEQ ID NO 5
<211> LENGTH: 4411
<212> TYPE: DNA
<213> ORGANISM: Pig
<220> FEATURE:
<221> NAME/KEY: misc_feature
<222> LOCATION: (4368)
<223> OTHER INFORMATION: n means a, t, c or g
<220> FEATURE:
<221> NAME/KEY: misc_feature
<222> LOCATION: (4372)
<223> OTHER INFORMATION: n means a, t, c or g
<220> FEATURE:
<221> NAME/KEY: misc_feature
<222> LOCATION: (4375)
<223> OTHER INFORMATION: n means a, t, c or g

<400> SEQUENCE: 5

```
actgcggcgg ccgactagtg attcacaaca caacaaaagc cctagagaaa ccaccaagaa      60
aacagctcaa agatatactt gataaaacga ttgaaaggga gttcccaatg tggcgcagta     120
ggtgaatgat ctggtgttgc cagttctatc cccagcccag tgaagtgggt taaggatctg     180
atgttgccac agctgtggcg tagggcacag ctgcagctcg gatttgatcc ctggccccgg     240
aacaccctat gccaagggtg agaccaaaaa caaaaaagta tgtaaattaa aatcaatgc      300 aatacaatac aatacagcac aaatgaacct acctacaaaa cagaaacaga tgcacagatg     360
tagagaacag acttgtggtt gccaaggagg tggggaggga gggggatggg gagtttagga     420
ttaatagatg caaactgcta catttagaat ggataagcaa tgagatccta ctgtacagca     480
caggcaacta caccctatct tttggaatag aacgcaatgg aagatagtat gagaaagaga     540
aatttttttt tttttttgtc tttttttgcta tttctttggg ccgctcccgt ggcatatgga     600
ggttcccagg ctaggggtcc actcagagct gtagccgccg gcctacgcca gagccacagc     660
aactcgggat ccgagccgcg tctgcaacct acaccacagc tcacggcaac gccggatcgt     720
taagacacct taacatagca gatctagttc agatttatac cagcttaatt ccagtaagat     780
atataaattt acgcctgtga gctccctccc ctgtccttgt ttttatgcta ttattgttat     840
acatgtcaca tccatatatg ttacaaactc agtacactgg cgcaattata gctttataca     900
atcctgtctt ttaaaggcgc taagaaacaa aaggagaaaa caaatgtatt tagagtttta     960
aaaatagtaa catttgtgtt taccatttct gactcttccc atttcctcct gtggagtcaa    1020
attattctct atcttcactt cctgacacca ctgtagtttc attcccactt cctttgtatt    1080
gctgttgtca aaatattat atattttttt gctacagttc caacaataca atttcataga    1140
tattgtttta tgcaatttcc ttttgcttta gccaagagaa gagatgaact ctttggcatg    1200
tgaagtacat cgttgtcttc actggagctc ttatttttgg ctgcacctgt ggcctgtgga    1260
agttcctggg ctggggatcg ggcccgtgcc acatttgcag cttgtgctac agctgtggca    1320
atgctggatc cttaacctac tgcgccacat gggagatttt aactggagct ctttaatttt    1380
tcaagtggat tcaaattatt ttttggtgtc acttttcttt cctgtgatga agtttcttgt    1440
aagacacgtc tgctagcaat gaattccctc agctttttt ttctcagaag gtctttattt     1500
```

```
cacctctcatt ttggaaagat ggttttgttt gatctaagat tcttggttaa cagtgctttt    1560
cccgcagtac tttcttttct ttctcttttt tcttttgtct ttttgccttt tctagggccg    1620
ctcccgcgac atacagaggt tcccaggcta cgggtcaaat tggagctgta gccaccggcc    1680
tacgccagag ccacagcaac tcgggtccaa gccgagtctg cgacctacac cacagctcat    1740
gacaatgtca gatcctcaac ccactgagca aggccaggga tcgaacctgc aacctcatgg    1800
ttcctagtca gatttgttaa ccactgcgcc accatgggaa ctccctcacc gtactttcaa    1860
tgtgacattc tcactgcctt ctgaccttcc ttgtttctga tgtgaagtca gctatcgata    1920
ttattggaga tctcttgtat gtgacaagtc attttctct tgcataattt tgttttaga     1980 attttctctt tgtctttcag tattttgcct atgaggtgtc tgagtgtgtg tctcttactt    2040
tttatcttgc ttggagtaca ttgaacttct tacctgtgta caattttttt catcacattc    2100
tggaagtttt cggttactag ttgttccaaa aattttctg cacctgtaac cctgtcctct    2160
ctttctggaa gtccatttca tgtttgtcgg tgtgcttaat ggtgtctcac atttcgctga    2220
ggatctgtca ttttctttc attctttttc tttctggtct tcggattgcc taaattgtat    2280
taatctactt tcaaaatcac tgatctttt tctttgtcag ttcatactga tgagttgctc    2340
tattgaattt ttccttttgg ctgttgtact tgacaacacc agaatttcta tttggctctt    2400
ttcataattt ctatcttttc attaatattt tctatttgat gaggcatttt ttttaccata    2460
tcatctaatt ctttgcacat gattacttct ggcttttgag cacatttatc atagctactt    2520
ggaagtctta gctgttacct caatatctgg gaggctcaaa gataaaggca attccttttg    2580
cccacttaaa aaaaaaatca aagtgaatat gcatcacgct ttgctgtttc tttgcatgtc    2640
tcatgtttct tggggaaaa attagacttt ttagataata tgttgtagca attttggata    2700
ttgattgcct ctcctcagga gtttttggct ggttttcttg tctgcttgct catttgttta    2760
gtgacttgga tcgactgctt tgatgaaatc tgtatcccct ggagcacgaa gcctctgatt    2820
ttaggcttca gaagacctag ccttgggcat cgccctgacc tctcctcccc gagggctggc    2880
aagcgtcttc actggggttt cctttgacca tttccctggt atcgctgttg aaattcgggg    2940
cagtctgcct atagaggtat cacacccagg tattattctt cgataactgc aagccgattg    3000 ctttttttttt ttttttttt aaatgagagt tgcaatgttt atttcaggtc ctctcggtgt    3060
tttttttttt tttttttctt tttttgcca cataggcagt gtgttggaat tcctgggcca    3120
gggattgaac ctatgccaca cagcagcaac cagagccaca gcggtgaggg tgagaatgta    3180
ggaacctcaa cctgctaggc catcagagaa ttcccatgat ttttttttt taattgacaa    3240 gccccgaaat acatctccac agtctgatcc aattaatatc tccatgctaa gcagggagtt    3300
cttttcctct ctttctttct atctttcttt ctccttcctt ccttcttccc ttcatccctg    3360
cctctcttcc atccagccct ccttccttct tttcttcttt tctctttctt tcgccatagc    3420
agagcatgct gaatttccca gatcgaacct gagctatagc aatgacgatg ctgaatgctt    3480
aacctgctga gccacctggg aactcctagc tggcttcttt tgacgccagt cttttgaggct   3540 tgctccaacc tcaggagggc tcctctcagc tgtctcgttt cctgattttc tctgttaaat    3600
ttctcgctgt tccatttcag ttgctgctct catggatgga gctgccatcc tcttaactgc    3660
tcttcaccaa aatctccatt gtcttcgatg gtacccttag gtgcccttag gcttgaaagt    3720
ccctgaattt tgttctaaat gaagtcagtt ccctcagtga gggccacgga gctgtccgtt    3780
ctcactgctt gtcttttatc ggagaacctc cacgccactg ttttgaggct ggggatcagg    3840
```

```
acagtggctt tcttctctct gagtgatgcg tctgttctgc acgcagggtg atggacatgt    3900
gcagtagcct ctggtctttg cggcttacct ctcttgacat tgaaccctgc cctacgagtg    3960
agcttaggac agtgggtcca atattctcag cctactgccc ctgggtagag ctacggccct    4020
ataagtatgg gttgggtgga aaaagaattt ttcagttaca cgtgtctgga cgagagcttc    4080
tgcagcacag agcaggcgag gtgagaaaag ctggggcctg cccctcctgg ggaatgactg    4140
ttgtcataaa ttgggaagtg gggagaaaag gagccccgtc ttcatgactg cgcctgtcca    4200
gaatatagat tccatctcac caagctctgg ggaaaggaat aggtaagtac tcagatgcca    4260
tagtgtctca ctgctcctcc tgagatttag taggttttcc ttttttgtct tttgtccttt    4320
tttttagggc cgcaccagca gcatgtggag gttccccagg ctaggggnct antcnggact    4380
ggtggctgtg ggcttactca tacccagaaa g                                  4411

<210> SEQ ID NO 6
<211> LENGTH: 11864
<212> TYPE: DNA
<213> ORGANISM: Pig

<400> SEQUENCE: 6
actcggcggc gcctgtgatt agcaatccac agggaaggaa cagtgggacc tgggcttcca      60
ggaacaaata atagcacatc cttcctgaat gttgactgcc tttcggaaac tgtgcctaag     120
tgtcctgtat cctgtgaccc ccacatgatc cttggggcag attctatttt tatggctatt     180
ttgcagatga ggagactgag ttctcagcgt ggttaggtaa cactccgggg tcatcgcatc     240
actcagcgac ttgcaggagc aatcctttt ttttttttt tttttttttg cttttgtct       300
tttgttgttg ttgttgttgt tgttgttgtt gctatttctt gggccgctcc cacggcatat     360
ggaggttccc aggctagggg tctaattgga gctgtagctg ccggcctaca ccacagccac     420
agcaacgcgg gatccgagcc gcgtctgcaa cctacaccac agctcacggc aacgccagat     480
ccttaaccca ctgagtgaga ccagggattg aacccacaac ctcatggttc ctagtcggat     540
tcgttaacca ctgcgccacg acgggaactc cgagaggtgt ttttcccagc ccaggagcag     600
tgctggagaa atacgtgcac gcctgggtgt aaaggacagg gaatgaggct gtgctgttgc     660
gttgtttgca ggatggatag actgggaatg actaaacagc aggaggatta catcccatacc    720
gtggcacacc ccgtagaact tggagcagat gagtcaggag atggaggagg ctgaccaaag     780
ctgatctctc cccctgattc caacaaactc cagacagatc caagaagcag ccacctgagg     840
cctccaagga gccaagagca ggctgaccag ggaagttaga accctctaa caaggctgag      900
gcccatgact tctttttttat cctccaccctc tggctttgac ctgaggtcgg gctgaaccct    960
ggaactttgc caggtggatg gcaagcctcc aggaggaccg cctcattttt agacggacca   1020
tcagacaatg ggaccctgc ttgctggaga tggggaacct tagtctttct ttttcctggt   1080
cttttgtttc cagcccctgct ccaaggccag cctcattggc agagttgtgc cacctggcac   1140
acctcagccc ctaaaaagga caaatctaca ttagtcaccc attgctgtgt cacaacgtag   1200
cagagtgaga caacatgtta cattaattat cctacagggt ttctgagagt tgggaatctg   1260
ggagtggctc agctgggcag gtctggtcca gtgtctcttg aggccgcagt cacactgtca   1320
ggtgactgc ttcatctgaa gctcaacagg tgcatcactt aggatgctct ggctcctcac   1380
cccatgggcc tctccatgct gtcagcatct cctggagtta gtgatctcgg atcacacagt   1440
tatcattgca gaatccagac ttctgctcgc aaacaaatag gaagggaccc agtggcggtt   1500
gaggactgga gggatgtggg tgttgggggct gcatgggtgg gggggcatct agacccaacg   1560
```

```
cttccttctt tacaatgaaa agtccacatg taacaaaaaa gcagcagcac caccaagcgt    1620
tgtatttagg gagagggagg taaattcagc cattaagaaa aggacatttg cagcagcagg    1680
aatggacctt gaggccagca agctaagtga gcagtctgag aaaaacagat actgtccgat    1740
cccatttccc tgtgaaatca aaaaaacccg aacgcacagg aacagagagt agagtggtgt    1800
ttacagggga agcgattggg gagatattga tcaaagcata caaacgtcca gttttaacat    1860
gagtaagttc tggggacttc atttatagca ggtgacagat gatagtcaac aatgccatat    1920
gcttgaggag ctcccactgt ggctcagcaa gttaaggacc caacatactg tctgggagga    1980
tgcaggctcc atccctggcc tcactcagtg ggttaaggat ctggtgctgc cgcaagctgc    2040
attgcaggtc acagatgtgg ctcagatccc gtgttgttgt agctgtgaca taggcctcag    2100
ctgcagctct gactcaactc ctaaactcct atcctgggaa cttccatatg ccacatgtgc    2160
agccataaaa aaagaaaga aaaaccccca acattttttt tttttccct ttaggctgca    2220 ctgctgcata tgaaagttcc caggctaggg gtcaaatctg agttgcagct gctggcctac    2280
accacagcca cagcaacttg ggatccttaa cccactgagc aaggccaggg atcaaacccg    2340
catcctcagg gatcctattc aggttcgtta accgctgagc caggaaggga cacctccaa    2400 acaagatttt ataatttaaa tttgctaaga gagcagagtt taaaagttttt ctctactact    2460 actaaaaaaa atatatctac acatatatca gattattaca ttgtataccct tgcaatatat    2520 tacatatcaa ttatatctcg atacacttgg aaaaaaatac tgaaataaaa actgttagga    2580
aaaagatact aaaattattg tttgcaagag atcaaagcag ttaccttgaa gaggaaatgg    2640
gggcagtggg caggccagtt gttttcatgc ataaatctct ttttactgct taaactgggc    2700
cacatatact tttgataaac atgaaactgt ggggaaggct gtgtgtaggg gctgcacttc    2760
tgtgatggcg aatggatgag gccggccatg ggcttggcct gagaaacccg ctcggggtgg    2820
ttgggggatg gctgtcagtg ttgttccgac ggccaccctg cctgttacac ttgccccgtg    2880
ggggacaggc tgagctcccg gctgaggcgg cccaggatgg gcctgaagga tggttcgcgt    2940
ggttgttctt gccctgtggg cggtggacct ggggctgtgt ggttggtgaa gcagtgagga    3000
tgcctggcca ggcctgccct gggatggctg atggagtgcc gagcctgtgc cctccccgcc    3060
ttctcccggg gaacaccccg cttcccacac agctgggcca gggggctggg gtgcgggggc    3120
ggccttgctt tggagtcaga tctgaaaaaa tatttctggg agaaaaccca gaacatttgc    3180
gtgttggcaa ttccctgtct tttgggcaaa agctggctgt ggcggtagcc gatgccatgg    3240 cttttaaaatg acccttttgc aaaatatctc aaatatgaga ccctgcagtc cagaaaagct    3300
gaaccttctg gaagggccc gggccactgc agcaaatggc gctcttcccc accttctgtc    3360
atagcctggg ctcccggtca tctctgaggc tcctgatgct gccagcccct ccacctgccc    3420
cgagtgagtg tctgcttttg agctccattc gggaggcagg aacacgtctt agggatggag    3480
gcttgcctgt attcttgggg tgcgggaacc ccagctgccc cagcatggat gggggcggga    3540
gaggcaaggg ctaagaggtt agctggtgag cgatctctct gcctgggggt ggtggcagga    3600
aggctcagga cctgatggag acacaagggc tctgggccca ctgcacaggg ctccacatct    3660
gggcaacagc tgggttttgg tagcaggaca acgggtggca tggtctggta ttcagaaagg    3720
gccgcagagg gggtgctggg aaattaggcc ccgtgtgcag gggagggggc aaagcacgtg    3780
accatgacaa tgtggggaaa agctgcggga gcaccgggga ggctgctgtt gcctggggat    3840
gaggagagga gggccgctgg gccaggcgtg gagacaggtc tggttcacta cagggatgtg    3900
```

```
ctaagtggag tcgggaagga cttttgagtg gagggtctgc atgtgcaaag gtcctgggaa    3960
ccaacagagg gcgggtcgaa cagggaccaa gggctggtcc aaccgcaatt cagaaattgt    4020
gcctgtctga gatggggtga gggggtcagg ctggggttcc cagctggcct ctgagggtca    4080
cagcaggctc ccttgtggct ggggtggggg tgctggggct gtggcacaca cctgaggggt    4140
gctggaagcc tcttgatttt cggggctgtc caatcacagc tcgtctgtgc agagatggct    4200
gtccatgcga ggaccccctg ctagtggcgc ctcctgcact ccctaagccc cagggcccag    4260
gcacagatgc tgaacccaca aggccaagtt catgggagct cttttgaaaag agggcatgga    4320 gagggtcccg ccccccggag cctcgcaggg ggcattgggg gggccctcta gggaagtaga    4380
aagcctcctg gggagttccc ttcgtggctc agccagataa gaacccacct agtatccatg    4440
aggatgcaac tttgacccct ggcctcgctt attgggttaa ggatcaggcg tggccgtgag    4500
tggctatgta ggtcacagac acaactcaga tcctgtgttg ctgtggctgt ggtgtaggct    4560
ggcagctgca gctcagattc gacctccagc ccgggaacct ccgtatgctg caggtgcaac    4620
cctaaaaaag aaaaaaaaaa aagtaggtgg gatcatccgt agattgcttc cgaggcaccc    4680
agagaggggg ctgttggagg cagggagctt cacggccagg aattaaagta tttcctgata    4740
gcaaatccac agggaaggaa cagtgggacc tgggcttcca ggaacaaata atagcacatc    4800
cttcctgaat gttgactgcc tttcggaaac tgtgcctaag tgtcctgtat cctgtgaccc    4860
ccacatgatc cttggggcag attctatttt tatggctatt ttgcagatga ggagactgag    4920
ttctcagcgt ggttaggtaa cactccgggg tcatcgcatc actcagcgac ttgcaggagc    4980
aatccttttt tttttttttt tttttttttg tcttttgtct tttgttgttg ttgttgttgt    5040
tgttgttgtt gctatttctt gggccgctcc cacggcatat ggaggttccc aggctagggg    5100
tctaattgga gctgtagctg ccggcctaca ccacagccac agcaacgcgg gatccgagcc    5160
gcgtctgcaa cctacaccac agctcacggc aacgccagat ccttaaccca ctgagtgaga    5220
ccagggattg aacccacaac ctcatggttc ctagtcggat tcgttaacca ctgcgccacg    5280 acggaactc cgagaggtgt ttttcccagc ccaggagcag tgctggagaa atacgtgcac    5340
gcctgggtgt aaaggatctg gcgttgccgt gagctgtggt gtaggttgca gacgcggctc    5400
ggatcccgcg ttgctgtggc tgtggtgtag gccggcagct acagctcaaa ttagaccccct    5460 agcctgggaa cctccatatg ccgtggaagc ggcccaagaa atggcaaaaa gacaaaaaaa    5520
aaaaaaaaaa aaaaaacact tcttttccca tggagattgc taaattgtcc acaaaaaaga    5580
tacatttatt taaggtccaa ccaagatctt tcaacacacc ctaccgacac ttggcattct    5640
ccgtctttgt cattttcaca gtcaacatga atatctcctt attttgattt aagtaccccta    5700 agacttagct cctttctgtg tgcctgtaag ctgtttctat agctctttgc agttctttgc    5760
tatcagtggc ctgtttaaaa attgcacttt tttttttcatt gatttataga agttcttttt    5820
atgtgtatat acactcgatc ttgagagttg tcctatctgg tttattccta gatatcttac    5880
agttttatgg ctattgtgga taggctattt cctacaataa tttatatttg aatattgctg    5940
ttatagaaat agattaaatt ggttttgctt caagccgcac taaatctcc taggttctaa    6000 ttatttttt gatgttcttg gcttttctag gtagagcatc gtgtgtctgc aaatggggac    6060
tgttttgacc cttcctttc caccacgtca tttattgtca gtttctcggc cctgactaag    6120
gtccctgcca taacactgag tgccagctgc gacgtgagcg ggggtgacgg gagacacccg    6180
cccactctgc cagctgctgg tgcctttcat gaccaaaccc aaccaaagca ccaaccaccc    6240
caggatctgg gagtccctcc cgggcagggg actgcccctg gggacatgca gagggccagg    6300
```

```
aatggcctct gtcagagtct ctcctggtga caacagaaac caaacctgtg gaccctctga    6360
ctctgctcgt tcatcacagt tttgtccaga ccccccacag cctccagata ccagggttct    6420
cacaagcagg tgtaagggga cccccacccc caccttcctc agaaacatgc ccttcgccca    6480
gagcctcccc aaggccaagc ctgcatccca cccggcctcc catccagcct cctttggtcc    6540 tgacccgtc tgaccctcca gcccctgctc aggcaggacc agtcaccaaa acctaggga    6600 cccagtgctg gcagcctttg tgggccctct tcctcagcaa gttggggagg agcccaggtc    6660
ctgggcacct gtgcagcctc tccgctccca cagggcacag ggactaggt cagcctgtcc    6720 cctgaccatc atcccctgac cgtcacccac tcccatgctg tcacatggag ggacatgctg    6780
gggactcccc agttcagacc tcagcccaga cttccataa tgacagccac cagtgagcac    6840
ctactgtgtg ccaggttcag ctgagctgtg gattatctca tcccatcctc ccgagaccct    6900
gtgtagacca gaaacccacc gtgtgcagaa gccgcatact tggcaaaggt cacaccacaa    6960
gcggcagagc caggatcgaa cccaggcggt ctcctgcagc accccacgc cttgaccatc    7020 atgcagagtc cacacatagc acacctcggt caaggccacg ttgagggttc cggcaccca    7080 cccctccagg ggaggggcga cctgggctga cctgcgtgga ggagtaagac agaggcagga    7140
ccgcgcatgc tcacagtgag aacggggac cggccaggt gagatgctgt cactcgcggg    7200
ggggatgggt tggacagcat gagcccgaat gtctctccca aggagcacag ccctgggctc    7260
accactcaca cccaggaccg cagaggctct gcagggctgc tttgatgtcc ccgtgtctga    7320
tctctacgca aatctgtcgc ctctgtgggt gtcccactca gctgtcagcc tctgctggtg    7380
tcctgcagct gctccattgt gttgacaatg acctgggaca taaatgcccc acattctaat    7440
tcaattcagt ttgggcccct tgacagggtg gctttaacgt ctccgtctct ggggtttgct    7500
ctgaccccat cggggctctt tgttcttgtc cccgtccca cttgttccct gtgggaaaac    7560
ccagctgcct gtggtttaat atgtgctctc atggagctgc cagcttcctc tcacactcac    7620
ctccaccgtg tgtcctccag cctcctcagc ccccaaatcc ccacagctcc tgcgagctcc    7680
cttaggcttg gactctccac atctattccc aataaagtca gttcccacgg agagagcgca    7740
cgactgctgc tagtggagac ctctgactca ctctcccggg gttgctgggg tcatggccag    7800
tggcccattt tctttcttcc tttcttttt ttttggggg aggggtctt tttagggcca    7860 tggccacggc atatgtaagt tcccaggcta ggggtcgaat cgaagctgta gctgccggcc    7920
tccaacacag ccacagcaac acaggatcct aggcacatct gtgacctaca ccatagctca    7980 cacaaccca gattgctgac ccactgatcg aggccaggga tcgaacctgc attctcatgg    8040
acactagttg ggttagttac cactgcgcca ccatgaggca tgcaccccc gctttatgag    8100 caggagtttg agtgggggca gcagcttctg gtcctctcag cctgcctctc ttggcaggaa    8160
cctccacttt ataggtgagc tgatggggcc cagaatcctc aacatcccgt gtctggcgga    8220
gagcccctcc cctcaccacc agggaggtct ggctgtggga agggagccct ggcttctcac    8280
ccgttcccac ctggaagtta gtctctgtga catggaaatc ccggccgtcc tagggagata    8340
ccacatcaag actccttgtc cataaaatgg atggagggag ctcgcgtcgt ggctcagggg    8400
ttatgaaccc aaccaggatc catgaggatg agggtttgat ccccagccct gctcactggg    8460
ttaaggatcc gggcttccct gcatgagctg cggtgtaggt tacagatgca gctcggatcc    8520
cgtgttgctg tggctgtggt gtaggccggc agctgtagct ccgattcaac ccctagcctg    8580
ggaacctcca tatgtcgcag atgcggccct aaaagaaaa agacaaaatt caattcaatt    8640
```

```
caattcaatt tttaaaaaat aaaatgcgca gacagggaat cccccttgtcc tcaagctagg   8700
ggagagacac acacacacac acacacacac acacacacac gcatgcatac acacaccttc   8760
cctgtgtggg cccgacccct ctagacccga gggaaaaaac ccatgaatgg ggagaaagcg   8820
gggaaagact cacacatgaa acttgagtag actcgcctta ctcctggacc ttgagtctgt   8880
gaacatgctg aatggacatc tagcttcctt cctgctggga cgagtgggga caggtgcccg   8940
gggtcccgcc ggcccccacc ctcagtcctg cacacagcac tgcggctgcc cccaccgccc   9000
ccaggccctc aggccctcga tgcaggtgag ccctccgtc cagactctcc aacacacaag    9060
gcacaggcgc actggtctca gtcaacgtcc caaccaaacc agaggcccct cggcccgaaa   9120
gggtgcctgc ggactggcac actaatgcat gtttctagaa ataagtgcac agaggacgtc   9180
agacggtggg gccggcccta gagacaccct gctcctggtg ccctctgtcc ctcagaggac   9240
gtgccctttg ccggctcctc ttccctccct gccttcaacg ggtacaaagc aagccaccgt   9300
gtgcagggca caggggtgcc atggaagtct ccctccaccc tcaaagtgct gggcacccgc   9360
gggaggcaca gaaccgcagt gagctgggcg cgcagacccc tcccacctgc ccgcagggcc   9420
ctcccctcct gtgaagccct ctatgatatt cccgtctgta agacgggcgt gggggacttg   9480
ccagttctaa gaggccaagt tgggtctctc agaattccct gaaataaagc tggaaacccc   9540
aggggtagca tgagtcttta ttcacagaaa gcagacac ggcagacaga gctcagccag     9600
aacgagagcg ctcgggactc accccaaggt cttgctcaca gggggccgg tcaggaaaga    9660
gcccacccc aattctagcc cctggtcatg acaaagaca ccaggtctca ggctgcgcgg     9720
cggctccatg gaaccctcag cccaaccctg tcttccagat tctctccagg caggatcccg   9780
accaagaggc ctcaaggcct gcaaagcaca gacctacaaa agcccctccc gccctctctt   9840
cccccaggcc cagccaggcg ggaagggggca caccttcca gagggctgct ggggtggagc    9900
cagagtcggg agtgagttcg gagtgggaga tgggcccgag ctggggttag gggccagccg   9960
cagagccagg gctgggggtg gggtcagggc ggggcagggg gcgggagcag tggcaggtcc  10020
gggggtggag ttagggcggg gggcggggtc aggggtgggg gtggggtcag agcacggcct  10080
gggcaggggt caagaccagg aatgggggcct ggggtggaga taggggtcatg gtgggtgtca 10140
gggccagggc tgagggtggg gtcagagctg gaggtgaggt caaggccgga ggtgggggtc   10200
aggcccgggg gtggagtcag ggctggagtg ggaccagggg cagagtcggt ggaaaggcag  10260
cagcagggtc tgggggccca tgggactagg tgctaaggag acctaggaac cccaaaggcc  10320
cagccccggct ggggacagcg cgggcgaagc agcggcaatt gtgcctggca cacaagctcc  10380
agccacagca cattttcttt caccagccca cggccaccca ggcagggtcg ggggcagca   10440
gaagcagcgt ccacgggctc tcccagccct gggggaactt tcttccatct ctccgggcgc  10500
ggcccctcgg actcaccggg ccctcacacc acctgggcgg cgcgtttgct gcgccacacc  10560
accaggccag tcatggcgag ggtcagcagg atgggcacca cgatgagcgg gatgagaatt  10620
tcatccgggg ggtcctgcca ctgttgcctg tccactgagc agttgtggaa atagcgcctg  10680
tggacgccgg tgatgaagct ctgggccagg gggttgggcc agtagcagcc caccacgttg  10740
gtctccacct cagtgcagtt ggtgaagctc tcgtagtacc tgcgaaggca aagggcttga  10800
tggtccagct ccccggccc tcctcgctct ggccccgacc aaccaaccga ccgtctgccc   10860
ggaagtgagg ggcagtcctg tagagccggc cacctgctcc cagtcagggc cccaggccac  10920
gtgggaagag ggcaccctcg tgctcccact cctgttgggc ctgctgggct ggcagggtcc  10980
atccccctgg catccttgcc cagaggttct ctagcctggt gaccgcagcc cctgcatcct  11040
```

-continued

```
ggcacttgcc acctctaggc tcagccctcc tccatctgca cctgagcctc cccccaaag    11100 ttccgctctg cttcacaggc tactgggcac aaacactcaa ttcccccca ggagaccctg    11160 cagagcaggc ccctctgcac agaccccgag gatcacccag cccaacccg ggccctctca    11220 tcttggaaga gaagcagctg agcccagcag ggaacctctg aggccgcgag ctccccgtcc    11280
agacccatgc ccacatccgc atcgcctcac cgtccctgcc cttcgtcatc cacacccggg    11340
acctgctcct tatgaggacg cgtgcgccca gcaccccagc cccggggtcc cagcacttcc    11400
caggtcttcc cagaggacac gccgggcccg gcttcttttct ccaaggccaa aggatgcacg    11460
gggtcaaagc cacttggacc ttgaaggccc tcgataccta gggccaccct gtgggccccc    11520
agagaggagg tgtctctgag gccaggtgcc ggctgcttcc cagtcaagtc cacctgccct    11580
catggagcag gtgggggcg ggggtccct cctctcagaa gtctcctccc ctagccctca    11640
gctgatagga agacatgaga cccacccct gtcgccgccc cagagtcttc ctgcctgtgc    11700
tgatcaaagc tggaaaaggc actcagcaaa ccacccatga ggtggcccag ccagcaggca    11760
ggaggctctg gagagtccct gaggccaacc aagggcgaca gctaccagga cccagagttc    11820
agcccagcag ccccctggcc cgggattagc ggcctctgca ggag             11864
```

```
<210> SEQ ID NO 7
<211> LENGTH: 30535
<212> TYPE: DNA
<213> ORGANISM: Pig

<400> SEQUENCE: 7
```

```
gaaactcttt gcagctgcat tatccacaat atctagaagt agaaacaacc caaataccca      60
ccaagggatg actgggtaaa caaatgcagg atatccttat agaatatgag agttctataa     120
aagatctcta gattctgaat acagactatt ggtttcccat aaaagaatga agtactgaca     180
cctgctacga tacggagaaa ccttgaaaac attatgttca gtgaaagatg ccagtcgcaa     240
aatattgcag gttatatgat tacatctagt caaatctaca gaatagccaa ttctacagac     300
agaggcagag tgcagactag tagtcgctta aggctgaggg ggttggtgga gtggggcatg     360
gctgctagta agagtccgga atgttttttgg ggtgatgaaa atgtcctcat gcagcctgtg     420
gtaatagttg caaattctc tgaatgtact taaaaaaatt gaactatata catcaaatgg     480
gtgaactgta gtactgagtt atatctcaaa aagcttttt aaaaaaatta aaacatttgg     540
gagctccagc tgtgatacag tggattaaga attcaaaggc aggagttccc atcatggctc     600
agtggttaat aaatgcgact aggaaccatg aggttgaggg ttcaatccct gcccttgctc     660
agtgggttaa ggatctggcg ttgccgttag ctgtgttgtg ggttgcagac acggctcgga     720
tcccgcattg ctgtggctct ggtgtaggcc agcggctaca gctcccattc gatccctagc     780 ctggaacct ccatatgcca cgggagcggc ccaagaaatg gcaaaaaaag acctccccc     840 cccaaaaaaa attcaaaggc agcggctcaa gtcactgcag agacacagga tcaatcccca     900
gcccggcgca gtgggttaaa ggatctgcca ttgccaggct gtgccataga tggcatctgc     960
agctcagatt caatccctgg cctgggcact tccatgtgcc gcaggtacag ccataaataa    1020
gtcaataaat aataaaatga agttttttaa acattcaaaa gttgaaagaa agtattacca    1080
gcacactgaa acttcaaata atatttaaga atatccttga gggagaaaga agtaccatgg    1140
aaggagatac tgatcttgac aaaggaggaa gcgcgcgata acgtacgtaa ccaattgtaa    1200
ctacacgcgt cacgtataaa actcgcttct caatagttaa atctccttaa aaggtaactg    1260
```

```
actgtgaaaa ctgaaccaac aaagtatcgt ggatttacaa cttcagttta aataaactgt    1320
atgacagcaa aaacgtaaaa gtcagaatgg aagattctcg tgctatacgt gaattgacat    1380
aatatcactt aaagacggac tgtgagacgt taaaaacaca cactataaac cctaaagcaa    1440
ccaaagctaa taaagaaaag gaggaggcag aggagaggaa gagaatccct cccaaccctg    1500
gacctcagtt tccaggtcta tgccatgaag agaagcatca gaggaactcc aagccacctg    1560
ctggccaagc acttccttgc agtccctgca tccctggggt acccgctagc cagctgctgc    1620
acctgggccc acttgagtcc acagaatcca tgggacagg aggtggctca acagcaggac     1680
aacatgactc ctattagtga caaaaactgt gaccgtgcca cgttcgcaca cacagactag    1740
catgggcact ctctggggc gctgtaaggg agccctggga ggcacagttg ctagcaaact      1800
cgtacatgtt aaatgctaaa catttattga aggtctaagt catttttttt tctttttta     1860 ttactcaaat gaattgatca catctgtagt tgtataatga tcataacaat ctgatttcac    1920
aggatttcca tcccacagcc caagcacatc cccccacccc ccaaactgtc tcctccggag    1980
accataagtt tttcaatgtc tgtgagtcag catctgttct gcaaagcagt tccgtctgtc    2040 ctttttcag attccacatg tcagtgaaag catttgatgt tggtgtctca ttgtatgact      2100
gacttcattt agcatgatag tttctaggtc catccatgtt gcaaaaatg ctggtatctc      2160 attctttcta atggctgagt aatatggtct aagttatttt taagataaaa tactggaaca    2220
ttgattgcta gataagtctg agtttacctt tgtttgtttt atgagaaaaa aaagctaaag    2280
atgtttgggc ttattagaca cacgtctggt gccatttaa agagagaaat tatgctataa      2340
aacacgtatg tttgggggag gtcccttcat ggcacaccag aaatgaatcc aactagtatc    2400
catgaggatt cggattcaat ccctggcctt gctctgtgga tcagggatct ggcgttgccg    2460
tgaactgtag cataggtcac agcaaaatac ttggatcccg cgttgctgtg gctgtggtgt    2520
aggccagcag ctgtagctct gattcgaccc ctagcctggg aactcccatg tgccctggat    2580
gcagccctaa aaaagagga aaaataatt ttatcctaga gctggctgtt tctagatggg       2640
aaaaaaatga gagacaaaca tatagataca gaaagttgtg gaaggtttat gggaaagaaa    2700
attttggaaa agagttctgt gcatggtcag aacggattaa tattagattg aatctaatga    2760
aataaataaa ttttgttatt aaagtaaat acaagactag agcttggttt tctctgttaa      2820
aagaacaaag ttttcatgaa atattgagct gcttttgaca acaggttgca gtttctttc      2880 tctagctaac tttgagtttc ccaaagagcc cctgaggtag ctaagaaaga aatactaaac    2940
taagattatt tggttcttta aaccacatgg aaaacaatat atgaaaaaat ttctgagttc    3000
ccactgtggc accgtgggtt aaggatccaa cgttgtctct gcagtggctt gggttcaatc    3060
ctcagcccag cacagtgagt taaggatcga acgttgctgc cgctgtggcg taggtcacag    3120
ctgcagcatg gatttgatgc ctggcccaag aacttccata tgccatgggt gcagccaaga    3180 aagaaaaaa ttctctggta aagctgtcac agagtatagc tactcatggc atgtatcact     3240
gcttgaagca catgtacaaa gtttgcatga caatttggta attgatatca ccaattacct    3300
gtacttggtt attatgtcag gagtttcccc ccagtgtgaa caccgaggca gacacataga    3360 caaaaagga ggcctaacac caagacatgg tgaacccaga gcaggcagca accacaatca     3420
agggacaagt attgggatca ttaatgcttt cgactgaaag atttgcaatc aaaaggggga    3480
aatgatagaa gaaattttca cagattaagg tatgggggga gttcccatca ggacacagca    3540
gaaacgaatc cgacgaggaa tcatgaggtt gcaggtttga tccctggcct cgctgagtgg    3600
gttaaggata aggcatggcc atggctgtgg tgtaggccgg ccactgcagc tccaattcga    3660
```

```
cccctagcct gggaacctcc atatgctgca ggtgcggccc taaaaagtaa aaacaaacaa    3720
acaaaaaagg tatggaaagg tcatcctggt ttacacatga tttaatggga acttcaggct    3780
aaccaaaaca gcctgtatat tacacataca atgtacatct gctttagcca ctaagggaaa    3840
aaatacagag atgcattttc attactatct tcattgcaat atgtctacta attttcaaat    3900
gtttgtccag gtgctctgac aaagcaatac agaaagaagt aacgttttca taatacaaaa    3960
tattgatact acacttggaa ctgggaactg tttccaactc tgtgtccaca ccccaaattg    4020
aggcaagacc acaccctgtt tcagcaggaa atacctagag caatcgtcac cccgtttctg    4080
caaagattca ggaacagctc aaacaaaaat ggaacgaaaa ccaaactcca ctgccaagtt    4140
tatgactaac ctcgcaatcc aaaattttat tcgctttcat gttccgcacc tgtgcctctt    4200
caggtggggg gatatcaccg aaaaggaagg actgaaacct accaggaccc tgtggggccc    4260
ctcaggtacc aaagcccaga aggctttagt ctcctgagac ctccccagag tcacaaatag    4320
cctggctcaa gaatgaatga tgaggaattc ccatggggcc cagcaggtga gggtccggag    4380
gtgtcactgc agaagtgtca ctgcagaggc tcaggttact gctgtggggc aggttcaatc    4440
cctggcctgg gaatttccac atgctgcgga cacagccaaa aaaaaaaaag aagaagaatt    4500
aatgattgaa tcactgaaag gatgtagaca tgtaatgaca aaaatagcag ttaagcctac    4560
agactggtaa ccgttcaaag agcaaatcag ccatttagtg cttccagaat ctttagttcc    4620
tctctgaaga acatagatag caaggtccgg tgtgtgatgc acattcctga gttgttttgc    4680
agctgttaaa accaccacca gagggaaaaa tctaactgcg tgatgatcag actgcagcca    4740
tgacataagc tgctccattt tgagcagtgc tgctctgcac gtagcccccct agctgcatat    4800
ccttgaagtt ttccttttaaa agctcttgcc ctctgattgg caactcagag atggtttggg    4860
gaggacgcta gtttgcaatc ttcctaggtt gccagcttcc tgaataaagc ctcttccccc    4920
cgaccccacc aaccttgtc tctagaacat tgacttttga gcaatgagca gctaaacctt    4980
ttcagttcca gctctgggtg ggaacacaca tagaagctca gaggcagagc ccagctgagc    5040
agactgctgc tggaccacac tacccccagac cagattcccc cactttacac agcccagagg    5100
cagctcaggg acaagcaggg tgtcaggatc cagagcatag gcagccagca gccctggatc    5160
ctccttctag aggcagcagc ttccagggct gatgtggccc ccatctcccc catgacaaag    5220
cagcatgtga cctgcctgca tctccctcac tcattccgag ccagctcttg gggccctcac    5280
tctgaccaga caagcactgg attgatgtct gctgagaagc tggcctggcc ccatcctggc    5340
tccaagggag ggggatactg ggatggagac aagatgaggt ggcctccaga actgtgccaa    5400
cgtggcccga ggttattaag agagatttct gtcttggtcc ttgccctgtg aggacagcct    5460
tagcttccct cgaaaccaat cagaagattc ctcctccaag ggctttgcat tcgaaggtca    5520
cagatcctgc ctcagtgtgc tcctgctttc tggaatcacc catcacccctt gccttcaacc    5580
caaaaatcca gctgaccta gggctctaac accggaatat gaaatgaagt cacaccttct    5640
tccccccaga caccttctgg aaaggtaacc tagaattcaa gatgtcagtg agctgatgca    5700
gccttttcca aatgccagat ggtcaaagct gacagtgata ctgcaaacaa gcccagttgt    5760
gcatcttaca gtcagagagg ccagtgaggg caagggagca tcccaaagga cctaggggac    5820
agtgccctcc ccaagacagg gcctgggatt cctggccacc aagccaggga tcccccaccc    5880
ccaccccgcc ggacccacct gcttcccctc ccagagccgc ccaggctcag acctgctct    5940
gcaacccagc ctcacctcgt ctcgcccaag gaagccctcc ccaagcgccc agaccctgtc    6000
```

```
acttgttctt agatgatttc tttagaacga ttttgcaaag caagcttttc attcaatcca    6060
ttccctattt gtgagccatg cctccccca ggagtggtgt tttctagctt agaagggtc    6120 tgggaggtaa aacctcagaa ggctgccccc tgcccctcc agccagacac acgcacacac    6180
atttacactg aaggaccgtc ctggaagcgg acaggcaccg cagggaaggt ccaggcctcc    6240
cggtgctgga ttcctctcct ccacaccccc gtgcatggcg cgcacgcacg agctcaggac    6300
aaggaatgca ctgcctcaca gggggagaga tgggcacgcc cgctatagga ggtcgcgctg    6360
ccgtggcgac cctagccccc gggcagcaac gaggggaca tcgcagctgg agcaacagg    6420 cccaggccca gctcactggc gatgcagagc ccgagggaga ccccgcgcct tccgtcctag    6480
tctgatccgt cgccatcagc tcgagaggag cctggggaca gagccccgag tcaccctcg    6540 cccctccgga gcaggacgca cggggctcgc cctggtgggc tcaggggagg aggtgcagcc    6600
aggtgcgggt gcgggaggac gaaggccgag cgggtccccg tggcccccga ggaggttggg    6660
gcgcccccgt gcccgaccca gcatcttctt accgcagagc agtagcagca gcagcagcag    6720
cggaagaagg tgccggcgcc gcggcgctgt cgcctccatg gctagccagc tgtggcgcgc    6780
cgtccagctg cggcgggagc agtccagctg cggcaagcga tacagctgcg tccccgctgg    6840
gggcgctagg ggctcccgga ggcggagctc aggcgggggg gtgggccgc agagagcccg    6900 cccccaggag gtgctttgcc ccgggaggg gctcccaccc caggacgcgc tccaccccca    6960
ggacgcgctc ccaccccagg acgcgctccc acaacgagga tgcacgcctc ccccgcctc    7020 agcctcccag gggccctccg tcgggtcgtg ctcctccgag atacgctccc ccgcaggacg    7080
cttcctcccc taggatacgc ctgacccccc aagacatgtc ctcccccaca gggcagtcct    7140
tcccccagga ggcacccct ccccgggca agcccctcc tcctgctcca ggggcaaggc    7200
ccatgccaag ttcgcgcttg tggggcctcg gcgtccggcg gggcagggg accggagagg    7260 ggtgggcagc ctggcaagga gcagacggga tccggcaggt gcacccaccc ttaccccagc    7320
ccgcagaagg gctcggggag gtgtctggag aggggtgct gtgcagcgcg ggggacaag    7380 agagactggg aaggggggag ggggtgcgga gaggagcccc ccctgaggag ggagctagct    7440
gggagtgggg gagtccctgt gtgccgcgag gaaccctcat ggtgaatcgt gactgactct    7500
agagttcccg tgggccccaa tccttgctgg gggcctccct gcgctggagc ctttgcaccc    7560
tccggaccag aggggatggg gcacagacag gtgcacacac ctacacttgc acacacacca    7620
ctgcccatgg cccgggtcct caagccctgg tgcttgctct gtgctttctg aaggcctcgg    7680
gggacaaaag agggcctgga gcatgactgg gtgtccctaa tgacctgacc taaagaagtg    7740
tcatgggctc tgagggggagg gaggagggac tcaggattct cctaccatgg gtcacgtagc    7800
ctggtttggt cgcctctgtc actcatcccc tagcacagac cctggccccc atggacatct    7860
gggcactttg tcacctggtg gggtggaaac ccttctgccc tgcagtgctc agagacatgc    7920
tggtctgagg gctcagggag cagggctggg aaggtaggac cccctcaggg gttgactgct    7980
cttagccgga gcatccatcc caagtcagag ggatgagcag gagggatccc cacctggcca    8040
gggcctccgc ctctctgagt gggggaggca ggaattaacc cggcctggaa ggccgggggt    8100
gtgggaggat tctagcgcag gcgttgctga acagctgcct cgcataagcc ctgctgacct    8160
ttcctgcatt aggaagccca cttaataagg gatttctgcg cttattctgc taagaaccag    8220
aattatttca aggaggaatt aaagctaatt aaaattgacc aaccagcctg cccaaggtgg    8280
tggggagcac agatgcagga atgacccaga acctcctgtg acccaggcct ggcagggct    8340 gcaggctcca tccgtgcatc ctgccagcca cccttctcag atgccctgca ccaagagaga    8400
```

```
caaaccaaga gcaagttcag atgtcaccag tgtcccagga ggccacagga tcacggaggc   8460
ccacaccact ccacaggaga ggtgaggcca gaccccacag atggttgcac acaagcaggc   8520
tgggacagga gggtgggtca tcagagggqg ccagaccaga cagcaccctg aagtctgccc   8580
cctggggccg tgctccgcac accaccagta cttgggaatg agcaccctgg gaggcagcgc   8640
tggataaagt ttctcctctt tccaggatgc cctcccctcc cccatcctgg ctctgatgtc   8700
cctgcaggtt cattccctgc acccccacct ccatgcagct cctcggtctc ccacagcaaa   8760
cttcccaggg cccacaggct gccccattgc ccctgttaga aggagtccat gagaagcaag   8820
gctctagctc ctctcccctg tgccccacca gagcaaatga ctgctggtgc aggtggtttt   8880
tgtgagaagg gaagatgcac agacatagac ccagccaggc tccattatat ccaaaacaca   8940
agaccctcaa ggagcctagc attttccatc tgaagctgga gagaataaca tccctgcccc   9000
attctcagga cagaggtgag gacaaaggag cctgtgctga gcccacagcg ggatagagat   9060
ggaaattatg gaagtggagg tggtggtgga ggtggaggtg atggttgagg tagagatggt   9120
tcaggtggag atgcaggttg gaagtggcag aggtggagat ggtggagacc gtgaaaatgg   9180
tggtggaggt ggatgtggag ctggtgattg aggcagagat ggtaccggtg gaggcagagg   9240
tgatagaggt ggggatgatg aagatggtag tggatgcggt agaggtggag ttgctggtgg   9300
aggtagagat gatggagatg gagatggtgg tggaagtgga gttggtggac atggtggaga   9360
tggtggtgga ggtggagttg ctggtggagg cggagatggt ggaggtggca gaggtacaga   9420
tgatggacag agtgatggaa gtggaggtgg tgaaggtgga gatggtggtg gaggtggagt   9480
tggtggtgaa cgcggagatg gtacagtaga ggtggcacga gtggagatgg aggtggagtc   9540
gaggaggacc cagatggccg cagctggctc agaaaagccc agcagcctca tctgactcct   9600
ccttgcagcc ccatcacctg aacaggtggg aagacatggt tatcagacgc catcttctct   9660
agcaggccta gagggtcctc tcctcactcc tgtctggccg caggccaccg gatggaaaaa   9720
gagcagatat gttgattgag gaggggcctc tgcaggctcc tgggacatgt gccaggtcct   9780
ctgggaaacc caggcactgg atgggcacaa gagcccctaa gacaggcact tcctgtgtgg   9840
ctcctggagg gcccaggctc cctggagcaa gccaagccct caggaatgag cctgagtggt   9900
gttgctagcc tgccggtgac ctgacagtca gtgccaccca gagggcagca cggagtgggg   9960
gctgctttcc acctatacag ctggaccccca gagtctgaga cccagcgaga aggcagctac  10020
ccctgcacct gggtcttctc acctgtgaca ttcggaggct cagttccact acatgtatg   10080 atacaccaag gcagcacctg gccctgatg tactccccca aagatgtggc cccaggagt   10140 ctgctgaccg ggtgccccta cagctgtgtc ctgtctcccc acgtagaccg tcccgtctcc  10200
cttcccagtt ctctgtatca gcctctcctg tgccaattac tgcaaagctt ccctctcctg  10260
accagccctg actgacacag tgttatattt attcggtcat ttctctttct tgtaatggtt  10320
ttaagagtaa gttctctcaa cagtaaagtt ctcctgtagc tcagcggtta accctccact  10380
gcaacagctt ggatcaccgc tgtggtacaa gttcaatccc tggcctggga gcttccacat  10440
gtggcctgtg cagccaaaat aaataaataa ataaataaat aattaaataa aggcacttct  10500
aagtggaggg cttgtgagca aatgcgatca gagaaacgcg ggccatctca gccccacgca  10560
tctcgcccag gagccagcag gagaggagcc gagccaggct cagggagggc cctctctgga  10620
ggtttccctg caaagcccta gaccttggga gacttgactg gagaggcccg aggagcaggg  10680
caggcgcatc ggtacttggc gcccctagc ggtgaaacat tgcgtctcca tcctcagtga  10740
```

```
agcagagaaa gtgacacccg catttgaagt ggcagcgatc tgtctacacc gtaggcagga    10800
aggagatcct ctgacactct ggtttcccag agccccaggg ctcaaccctc tgtgtgtggt    10860
tgttgctgct gttgttgttg ctgctgctgc tgtagtaaaa cacacatcat aaaatttacc    10920
ttcctatcca cttgtccgtg tagcgttcag cggcattgag caaacttgta tgttgtgcag    10980
ccatgaccac catccatctc cagaactttc accttcccaa accctgcccc catgaaacac    11040
caactccccc ttgcccccte ccacagcctc tggcacccat gaagtgtctc tatgaatctg    11100
accattgggg accccataag tgaactcacg tctgcccttt tgtgaccggc tatgtcactt    11160
agcatcacct cttccaggct cctcgttttg cagtgtcaga agttcccctc cttcctgagg    11220
ctgaacacta ttccactgtg tgacacacca ccttctgctt agctctactt tgccgtccgc    11280
atcctctgta agtgaacaaa gcaagcttcc tttcgtttaa ttccattttt gtcaaaccta    11340
tcagaaaatg ttttggggag gagttcccgt catggcgcag tggttaacaa atccgactag    11400
gaaccatgag gttgcgggtt tgatccctgc ccttgctcag tgggttaagg atctggtgtt    11460
gccgtgagct gtggtgtgag tcacagacgc ggctcggatc ccacgtcgct gtggctctgg    11520
cgtaggccgg tggctacagc tctgattaga cccctaacct gggaacctcc atatgccatg    11580
ggagtggctc aagaaaacgc aaaaagacaa aaaaaaaaa aaaaaagtc ttggagttcc    11640 ccctgtggtg cagtgggatc atatctggca ttagtgtggc tgtggctgtg gcagtgccta    11700
cagctccgat tggaccccta gtctgggaac ccccacatgt ctcgggtgtg ccctaaaaa    11760 aagttctgga gggccgcact gcccaaattc caggggaggg cggcggtgat ccaggctaag    11820
gcggaagtgg cagaggtggg accaggagca agaaagctgc caagctcccc tgcttccatg    11880
gcatatttat cccccccttga tgtttcctgg ggggcaggga gggggccatc tccccaaacc    11940
ccccttctca ggcttgagag gtgtgtgcct tcccaggacc tgaggcagca catcctcagc    12000
ccaaaccccc cctgctggac cctgaccac gccctctctg agtcccctg gtcccatgtc    12060 aggacacccg caggtcacag gtctcagtcc tcacggctac agctcttgca gcccctcaga    12120
tgcggctgtg ctcccccctc ctggagcaga ggagaggcgt ccccctcact gcctgcctcc    12180
ctctcctcct cccttaaagt cacctctttt cccacgtccc gacttttcca ccataaatga    12240
gcttcccttt tccagccgga acatgacaaa tattccatgc gactgcacat tagtgatggc    12300
aggcctgatc cttcaacagc aataacctaa tcacttgatc ggtgacctga tttgcatgaa    12360
gtccctccat agcacgcggt ggagcctggc ttgtccgagt attctggcct catagcccag    12420
cccgctcccc aacacacccc tgggcctgag atgaaagggc tgctgtctgt ctcctgcggg    12480
acaagtgctc ctggcacacg atatgcacac aaggtgtatc tgctggatgg atggatggac    12540
ggatagatgg acgacagtg gccatggacg gcccacccte tccagctggc aggtcactca    12600
gcctgtcaaa acttgtgagc aagagtgact tcacacctgc attttgagaa gcagctggag    12660
gaggggccct ggaccacaag ctctcaggga gacggaggag gaaaaggcag tgaggagtgg    12720
gagtgaggca tttagggata acatcggcag gacttggcca gaatccccca gtgttctgcc    12780
caggctcagt gggtggaggt gcaggcttag caggagaggg cctggccaga cctcaggaga    12840
aagacagggc tggctggagg tgggccgtgc agaaacccca gcaaagcgga agcttggtgc    12900
cttcaggacc tcattgagag gctgagcgct ggaggttaag ccagcgaagc accaagaagg    12960
gatgccaggg ttgagaggaa aaccaggcgc acagtgggca caagggacc acacatcaca    13020 ggggggagga ggctgaaggc tggggacgcc cacagaagtc gccacaactt ggcaggagc    13080 tgattcagag gcagctcgtc tgccctccct gccctgagcc tggaagggt tgctgctgag    13140
```

-continued

```
gcacaggctg gatccctggc ccagtccagt gggttaagta tctggcgttg cctcagctgt    13200
ggcataggtc acagccatgg cttggagtcg atccctggcc tgggaactcc catatgctgt    13260
gggtgcagca aaaaaaaaaa aaagaatgt  gtgtgtgtgt gtgtgtgtgt gtgtgtgtgt    13320
gtaactaagt cactttgcta cacagcagaa attaacacaa cattgcaaaa caactatact    13380
tcaataaaac ttttttaaa  ttaaattaaa attaattagg agttcccatt gtggctgagc    13440
agtaacaaac ccaactagta tccaggagga catgggttcg atcctcggcc gcactcagtg    13500
ggttaaggat ctggagttgc tgtggctgtg gcatagaccg gcagctgcag ctcccactca    13560
acctctagcc tgggaacttc catatgctgt ggatgtggcc ccaaaaagac aaattaaaat    13620
ataaaataaa atataaagat aaagagtaac atcagaaata cagcagagag gagttcccat    13680
cctggtgcag cggaaacgaa tctgactaga aatcatgagg ttgcgggttc gatccctggc    13740
ctcgctcagc ccgttaagga tctggcattg cgtgacctgt ggtgtaggtc acagacaagg    13800
cttggatctg gcattgatgt ggctgtggtg taggccagca gctgtagctc cgattagaac    13860
cctcgcctgg gaacctccat atgccgcagg tgcagcccta aaagaaaaa  gaaaagaaa     13920 aaagaaagaa agaaagaaat acggcagagt gaaaaactcc ctttgtctct ccccttcaat    13980
ctacaccagt aaaacatcca attcgacaaa ggttcctcct aacacagcag gacagagaga    14040
atgcccgcgt cagtacatct gaaggtgggt ggtttggaac agaggaggca gaacccaggg    14100
agcagtgggg tcggtgcctg cggtgctggc cctctgacca aggcggcttc agagaagcca    14160
ggagcagcag gggaaccagc acacaagagt caggccttcc aagtgcacag gtgcccatgg    14220
ccacagatgc ctgggcagca ggggcagtgg agccttccag ccactgaggc acccactaca    14280
cccgcccccc caccggcagg gatgtagccg gtgaacctta caacagaggc acaggagaga    14340
tgcctgtgga cccgggcgcc ccctcccatc gtctccctct ccaacagtgg agcctgtgtc    14400
tcggggatcc caggcacaag ggaagagccc acctgcccag ggatgacagc agctctgtca    14460
gaaaaaagga agcaatgacc ccagaggcac aagagtcaac aaagaaggca cagagccacg    14520
cctcttacag aaactgcagt ggaaactgga aagggctgat tctcaagtat gaccagaggc    14580
agctcagcta aaagagaaac caaacactgt gtgacagcgc cccctaccgg ggaataaatg    14640
aaaggactct aacttttttg ggggggtggg aattgcacat tttatttact atttatttgt    14700
ttgtttattt tttggccacg tctgcagcat gaggatgttc ccagagcagg gattgaaccc    14760
gagccgcaac agtgacaaca ctgtaaagga ctctagcttc taacccatct tttgcgcgcg    14820
cgcatgtgtg tgtgtgtgtg tgtgtgcgcg tgcacatgtc ttttaggggc cacacccacc    14880
gcatatggca gttcccaggc tagggtcga  attggagctt cagcttctgg cctccaccac    14940
agccacagca acacgggatt tgagtcgcat cttcaaccta catcgcagct cactgccatg    15000
cccaatcctt aacccactga gcgaggccag ggatcaaaac ctcatggata ccagtcaggt    15060
tcgttaccac tgcgccacca tgggaacccc cataagctgt catttaatat caaatgcatc    15120
agcaaagaaa gagttcatca acaacatga  agaaccacag taatactacg cagaaagaaa    15180
atgacaactc tcccgaaacc agattaaagt catgaaacaa ttgcatctac ctgacagaga    15240
attcagaaga gctgccatga agaaactcaa ggagatacaa gaaaactcag ccaggcggtt    15300
gaatgagctc aggaataaaa ctgatgaaca gaaggaatac tttaccaaag agactaaaac    15360
tccaaaaaag agccaaacag aaattctgga gctgacgacc tcagtaaata agatgaagga    15420
tggattagcc ctggaaatag agcagagcct ggaagagaga atcagtgagc tcagagacag    15480
```

```
gagtccggca atgatacaag caaaagagga agagaagtaa gatttttttt ttgtcttttt      15540
agggccgcac ctgcggcata tggaggttcc caggctaggg gtcaaatcgg agctgtagct      15600
gccggcctcc accacagcca cagcaacaag ggatccttaa cctactgagc agggccaggg      15660
atcaaaccca cgtcctcatg gatactagtc gggttcgtta ccacggggcc acgaggcgaa      15720
ctcctggact ctcctcgctc ttggcctcag tcccttcacc gagcaggacg ggcctgggtc      15780
tctatcatgt gtcactgtct gacagcactg ccccacgtga ccctgggac catccacacc       15840 ttaagtccgc agtcagcccc caggcccctg cccgtgagat gcccgccagg gtatacctgg      15900
ggctagaggg ccacatctca ttcaccactg tccctggcca gccagcctgg acgaagggtg      15960
gataaatgag gacgctgcat aagagtgaca ccctgagggc ccagccagcc aagccttcct      16020
ccaccgtcct gcccacagcc cctggagcct acccttttgcc ctggaggtcc taccaaccca    16080
gcagacccca ccccccaacc gaccaggagc ctaggggcc atggcgctgc tgggacaaga       16140
ggagaagggt aatgagcccc tgtgaaactg gtgctccagg tggtcacagc tgggcctcgg      16200
ttcccgtcca tcctggcaca ccagagccgg gggagggaca aggcctgcag gtctgggaag      16260
aggacaggtg gaggcccggt ggggccagta acacccccca gggcccaaga acactgcgtc      16320
cctgctccag ggctggtgag ctcaaggaac atcattcctg gaaatttcta gccctcgggg      16380
ccgagcacct gccccaaggc ctggcccacc aacacctctc cctgcccagc ccgccagac       16440 ctgcaccccc tcctggccag gccttcgggc ccaggcagt tggggcgggc cccagcccc        16500 ctccaggtga aagcgcagt cccatggctg ctgcatgaag ggttcccttg gaagctgagg      16560
aaacgggtta acggtggtgg cctgccaggt aagtgacctg gttccccacc actgatgaca     16620
tgctttccag aagtcttgcg ggcatggagag aactcggagt ctctgtgact gcaccacacc     16680
tgcagcacag ccccagtgac acaagattgt gtaggggcgt tggggacagt caatatatct     16740
acagaaggat gtggtatata cagaggtgcc tgcagaggaa aaaccaggtg aagctgaacc     16800
aagacgtgcc caaagaagcc cccagtcatg tgtgatttgt ttcttcttt gagcttttct       16860 gaattgttca agttttccac aagatgtact tgtgggtttt gtaatgtaaa aattttgagg      16920
agttcccact gtggctcagc aggttatgaa cccaacacag gatccaggag gatgtggatt      16980
cactccctgt tcttgctcag tgggttatgg agccaacatc gccatgagct gtggtgtagg     17040
ctgcaggcac ggttcgatcc cacgttgctg tggctgcggc ataggcaggc aactgcagct     17100
ctgattggac ccctagcctg ggaacctcca tatgccgtgg gtgcggccct aaataaataa      17160
ataacagaac acagttgggt tgttggtatt taaaaaaaag aaagaaatct gtagagagct     17220
ttcattcatg tgtcacttca tgtaatccac atgcctaccg atcgtgagag atgctgctgc     17280
tgcctccgct tcataaacgg gaaactgagg agggcacgtg tccagggaac aacctgaggt     17340
cacacagcaa taagactacg gcctgagtcc caggaacagc cctcttccat gaagggctta    17400 cccagggcc ttaaatcctg agacttcaaa tcttaggcaa gacttcaatg ttagccaatg      17460
catttgtatt gatcaaaaaa tacattctgg gggttccac catggcacaa tgggataggt     17520
gaaatctgca gcatcgggag gcaggttcga tccccacccg gcctggtaca gtgggttaaa    17580
ggatccagtg ttgccaaagc tgccacgtag cttgcaacta caacgtggat ctgatccctg   17640
gcctgggagc tccacaggcc aagggtcggc caaaaaagaa aaagcaaatc tgaggtgtcc    17700
cctcagcggg ttaaggatcc agcattgtca ctgccgtggc tctggttact gctgtggccc    17760
aggttcaatg cttgacccag gaattttctgc atgttcaggc atggcacac cacccgaga      17820 gtcccagctg tgaccgtgag gataagaaaa cgccaaggac aggaatctct gctaatgtgc     17880
```

```
cgagcaccgg gcaccgaacc ctcacaacaa cctggtccca gaggtatcat caccacctct   17940
ggcaccgatg aggaagcagt aaacagacac tcacagagct agcagtgcct ggacacccca   18000
ggcgtggact cgaacctgac tctgagcctc gtcatagaaa aggcattcac accatgcctc   18060
atgcttattg gacttcacct ccctgggtaa aggagggaag ttttagggga ggggctagt    18120
gataggatca tgccagtggg tggaagctca gctggccaga aaggggcccc tggtgcagcc   18180
ccctcctgct cccacctgtc cacaaagttc ccgaagaata agggagctgt cccagacact   18240
gggacacctg atcagtgaga cagaaggag ccctgaccgc aggggactta cactcaggaa    18300
aaacagacaa taaacaggaa atcaatgaa tgatcaaggt cctccagagt caaacaggtg    18360
tggtaaggca gccgtcagcg gcccgggtac aagagagcc ttggcagggc agagccgggg    18420
agagaggcga cagcgagcgg gagggcttcc agaggaccaa tggggaggc tttgcaggtg    18480
ccaggcttcc tgctctgggc aggggtgggg gtgctgttcc ccaacagaag agattctggg   18540
cacccaggaa ccagtgccca ggctgtgccc atcccggaaa agacggtcac tcttgggagg   18600
ggagaaacca gggcagtgag gccgaggggc aagtgtagat gtgaccccaa aatgggcaga   18660
gcaggaggag cagcggcggc ggagggacca ctgggcaggg ccaggggagg agtcaggacc   18720
gaggagggaa cggaaaggag gtgaggcggg ttgaggggca cctttccatg gaggccagac   18780
tgtgcagagg gggagaccat ggcagcccaa agcggaggga agaggactca gaaagaggcc   18840
cgctctttta atttttgtt gttgttgtct ttttagggcc acaccgtct ccaggccagg     18900
cgtcgaatca gagctgcagc cgttagccta cgccacagcc acgccagatc caagccatga   18960
ctgggaccta cgcaacagct cacggcaacg ccagatcttt aacccactga gcgaggccag   19020
ggatcaaacc tgtgtcctca tggatgctag gcagattcat ttccactgag ccaccatgcg   19080
aactctgaaa gaggccttct agcacacaaa gttcatttgt cttgcccaga aagaagatgc   19140
aacggactcc caaaccccta gaattccata tgtatgaag tgtccccaag ctctctaact    19200
tcatactcaa cagaacattt ttttctctt tttacagcca tacctgcaca catggaaggc    19260
cccgtgctaa gggtcaaatc ggagctgcag ctgcagctgc cgcctccgcc agagcactcg   19320
gcaacatcag atccttaacc cgctgagcaa ggccaggcgt caaacccaca tcctcatgga   19380
gatgagtcag gttcttaacc cactgagcca caatgggaac tcctcgacag gacactcgat   19440
acgatgtgga gccttgcgag ggcggggcaa ggcatgtgac atgtgtgtcc acccttcctg   19500
gccaccccaa gtgcacccgg cattcgtgat gtcccatgtg accccaactg gagaggaacg   19560
gacatcctgg gtccctagga gacttcagac acagggagga ggcaggggcg tctaagaacc   19620
ccaagggacc cagaacgccc ctccccttc caatggagct tcttcctgta ggaccagcca   19680
gttacacaga aaatgaggac aaagagaaag ggacagacag aaagagccct ccgctccttc   19740
tctttcagcc ttgcagactc cgggccggct gggtggagtg cagacagact gtgcaggtag   19800
gcagcgaaac caggaatacc ctcagcagca ctactcagca acagcccgag cagccgtcgg   19860
tacaggaagg gcgaacaaga cgtggtccag ccgctcggcc gagcagtgtc cggccataaa   19920
cagaaaggaa gcgctgagca cgctcccctg ggacgccccc tgaggactcg atgctcactg   19980
agggccagac acaaaaggac gcacaggcca cggttccgtc tacatgcaaa gtccaagacg   20040
ggcaaaccca cagagacagg aagcagactg gaggttgcca ggcgctggga ggcggcgagc   20100
agtcactgct aacagacaca gggcttcctg ggagaggaat gaaatgctct aaaattaaag   20160
agttagttgc agggagttcc ggtcatggct cagcagaaat gaacctgact agtatcctca   20220
```

```
gggatgcgga ttcgacccct ggcctccctc agtgggttaa ggatccagca ttgccgtgag  20280
ccgtggtgta ggtcgcaggc atggttcaga tcccacattg ctatagctgt ggtgtaggcc  20340
ggcaaatgca gctccaactg gaccctagc ctgggaacct ctacatgctg agaaaagaca   20400
aataaggagt tcccattgtg gtgtggtgga acaaatctg actaggaacc atgaggttgt    20460
gggttcgatc cctggcctcg ctcagtgggt taaggatcca gtgttgttgt gagcaatgga  20520
gtaggttgca ggcgcagctt ggatcctgca ttgctgggc tgtggtgtcg gctggcagct   20580
gtagcaccga atcaacctct agtctgggaa tgtctatatg tcgtgggcac agccctaaaa  20640
agcaaaaaaa aaaaaaaaaa aaagacaaag agttagttgc acagttctgc aaactaaaaa  20700
ccactgactt gtacaccagt gaactttatg acatggaaat catatctcag taaaaagaa   20760
aaataagata aaatcaagaa tgcaaatttt accctcttca acatagaaac acacctagaa  20820
gtgtgcggcc gtgaatgaaa accagaccctt caggcagtgt ctggcctcac ccttcgggca 20880
caggcaggac catggagggt taaagggggtt ttgttgacgg gagaggcccg tctgacaaaa 20940
gtcaatcagt tcattgtatc aggaaaaata aaagtgcttc cgaggacaca gactcctcag  21000
aacaagaatg cgtctgaaaa taaaggaaa agaggtgaag agaaagctgc tgggtgagtt  21060
ttgtgcagaa tgaaatacac gtgcctgtcc cagccaggga tgtgaagtgg gtgatttcgg  21120
tgattctgca taagagttaa atgctcctga gtttgcattt caagcggcat tgcacaacat  21180
aaagacaaac ggtaataata gaaacattta attttttttt tttttcattt ttggccaccc  21240
tgcagcaatg tggaggttcc caggctaggg gtctagttag agctgcagct gccggcctac  21300
accacaacca gagcaacaca agatccaagc tgcgtctgtg acctacacca cagtgcttgg  21360
caataccgga tccttaaccc actgagtgcg gccagggatc gaacccgcat ccacatggtt  21420
atagttagtt ggattcgttt ccactgcacc acaagggtaa ctctaacaca tttttttttt  21480
taaacaccgt tttttaaaaac aaaagagaga cctggaaaag aggaaaacct ttgtatttag  21540
tctatttgcc cacttttttc ccacttgttg aacaaagaac cccacaaagt acatcgccag  21600
ccctctgtca gcgaggaagg gaccaggctc tgtgaccctg tgactgcagg ccccagaggc  21660
caagggctgt gaccgtggga gccagagact ggagactcag aatgaggcca cagcccagtg  21720
gtctgagttc ctggtgtggt caagccaggc cttggacctt gcatctgagt agggggggacc 21780
ctgagaccctc ccggccatgg tgtaagggaa gcgcagagaa tagggagaga aaggccagct  21840
gggccagaca gagagtgatg atggcctggc cgcccctcgc ttctccaccc tcagtgtctg  21900
gcgtaggtac cgcctctttt ccaggctgca ggacgggaaa caaccaaagg cgtggcattg  21960
tgccaactac cagcacggaa aggcaccaag agaaagcaag tcacccttgg ccaggacctc  22020
cagaccccaa tccccgaagg ccagccctgg aggggtctgg gctgaggccc tagaatgatg  22080
ctgagggggtt ttctgggccc agacggtgct gcgtggggtc cagggcaggg agagccaggg 22140
gcgttggagc cacctatctg aatgcaagtg tgttctgggc tagaacatct ggaaaggtct  22200
gtagcacaag ctgagggccc gatgggaaga agtgaggggc tctgtgtcca aggcctcgag  22260
gccgcaggcc cagcagaggg gtgcggcctg accagagcg gggtactgac tatcggcaca  22320
tgtggtcgcc ctgggccac cttccctgtc catgccctca gggcacaagg atcaaggaag   22380
tctccccaga gaagagggg cagagtctga gcattcatcc tgcccccac ccctgcagcc     22440
tcccagggca aagcgggggt ccttctggga agaggccctc ccagtgccca cactgcacgg  22500
aaacagcccc gacactgaac ctgcctgccc ctccccttct cagacaactg acattctctg  22560
cacagagcac acagctcata aactcaagat ggccattctt gctgcaggtt cggggcgggg  22620
```

```
ggcagagggg agaaaaccac tgcaggagaa ataaaatgcc ctccacagta acccctgctc   22680
cacctcctct gctacctgtg ggccatgttc tgaactggac atgtcactcc ctgtccctga   22740
agggccctcc atgaccacag aaaaggttgg ctatcgtgga acttgtttct tcctttgtct   22800
gccctaattt tcttaattct catcatcagc atacattact ttcaaatgta tgcttattgt   22860
gggaaaaaag tccaccttaa taggaattct tttatttttt cctttaaaaa tctggcccag   22920
ggtgctcctg ttgtggctca gcgaaaatga atccaactaa tatccatgag gatgcaggtt   22980
caatccctgg ccctgctcag tgagttaagg atctggcatt gctgtgagct gaggagtaga   23040
tggcagatgc agctcggatc ctgtgttgct gtggctgtgg ctgtggcaca ggccagcagc   23100
tctagctcca attcaacccc tagccctagc ctgagaactg cagatgcagc cctaaaaaag   23160
caggaaaaaa aaaaaaagt ggcccaaggc agcaactacc ccatctgggg tctatccaag   23220
ccggaagccc ctaggccctg ctggggcagc gccagccacc cgccctccct ctaggttcct   23280 gtaccgctg cctcctttaa aaatgcccca gggccaccag ccaccatctg ccacctgcct   23340
gccagccacc accatgcgct ttcttaccag tctggccctg ccctgatcg ccctggaggc   23400 tgccctcgca ctggccccag ccctcaatct gccaggtagg cccaggaggg tcgtcccgac   23460
cttccccctc tccaggtgtg ccccaaaaca ctatccagac ctcacagtct ggcgaccagg   23520
acaagaggag cagaatcggg aaggcacatc cccagggtca gtaacaacct aagcatggga   23580
tgggagctcc catggtggca cagcaagtta aggatctggc attgtctctg cagcagctcg   23640
ggtccttgct gaagcacagg ttccatccct ggcctaagga cttccatttg cagcgtgtgt   23700
ggggtggggg aaaaaaagt ggggtgctgc ccagagactc ccacatgctg gggaacaaag   23760
ctacagggct gaggccactg tccctggaaa agaagtgacc agacagtgaa gtggatgtgg   23820
ggggcacctg tcctgtcctc agggtcttaa ctccacctcc tgcagtgggc ctgtggcctt   23880
gttcccgaat tctcacagct gactcacact tctgtcagcg gtcacatttc tggcattttt   23940
ccttcctgga agcagggtgt tggggtgccg aggagcaggc tccccacgct tcttgtcctt   24000
gccccaccct gctcttccct aaggagcccc atcccaccgc cccccaccca cctgccacc   24060 ctgtgtgcag ggctggccac gtgcccagag ctcagctcct cctccgagga cccctgcgta   24120
atctcctgcg tcaacgatga gagctgtccc caaggcacca agtgctgcgc caggagcccc   24180
tgcagccgat cctgcacggt ccccctcctg ggtaatgcca cccatccctg tgccccagca   24240
gagccctgct ggagggaggg ctttgccaag tgtccgccta gagtctgcac tccgcacccc   24300
tctctcagag aaccccggc agcccacgc actcggcctg gccctgacac gggcccacgg   24360
ctggacccag tcgaggctcc cccacttctt ccaatgtcat gcaggctgca gtctccctcc   24420
cggccctgaa ggccccaaac cactaagggg gtggggtgg ggggcccacg gaagacccac   24480
agcagggcag gcccagcaag ccagcaggtg aggaaggcct ctcccatctc tctcccagtg   24540
cctgtcccca aggccggccg ctgcccctgg gtgccggccc cgctggcccc tgagctctgc   24600
ttggagaaaa atgagtgctc cagggacgac cagtgtaggg gcaacaagaa gtgctgcttc   24660
agctcgtgtg ccatgaggtg tctggaccct gacacaggta agttcccaag accccactcc   24720
tgggacaccg ttctgggcca ccgcctggg aatggtggac ttggcttctc ccttggcctc   24780
ccctgaactt ggtggcctcc acagggcccc aaaggccatg atattcaaca gagggtgggg   24840
gcttaaggga cagcgtgacc caggctgcac cagccacaga cttctgcagg ccctgatgt   24900 ggtcactggg atacagaggg tctccgtcta gcagagggg ctcagaggag ccctgacttc   24960
```

```
cgggtgggac ttccagccag gcccgcctgc cacgcttgtg cctttgccac tcaatctggg   25020
gaggagacct gggctaggag cccagagatg cggttcctgg ataaccagtc cctgccaccc   25080
ttgaccttgc cggcccacct acggcaatga tgagggccca ggagggatgg gtgtggacgg   25140
ctcgctggct tgcccacaca gtccctccct ccccgccccc acatggctgg gctccacctc   25200
ctctgaggcc tccgtgtccc ctacagaggc ccctcttcag tgaggacat ccctgggagc   25260 ccccggctgc aaggagtgac cagcccgagt ccactcagca agaaccttct ctctcggatc   25320
cagagaccac acgatgcctc ctatctgctg ctaataaaaa cctactcggc ttcatgtctc   25380
tccgccctct gtctgtctgt ccctggaacc tgccagaggg cacgagacac acaggccttg   25440
cctctgagag ctccccagca agcctggaag ccctggaaa ccggcagtcc cagctgaggt   25500
gtagtgagac caggcaggat gtaggtagac aggacgggtc ctgggtgagc cagaggaaag   25560
gccaccacct cttctctccc agggtctggg ggagctatgg ccccaggtg ggcacaggct   25620 tgacctgggg tcagtcctgt ctgggccatc agccagcact taaggtcaag ggggccaccc   25680
acatcatcac actggctgag atgaaggtgg acatgggga cgtgtctcac ctccctccat   25740
ccctgccctg gggagaagac ccttcccaga gcttggaagg tagggtgaca gggccagtca   25800
tgggaagccc aggcccatgg cacatgaggt cactcctccc tggctttggt gcccacgagg   25860
cctggccccc attatacgga gtcagtgaag aggaaaaaag cattctcgac tgcctattag   25920
cccctgtgta ccagccctcc ccaggctact ggctttgggc gtacacaagg tcccccacaa   25980
aagagagcct gctgtgttgc catatgcagg agaagagagg agccctccta aatgaaagtg   26040
gccctagaac tgctggagaa ggggagcggt ggggcccagg gccatctcag aaggcaccag   26100
gcactgagag tgggcaactg cttgagaccc tgggcctctg tgtctcctcc accttcctgt   26160
ccagattcac tcgataattg ccacatttc agtctctatc atgtgccagt tgatgagcgg   26220
gaattggaga gacaggatga attgtcccaa atgaaaaggg cttcaaccaa tggctgaatt   26280
ctgtttctga accactaaag gaatcagaat tccttggaga aacagccaag ctgaagaact   26340
atcaagctag tgtgggcatc ttgcatcata aagcatggag ccagcctgag tccccaccag   26400
ccaaacttgg caccaccagg gtatccatgg taaagcatga cattggagca aagggaaagc   26460
tcttcttcac agaagatgct agttaacaca tggagaagga acgactgagt tagaaaagcc   26520
accatttgtc aacacccaaa ataatcgtta atctgagcaa gaatcattag aaggcgaaaa   26580
cccaggtgca gagattgccc aggattcaca aaggggaag ctgcttccac aacaggcagt   26640
gaggagaggg aggaggagga aaacagagac taggggagga acagctgaag aaattcgagt   26700
gtggactaga cactagatga cctgagtgaa tcgatgtgaa tcttctcggt ggaataacga   26760
cgtggtggtc acgtggtgaa catacactgc tgaattactg agagttcacg atgtctgcaa   26820
ctcactttca caggatatat cgcactaacc aatacacaca caggcttaca tctatctatg   26880
gaatgcctac cgacatgtgc gcgtgcgcgc acacacacac acacacacac acacacacac   26940
acacacacac gtgtgccgtg gggaggagag agggagaaaa caaaggcacg agggcaactg   27000
ctaccggctg aagccaagta aaggggagag gatggtcact gtgctgtgct ctgagctttt   27060
cggaaaggtg gccgattttc acaataaaaa gggaaagaag gtcaatgtcc atgagccgac   27120
cttccaggcc tagagagtgc tgggtcaccc gatgggaggc ctgtgcaggc tgccatgttt   27180
ggaaggtcct gaagtgggta acgcgtggct gggaacccag caccagagag gaggcgctgc   27240
tcgaggacac acaggaggga ggcctggatg cccagcaggc aaaagggcac tccagggggc   27300
gaggaagttg ggtctgcagg tctggaggga gccccagcca accaacacgc aaagggactc   27360
```

```
tggactttgg tcaaggacac acagagctac cacacctcca ggaagcccca aggctggaag   27420
agagaaggca cccctteccc caccccace tgtgctggac aggtgccggt agagcttctg   27480
gggagacagg tgagtctgag atggagctga acccctggac ggggctgtca ctcatgctgg   27540
ggcccaggcc caggaaagac ccctggctgg ccctaatccc agcctgggca gctggaacca   27600
cccagcccac cctgccctga gctcataatg aatggtgtgg aagatgcagc agccctgctc   27660
actcccatgc tggggattct tctcctgcag agaacaccca tcccggcatc aaccacatgc   27720
cagcttctct actgtgatgc tcttaacatc taccctacat gcatatcctg gacgcctcaa   27780
tgacacgccc gtcccaccct gctcggcttc ccgcctcagg tgtgcaaatc aaccaaccca   27840
gagaccacac ccccaccacc tcctctatgg ggtcttatac tccaggtcac tgtcctacca   27900
cagggccagg gacagacaac tagggcagc ccctaccccc ccgagccctc tgccattact   27960
cacactagcc agtcctaagc ctgctcatcc tgactctccc actccttcca cggaaaccac   28020
agcaaaggct cctgcccgcc aaccccaccc ctcctggctg accctgtgct tccccggtg    28080 gcccttcatg agggaggtgc ctcttctctg tgggaactgt tagtaataaa ccatcctcac   28140
tggcagtcat cttagagttt ccattaacac actctttcaa aacagtcact ttcaggggcg   28200
ggagatccag gggctgtgag gggattcgct ctccactcca ccacctcttg aggcttttgc   28260
tcccagcagc ccaccccaga gctctcagca ccctacgagg ctgaccccctt ggcctcacca   28320 cagctccatc actcctgcaa tgcccagaaa gggcccttcc tgcagcacag gtactcagtg   28380
ccaaccgcct tcagagtagg agcgcaggtg gaagccagga gcggctgtaa ggaaggtccc   28440
ggggcgcagc accactctgg gcctcggttt ccccatctgt cagcaagcgt gttggacgag   28500
aaggcttctg aggtatccta gctctctttt ccaacccctc tgggagggag accgcagccc   28560
tgggcagccc gatgtcctgc caggtggagc cacagcttgt tcctcattag ggaccttgct   28620
gtctaaggaa ggcatttggc tcagattccc cacctcaggc cagtccatcc ctcaaagtca   28680
ccaagaagcc agtcctaagg ggaggaggag gtagtgctag aatcaggaag gaaataagaa   28740
tgagcaaaat atctgcttct tccatgccct cctccacact aaattccatt tcatcgcctc   28800
tgatggcagc acagtcccac cctcaatgca caggaactta ttttgaagat gtctttaaaa   28860
gtcagatcct ctcccccaat ccacaacctg aataactacc tctctctatc ccctcccaa    28920 aaaaggccag aaacttctct ccaaagaaga taacagaggg catctggaat ggactgcctc   28980
agccctctgc aagagcaggg ttaccttgca aaaatccaat gactgtggca gttctaaatg   29040
tagggaggga gggaggggga acaaacacct cacatacaac ttctggacgc ctcgtaaacg   29100
tgagacacta acgagctaga ggttcacaga gtagccttcg aaatcaggaa atgacttcta   29160
aaatacccag ccaggggtc cctgtggcct agcagttaaa gactcggcat tgtccctgct    29220
gagcctcagt tcaccactgt ggttcaggtt ccatccctgg cccaggaact ttcctatgct   29280
gtgagagagg ccaaaaaata aaattaaaa aaaagtgat aaaatatgca ggcaaactat    29340
caatcaggca ggaggatata ataaagacat tctaaacctg caaaaggcct ttaaaactta   29400
cctccttggc atcctctctc acagaggtac tggaaaatgt gctctaccca acaaggggaa   29460
taaaccaaga aatacgataa aagacctagg aaatgagaga gaagcaaaag gaacacttag   29520
gacgtggtaa agggagactc ccaggatgac acctgccctg agaacatagt ggtgataata   29580
cgccctggag gtcagaaggc tcaggaagaa acttcctcag ttaagattaa atgtatgacg   29640
tatgtgaagt gttggaacat ctcgagagac ttagacaact ggagacggat cttggggaga   29700
```

```
atttgcaata aatacgtgga atcttaaacc gcaacaagac aattctttat atcaaggaaa   29760
taaaaacttc tgcaggaaga aaaattaatt gagtctcttt acagacctct tgtttggctt   29820
tccccgcact ttcattcttt tataaaatta aaagtcaata ctcaaaaatc agtacattgc   29880
acttaaaatt ccagagtcct aggttctttt ctggaaaaac tgcaagatct aagcaaatcg   29940
tgcctacctt tcggcacacc tataccgagc ggccgcccac cgggtcagag cccagcccac   30000
ccctgggcag tttgcagacg cgcttctca atcaactggg agaggcgcgc ggggcaggca   30060
ggagaggcgg gggaggcggg gtgaggacaa ccgacgactg agggtcgcct cctgcactcc   30120 gaatggggc tggggactga ctggcggcg ccccagcctc ctagcctta tttccgagcc   30180 ttttactctt tccccgccca ttctcccgac accgttccac gacggtccgt cacttccctt   30240
cccattagcc agtttgcgcc ctcagcaaag atggcacccg accggaagtc agcggcaggg   30300
aaacggaagc gggagcgact tctggcccgg aggcgggcgg cgagcctcgc ttccggcggc   30360
gctccgagtg acgaaagcga gcgcgccgcg ccgtgtggaa cgaggcccgt gctcgggcgc   30420
atggaggtca gcggcggcgc tcgtgacggc ggcggcggtg gcgccgtagg tctcggggcc   30480
cggggggagg gggtcctgaa ggcaaggggg gcgtggccag gagaggagac cggga        30535
```

<210> SEQ ID NO 8
<211> LENGTH: 9339
<212> TYPE: DNA
<213> ORGANISM: Pig

<400> SEQUENCE: 8

```
ctgtcctcac ccgtggatgg ggaaccccag caggccaccc tcgagagctg ggacctgtgt     60
gagcaccagc tcctccatca cccgagcagg agcggggcct tctccctgtg cccttgccgc    120
ccgtccaaca gacactcacg tcgaccagca ggaagccagc ggccagcagg tggcgccggg    180
ccagcacaaa gcgccccagc aagtctttgc ttcggctgtt gaagttgggg aactcccagc    240
acaggaaggc cagcctgcag ggggacaggg gacgctgcgg gtgccttcag ctctcccggg    300
ccccgagcaa caggccggcc agggccctgg gagcgaagag ggctatcaga ggagggtcca    360
gtctgtcggg cctgggggtt gtgtggctcc tacctcttgg ccccagcggg cagcggctgg    420
ctcccagagg gctgggcgag atgaggagcc acaaagtccc tcaggggcag gagctggctg    480
tcggcgtcca gcaggacctc agcatctggg gagagcacgg aacgaaaatg tgctcgggac    540
tgtgcctggg agaccaactg ggctgagagg ccccgcccca gctccgtgga tggacagaga    600
ccctggagag cagaggaggc aggtttaatt tcgtccccga caggactgcc gggaggggga    660
ggggagggcc ctcacccaga atccagccat atcgtgtggc caccaagaag ctgcccttgt    720
tggcgctccc cagcagtccc ttcagtgtct cctgcagctc cttctgcaag gggtcacct    780 tcttgtcaag ggcggagggc ctggggacca aggctgagga tggcaagtgg gggcctgtgt    840
actcggggtg ctccagctgg gcagtggcgt tgatatggag cagcttctgg aaggtgcttt    900
gatcctttgg ggacttgtca cctaagggga gggatggag tcagaaggga gggcaggagc    960
actgggatgg agggacacag aggccaggag ggggcgccag aggcaccccc gtacccaagt   1020
ctcaccaggg actctgggtt gggagcagca gaaagagggt ctgctggtca ctcacgagga   1080
gtggccagag caggagtgag tgcagggtga gccccgcct gccgtctcc ctcctgctca   1140 ggcagcctct ccgcttcggc agttgtgggt tcaggcggga gagggcacca cgggcttgcc   1200
ctcactcagg agaggctcac ctagaaactg gccgtgaagt tcaggcgga gcacagcctg   1260 cagctcggcc tccctggcct gctgcagcac acacagggac cacaccacgt ccacctgcag   1320
```

-continued

```
ggctggctcc aggcctgcca gctgcgaccc cagcttctca tgcacctggg caaggaccgg      1380
gcggggtgga gagagcgggc tctgctcagg ggccagacct ccctggccag gcccaaaggg      1440
gcgatgggga gcaacccttg gtcaggcttg gggcacccct ggtggaaggt accagacacc      1500
ctcttcctct cccaggcccg atgtggacag cagctgggct acccctgccc ctcccactgg      1560
cagggaccca cggcacaaaa ccacgtcgcc aggaggagct gggggttgta aaaggggaag      1620
cagccggctg gctgcggtgg ggtcctctgg ggggcgcttc gggtcatggc cgtccacacc      1680
taggacgctc tgaccactcc aagtggactg agatctctgg gcctcagcag ggcattaagg      1740
gagcactagg aggtgagcac aggggttcca ggcctgacgg cactgtgagc caccaggtat      1800
gctcccaccc gggccgccac gctggatttt gcgtgattgg ccccggaca tgccctgggg       1860 cacctatctg actctagcca gctccctcca tgccaggcct tcttccttac tacctctgcg      1920
cccagggctc cttggcagaa gtccaccccc tcaccccgc aagtcccgag ctgcttcttc       1980
gtggagggtt gagcatcagt gggagggagg gggatggggc aggggagca gaagactgta      2040 ccaggctgaa gaactggtcc tcccgttctg gccggaagtt cacacgggcg aaagccagga      2100
gcatgttgca caggtgtggc agagcgatgc tctgggctct gtccaggacg tgctgggccg      2160
gtcacagagg gcagaaggc gggatgagag gggcctggtg gtcagtcccc ggtgcccaca       2220
agccccccac cataagggct aatttacaca tggcagcggg tggagggcca gaccctagcc      2280
tctcagagat aatcacacac gcaaaggccc ctgacgacag ctttacaaat acccttcagc      2340
ccataaacgc agttctgacc tgtggcacat aaacctaaga gccagcaccc tctttcttct      2400
caacgccacc tggggcggct ggaaatttgg ggagagcact gagtgggttc ccggccttgc      2460
tgtctgcacc gctccccgca cagccactca atgacagaca aaaacgccaa cgtgtggcga      2520
aagactggag ataatcattc tcaactactc tttctctcgc tactgagtca cacagggtct      2580
ctccaaataa gccagagtaa ggtgccacat gtgccaccag gaagcggctc caggctgctg      2640
ggcccctgat gaggcaacca gggagctggc tcaagcaggc ggtcaggcag aggactctcg      2700
ggtctgcacc ccagctcacc tgggcaaagg cctcaaacag gggcaggctg agccacttaa      2760
ggaaggcaaa ggacttggtg cagcgggcca cctcgctgga agtcaggcta ggcgtgtggg      2820
gcagcaggtc agcagccagg cgctggaaca cctgggtctg gtggaagccg agtttgcctt      2880
ggggacagag cctgggattt aaccggtgag catccgcagg ctctccttgg gcccacaccc      2940
cagcccgccc tggtctcaag gagtaagagc ttcgtgtctg taaccaaatt tatccctgag      3000
gcccaacaga gaggatcagg gcccatgagt cacagtgttt ctgtggcagc ctcttgggcc      3060
agtgtctgcc atgggcgggc aggcactgaa tttgacacag ctgcggccac agctcgcccc      3120
ctccctctgc tgcccgcacc cgggctcacc ataggcatag gccaggtcca ggaggatgct      3180
tttcatcagg gtgaagggct tctggaccag gtggtaagag acagcccgca gcaagggcac      3240
cgagcgccgg ttctgagctg ccaacatcac cagtaccttc cgcagctcct cagggccaaa      3300
ctgctccacc agctccaggc actgtcaacc acagccggca ggggtcagct cggtggcccg      3360
agggccaggg gtcccatgca gtgaggccct gcgagacagc aactgggcct gagcttacta      3420
aacacaggcc ccgtctgtgc agggcctgcc tcagctccca gcccaggggc accatgttcg      3480
cagccaaact tatccccagg tcccagagca ggagacccag ggcccatgag ctgcaagctt      3540
gctgtggcag tcgtttgggc cagtcccgc cacgacagag cagggactga atttgacttg       3600
actgcagggc caagggggg tggccgacat ggtctctagg aagcacccac cagaagggga       3660
```

```
gccactgggc ttgcctgacc ctgccttctc tgcgttacgc ctaagacaaa ggagagcacc   3720
tttcccgcca ctgccaggat gcttggagga gccagtgggc acggagtgcc gcctgcagcc   3780
gcctgaagcg caagtccctc tagcgccacg ccccagactc catggacgga agctgccagg   3840
gctcctgccc ctgtaccttg tcctccaggc ggttcatcag cgactgggag aggtgtccta   3900
tcttcaccat catggccacc actgtgcgcc cgtcatcgat ttccgtccag cgccgctcca   3960
ggtgcacaag cagctcagcc agcagctcct gggagccctg ctcctgcatg taggtggcgc   4020
tggactcggc caggaaggcc aggtgcttgt acctgagcct gcgcatgcgc agcggacct    4080 cctgctccac cgactgcagc tccttggagg tcgccgggag cccagcgcg  tagagactcc   4140 ggagcagctt cacgagggtc ccgtgccaga ctgcatttat ctgggtgggg acacaggta    4200 aagtcacacc cgagtccctg atgatccaag ggtctgagct ggggctacct ccccagaacc   4260
agttcctgac ccatcatttt aaggcaggca cttcttgcag gggcaccagg ctgctcctca   4320
tggcctgtct tcggaccctg gttctccagc ctccaataaa ctctacttct gtgccagcca   4380
gccagccgtt tgctatcacg gcaagaactc agagggataa ggcaactccg ccaagagctt   4440
ccctagcaca aattccactg gtgcggctga ttcaatggag acctggctat agctctgcat   4500 gggggggcacc cctgaccatg cttgtctctc atgcacggac ctgagctgca tgccaactgc   4560
caagtccagg ggccagaaag aagcccgtag gagtgggtca agaagggacc attaggtcag   4620
ttttgtcaac cagctcattt ttttttttggt ttgttttttgg cttttttacag ctgcacccac   4680 agaagtcccc aggctagggg ttgaatcaga ggtacggctg ccggcgtaca ccacagcaac   4740
gctggatcct taacccaatg agtgaggcca gggactgaac ctgcatcctc atgggtagtt   4800
ggattcgctt cctctgagcc acaaccagaa ctccaaccca tcttttgctt gcagtgacaa   4860
ttagagtttt tagctatcaa aaacaatgac agtagttctc taggggatcc agtgttgctc   4920
ttgctgtggc gagagttcga tccctggacc gggaacttct gcataccata ggtggggcca   4980
ggataaaaca aacagaaaca acactgactt tcttcagga agataactgt cgggtctgag    5040
atgctccaga acctataccc cttttctcta agagtttcta tcaacaagga gcttcttgtg   5100
aatgcaactg ctgctttaga gcagagatgg ccttgccctc cctccagtgg tgtgactgaa   5160
gccagccagg tgtccatggg gcccaatgct gtgcaggaaa gttctttgtg ggtaaaagat   5220
tcctgttgtc acagagtccg gcccactctg aaactccggg cgctggggga cgagcagccg   5280
gctggccact tgttcagact cccctaccag ttctcatcaa accaagcatc ctgtgaggcc   5340
tcctcacccc acgctcccca tttcccccaa atcttggtgt gaacagcaca acctgaatct   5400
gcacccagca atgggaccgg ctctgccagc tccactcctg caccttggtg acccagttgt   5460
tcccaggcct cagagaaata tgggggccac ctgaggagcc cagacctccc ctcgcggaag   5520
gcagcctgtg gtacacgagt ctggctctgt cctttgctgt gctaaggctc ttaatgctgc   5580
cacgctgcac gcctcctgac ccccggtctg tgaaatgagg ctgcagctga gagtaggaac   5640
tgaaatcaca cacgagag gaggggcaag agaagggctg ctatgggaag ggctgggcag    5700
gagaatggcc cagacagcag gcgggacctt aaaagaaag ctttgtcact ggttatattt     5760
atttctaaac actttgttgc cagtttgtta ctggcttata attttgttat agtgttcagt   5820 ccttttttttt tttttttag ggccacaccc acggcatatg gaggttccca ggctagggt    5880 cgaattggag ctgtagccac cggcctacgc cagagccaca gcaacgtggg atccaagccg   5940
tgtctgcaac ctacaccaca gctcacagca acgctggatc cttaacccac tgagcaaggg   6000
cagggatcaa acccgcaacc tcatggttcc cagttgcatt cattatccac tgtgccatga   6060
```

```
cgggaactcc ctcagtcttt tttttaaatg gctgccccca accctgcata tggagtttcc      6120
gggccaggga ttgaatctga gttgcagctg caacctaagc tgcactgcgg gatccttaac      6180
ccactgggct gggggttgaa cctgtacctc cagtgatccg ggcacctgca gtcggattct      6240 tcttttttc ccccaccttaa tcacaccacc gattgaagca aaacaacacg acacgctgct      6300
gcttcaccca aaagtggtgt tttcactctg cccttcttg acggctcagt gggtcatatt       6360
caaaaggccc cctgagtgct tttagaaagg ggatgcagta ggattctaaa cccactgtgc      6420
cacagcggga acgccacaag gttcagtctt gtctctaaag cttcgcttcc actaagtgtg      6480
tttaaaatgt tcgataaata caactagaa ttatagcctt agaacaagag atctaattag       6540
gataaaattt attttacggg tcttttttgtc ttttagggct gcacccatgg tgtatggagg     6600
ttcccagcta gggggtccaa tcagaactgt agcctctggc ctacaccaga gccacagcaa      6660
gatgggattc aagctgcgtc tgtgacctac accacagctc agggcaatgc tggatcctta      6720
acccactgag caaggccagg gactgaacct gcctcctcat ggatgtcagt ccggttcgct      6780
aactgctgag ccacgacagg aactccctga ttaagataat ttttatgagc tacattctca     6840
gcaagaaata caacttgtac tgcaaccccca acacctcctc acttcactaa aagagacttc     6900
caggaaaagc ttccctcgct gcaagggaa tggtttccac agtattctcc acgacactga       6960
aaacagttgg tcacacctcc cacgctttca ggacccgcag tttagtgcag tcctcctgag      7020
ctgtgaatgt cctcattatc ccagacaagc aggcacagga ccgcgccccc ggtcctcgcc      7080
aagaccaggg gagcgagggc cagcagagcc agggtgaggg ctctacctcc cttctgcgcc     7140
gccacgggcc ctctgcctgc agccaacgct gcgacgcctg gggaagagcc tgcatgacag      7200
gagtcctgag tgcttttcag tctcctcacg ctgaacagag actggggtga ggtcgaccct     7260
tcaactcctg ccacacatag gtaggtccct tctctccacg ctcctccttt aaggatctga     7320
ccggctggat gacatctacg cccttcccct gtcactcctc ctcttctcca gcttccacta      7380
cgtctgaggg cagccagacg cggcgggtgg cggcaggact gcatggcgaa gcacccgacg     7440
cactgagagg aagcaggccc gagccccgcg ctgctgttta ctgtgtcctg gctgcctgcc      7500
caaaagatga ggacagcagt gttcagctca cggggctgct gtgagaatta acaggataaa     7560
gtactttgga atctccgaaa cgagaaacac aaacagacta caggatgttg gggaactaag     7620
cactcagcag agctcccgtc tatacctacg aagcaaccgg aggctttggg ctccagaacc      7680
cacctggctg ttaacaagac ggagaaggtg ctgaaagcgg gcatccttga tgagcaaggc      7740
tttgtctttc ggcttctcag acagcaggcg ggagagctgg atgaccatga gggccgcgcg     7800
gttctggtgc agacagtggc cgccaccaag cagcgccagg atctcctctg gctgggtggc     7860
cctctcgatg agatggtcta cctcctggcg ctccgggtag ggagtaaaca cttgtcccct     7920
ctccacaagc tctgacaagg aaccaggag gtggagctg ggcgaggtag ccgaggaggt       7980
cagagtcctg ggggctcccc gggtgagtct cggctggcca accggagaca tggcaggggc     8040
cagacgggcg gcctctctca ggaggcacgt gcatcgcctc accaggcgag atgccatgac      8100
tggtagcccg gtggtgggga gggaagactg ctagcaaggg agtccaaagc cctgcagagc      8160
aaaaggagag agaaggggt ggtgtggggg gcggctcctg actcacaaac acaacagaag      8220
aacatgctga atggagtcac tgccacactt cccacaaagc agcctgagcc cctcctgact      8280
gtccacacgc aacagtgttt tctgaagcaa aaatctgaag gctcccaccc cccacccta      8340 gattagaata caaccaaata tccaaaatca gagcatcaca gcttgggctg gaggatttta     8400
```

```
gtcttggttg tgtagtcacc tcgggaatgg tgaaccactg cagaatccca ggcccgtcca    8460
agacttccag agtgggtttc tctgcaaaca gcattccttt tttgggggggg tagaggttgc    8520
tatacccaca gcaggtggaa attcctgggc cagggattga acccgtgcca cagctgtgac    8580
cagagccacg gcagtgatac cagagcctaa cccattgagc cacgagggaa ctccttttttg   8640
ttggaggtcc cattgtgact cattgggtta agaactggac atagtctcag tgaagatgca    8700
ggttcaagcc ctggcctcgc tcagtgggtt aaggatctgg cgttgccaca agttgcagtg    8760
agggttgcag atgtggcttg gatctggtgt tgctggggct gtgacacagg caggcagctg    8820
tacctctgat ttgaccccta gcctaggaac ttccacatgc tgcaagtgtg gccctaaaaa    8880
gcaaaaaaat gaaaaaaaaa attttttttta aagtacccag gattaaaaat tattacctta   8940
cagtagagac gatgagacag aattttttttt tttttttttt ttggtctttt tcatctcttc   9000
agggctgcgc ctgtggcata tggaatttcc caggctgggg ggttgaatca gagctctaac    9060
tgccggcctg tatcacagcc acagcaatgc tggatccgag ctgtgtctgc gacctacacc    9120
agaactcatg gcaatgctgg atccttaatc cacggagaga ggccagggat tgaacctgca    9180
acctcatggc tcctagtctg attcatttcc cctgtgccac gacgggaact acttttttttt   9240
tttcttttgg agacagaata ttttaaatta gactactcct ggaaaaccct ggacatataa   9300
tccatacata tcccagaact cctgaggtgt agaaatatt                          9339
```